(12) United States Patent
Mattson et al.

(10) Patent No.: US 9,682,980 B2
(45) Date of Patent: Jun. 20, 2017

(54) POSITIVE ALLOSTERIC MODULATORS OF MGLUR2

(71) Applicant: BRISTOL-MYERS SQUIBB COMPANY, Princeton, NJ (US)

(72) Inventors: Ronald J. Mattson, Meriden, CT (US); Zhaoxing Meng, Middletown, CT (US); Leatte R. Guernon, Moodus, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/406,029

(22) PCT Filed: Jun. 19, 2013

(86) PCT No.: PCT/US2013/046572
§ 371 (c)(1),
(2) Date: Dec. 5, 2014

(87) PCT Pub. No.: WO2013/192306
PCT Pub. Date: Dec. 27, 2013

(65) Prior Publication Data
US 2015/0152113 A1    Jun. 4, 2015

Related U.S. Application Data

(60) Provisional application No. 61/662,585, filed on Jun. 21, 2012.

(51) Int. Cl.
*C07D 491/107* (2006.01)
*C07D 487/04* (2006.01)
(52) U.S. Cl.
CPC ....... *C07D 487/04* (2013.01); *C07D 491/107* (2013.01)
(58) Field of Classification Search
CPC ..................... C07D 491/107; C07D 487/04
USPC ................. 544/230, 236, 263; 514/248
See application file for complete search history.

(56) References Cited

U.S. PATENT DOCUMENTS 8,642,660 B2 * 2/2014 Goldfarb ............ A61K 31/122
514/18.9
8,765,767 B2   7/2014 Mattson et al.
2009/0163545 A1 * 6/2009 Goldfarb ............ A61K 31/122
514/312

FOREIGN PATENT DOCUMENTS

WO    WO 2010/130424        11/2010
WO    WO2012/125732    *    9/2012

OTHER PUBLICATIONS

Wermuth et al, Molecular variations based on isosteric replacements. 1996WO2012/125732.*
Zhigang Zhou et al , 2010 QSAR models for predicting cathepsin B inhibition by small molecules—continuous and binary QSAR models to classify cathepsin B inhibition activities of small molecules.*
Marcin et al., U.S. Appl. No. 61/879,925, filed Sep. 19, 2013.

* cited by examiner

*Primary Examiner* — Rita Desai
(74) *Attorney, Agent, or Firm* — James Epperson

(57) ABSTRACT

The disclosure generally relates to compounds of formula I, including their salts, as well as compositions and methods of using the compounds. The compounds modulate the mGluR2 receptor and may be useful for the treatment of various disorders of the central nervous system. Formula (I):

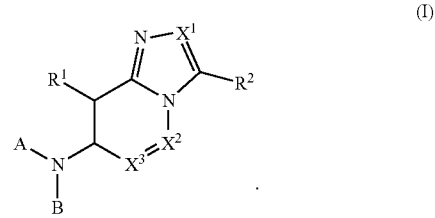

9 Claims, No Drawings

POSITIVE ALLOSTERIC MODULATORS OF MGLUR2

BACKGROUND OF THE INVENTION

The disclosure generally relates to compounds of formula I, including their salts, as well as compositions and methods of using the compounds. The compounds are ligands, agonists and partial agonists for the mGluR2 PAM receptor and may be useful for the treatment of various disorders of the central nervous system.

Glutamate is the major excitatory neurotransmitter in the mammalian brain, playing an important physiological role in a wide variety of processes. Glutamatergic neurotransmission is predominantly mediated through activation of cell surface receptors including ligand-gated ion channels (ionotropic receptors) and metabotropic glutamate G protein coupled receptors (mGluRs). The metabotropic glutamate receptor family is comprised of 8 family members that are part of the family 3 GPCR superfamily. These receptors are further subdivided into Group I (mGluR 1, 5), Group II (mGluR 2, 3) and Group III (mGluR 4, 6, 7, 8) based upon sequence homology, receptor signaling, and pharmacology.

At the cellular level, mGluR2 plays a key role as an autoreceptor in glutamate terminals, though it is generally thought to be localized at the periphery of the synapse, away from the active zone. Activation of the mGluR2 receptor by glutamate or other orthosteric ligands results in a reduction of adenylate cyclase via a Gαi protein and a subsequent reduction of glutamate release from the pre-synaptic terminal. mGluR2 receptors are localized to regions of the brain involved with psychiatric disorders, including the prefrontal cortex, striatum, hippocampus, and amygdala. Excessive glutamate release has been hypothesized to contribute to the underlying pathophysiology in both anxiety and schizophrenia; therefore, activators of mGluR2 receptors may offer therapeutic benefits in these disorders. This biological phenomenon was demonstrated pre-clinically in a study by Moghaddam and Adams (1998) in which they treated rats with phencyclidine (PCP), an NMDA receptor blocker, and detected increased glutamate release in the mPFC and striatum of these animals as well as hyper-locomotion and working memory deficits. The mGluR2/3 agonist, LY-354740, lowered brain glutamate levels and reversed the behavioral effects of PCP. Many more studies have demonstrated efficacy in a variety of pre-clinical models of psychosis and anxiety with mGluR2/3 agonists. Such pre-clinical work led to the development of mGluR2/3 agonists for both anxiety and schizophrenia. Eli Lilly reported therapeutic effects of LY-544344 for anxiety in GAD patients (Dunayevich et al., 2008) and with LY-2140023 for relief of positive and negative symptoms in schizophrenia (Patil et al., 2007).

To date, most of the available pharmacological tools targeting the mGluR2 receptor have been structural analogues of glutamate and act as orthosteric agonists. While demonstrating proof of principle for use in psychiatric disease, agonists have poor pharmacokinetic profiles and poor brain penetration. Furthermore, several pre-clinical studies have demonstrated tolerance to mGluR2/3 agonists upon repeated dosing in rodents (Cartmell et al., 2000; Galici et al., 2005; Jones et al., 2005). Unlike orthosteric agonists, positive allosteric modulators (PAMs) only activate the receptor when glutamate or another orthosteric agonist is present. Therefore, PAMs are thought to retain spatial and temporal activity of glutamate transmission in the brain and would not continuously stimulate the mGluR2 receptor, potentially avoiding tolerance or unwanted side effects of the agonists. Furthermore, since PAMs bind to an allosteric site on the receptor, they can be designed to be selective for the mGluR2 receptor. Pre-clinical studies and early development of mGluR2 PAMs suggest that they will be effective therapies for positive and negative symptoms and co-morbidy anxiety in schizophrenia.

Based on the expression pattern and functional role of mGluR2, this receptor has emerged as an important target for drug discovery in a number of therapeutic indications. In clinical trials, activating mGluR2 was shown to be efficacious in treating anxiety disorders. In addition, activating mGluR2 has been shown to be efficacious in various animal models of schizophrenia, epilepsy, addiction/drug dependence, Parkinson's disease, pain, sleep disorders, and Huntington's disease. See the following publications: Positive allosteric modulators of the metabotropic glutamate receptor 2 for the treatment of schizophrenia. Mark E Fraley; *Expert Opin. Ther. Patents* (2009) 19(8); Biphenyl-indanone A, a positive allosteric modulator of the metabotropic glutamate receptor subtype 2, has antipsychotic- and anxiolytic-like effects in mice. Galici Ruggero; et al. *The Journal of Pharmacology and Experimental Therapeutics* (2006), 318 (1), 173-85; Potential psychiatric applications of metabotropic glutamate receptor agonists and antagonists. Krystal, John; et al. *CNS Drugs* (2010), 24(8), 669-693; Postsynaptic and presynaptic group II metabotropic glutamate receptor activation reduces neuronal excitability; in rat midline paraventricular thalamic nucleus. Hermes M L H J; et al.; *The Journal of Pharmacology and Experimental Therapeutics* (2011), 336(3), 840-9; Scaffold hopping from pyridones to imidazo[1,2-a]pyridines. New positive allosteric modulators of metabotropic glutamate 2 receptor. Gary Tresadern, et al.; *Bioorganic & Medicinal Chemistry Letters* 20 (2010) 175-179; 3-Benzyl-1,3-oxazolidin-2-ones as mGluR2 positive allosteric modulators: Hit-to lead and lead optimization. Allen J. Duplantier, et al.; *Bioorganic & Medicinal Chemistry Letters* 19 (2009) 2524-2529. Use of mGluR2 PAMs for the treatment of cocaine dependence: Design and synthesis of an orally active metabotropic glutamate receptor subtype-2 (mGluR2) positive allosteric modulator (PAM) that decreases cocaine self-administration in rats. Dhanya, Raveendra-Panickar; et al.; *Journal of Medicinal Chemistry* (2011), 54(1), 342-353; The mGluR2 Positive Allosteric Modulator BNA Decreases Cocaine Self-Administration and Cue-Induced Cocaine-Seeking and Counteracts Cocaine-Induced Enhancement of Brain Reward Function in Rats. Jin, Xinchun; et al.; *Neuropsychopharmacology* (2010), 35(10), 2021-2036.

The invention provides technical advantages, for example, the compounds are novel and are ligands for the mGluR2 receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating anxiety, schizophrenia, epilepsy, addiction/drug dependence, Parkinson's disease, pain, sleep disorders, or Huntington's disease, or other neurological or psychiatric disorders associated with glutamate dysfunction.

One aspect of the invention is a compound of formula I

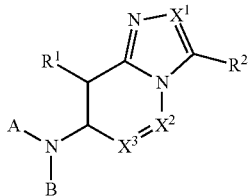

wherein:
A is Ar¹—Y—Z;
B is hydrogen or alkyl;
or A and B together with the nitrogen to which they are attached form ring A;
R¹ is selected from the group consisting of hydrogen, cyano, halo, alkyl, haloalkyl, (cycloalkyl)alkyl, cycloalkyl, alkoxy, and haloalkoxy;
R² is selected from the group consisting of alkyl, haloalkyl, (cycloalkyl)alkyl, benzyl, and cycloalkyl;
R³ is hydrogen, alkyl, haloalkyl, or cycloalkyl;
Ar¹ is phenyl, pyridinyl, pyridazinyl, pyrimidinyl, pyrazinyl, or triazinyl, and is substituted with 0-3 substituents selected from cyano, halo, alkyl, haloalkyl, cycloalkyl, alkoxy, and haloalkoxy;
Ar² is phenyl, pyridinyl, pyridazinyl, pyrimidinyl, pyrazinyl, or triazinyl, and is substituted with 0-3 substituents selected from cyano, halo, alkyl, haloalkyl, hydroxyalkyl, alkoxyalkyl, cycloalkyl, hydroxy, alkoxy, (cycloalkyl)alkoxy, haloalkoxy, and alkoxycarbonyl;
X¹ is CH or N;
X² is CR³ or N;
X³ is CH or N;
provided that one of X² and X³ is N, thus when X² is N, X³ is CH and when X³ is N, X² is CR³;
Y is C₃₋₆ cycloalkyl substituted with 0-2 halo or alkyl substituents; and
Z is a bond or C₁₋₃ alkyl;
ring A is azetidinyl, pyrrolidinyl, piperidinyl, piperazinyl, morpholinyl, homopiperidinyl, homopiperazinyl, or homomorpholinyl, and is substituted with 1 Ar² or (Ar²)alkyl substituent and is also substituted with 0-3 substituents selected from halo, alkyl, haloalkyl, hydroxy, alkoxy, and haloalkoxy;
or ring A is selected from the group consisting of

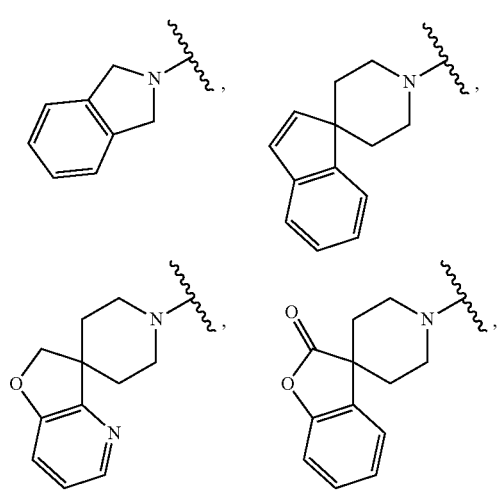

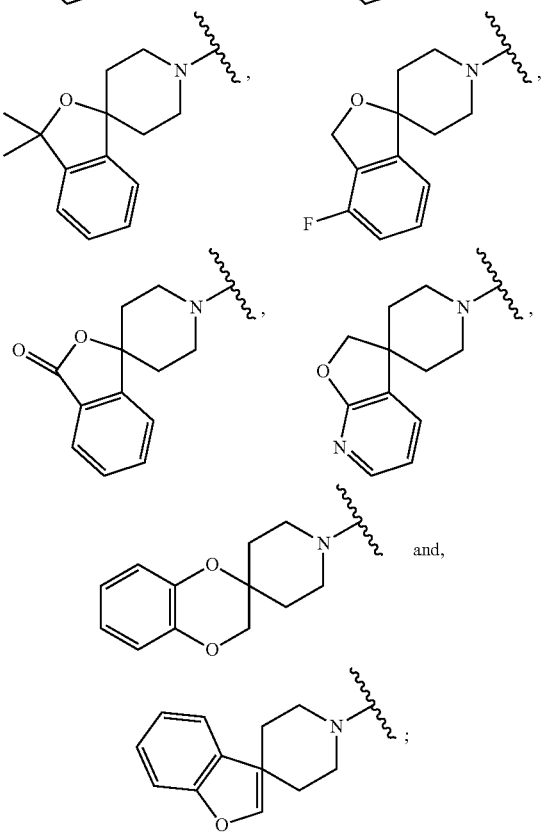

or a pharmaceutically acceptable salt thereof.
Another aspect of the invention is a compound of formula I where X¹ is N.
Another aspect of the invention is a compound of formula I where X² is N and X³ is CH.
Another aspect of the invention is a compound of formula I where X² is CH and X³ is N.
Another aspect of the invention is a compound of formula I where R¹ is selected from the group consisting of hydrogen, halo, alkyl, haloalkyl, and alkoxy and R² is selected from the group consisting of alkyl, haloalkyl, (cycloalkyl)alkyl, and benzyl.
Another aspect of the invention is a compound of formula I where B is hydrogen; Ar¹ is phenyl and is substituted with 0-3 substituents selected from cyano, halo, alkyl, haloalkyl, cycloalkyl, alkoxy, and haloalkoxy; Y is C₃₋₆ cycloalkyl; and Z is C₁₋₃ alkyl; or a pharmaceutically acceptable salt thereof.
Another aspect of the invention is a compound of formula I where Y is cyclopropyl; and Z is methylene; or a pharmaceutically acceptable salt thereof.
Another aspect of the invention is a compound of formula I where Ar¹ is phenyl substituted with 0-3 substituents selected from cyano, halo, alkyl, haloalkyl, cycloalkyl, alkoxy, and haloalkoxy.

Another aspect of the invention is a compound of formula I where Ar¹ is phenyl substituted with 0-3 substituents selected from halo and alkoxy.
Another aspect of the invention is a compound of formula I where Ar¹ is phenyl or pyrimidinyl substituted with 0-3 substituents selected from halo and alkoxy.
Another aspect of the invention is a compound of formula I where Ar¹ is heteroaryl substituted with 0-3 substituents selected from cyano, halo, alkyl, haloalkyl, cycloalkyl, alkoxy, and haloalkoxy.
Another aspect of the invention is a compound of formula I where Ar¹ is pyridinyl, pyridazinyl, pyrmidinyl, pyrazinyl, or triazinyl and is substituted with 0-3 substituents selected from cyano, halo, alkyl, haloalkyl, cycloalkyl, alkoxy, and haloalkoxy
Another aspect of the invention is a compound of formula I where Ar¹ is pyrimidinyl substituted with 0-3 substituents selected from halo and alkoxy.
Another aspect of the invention is a compound of formula I where Ar² is phenyl, pyridinyl, or pyrimidinyl, and is substituted with 0-3 substituents selected from cyano, halo, alkyl, haloalkyl, hydroxyalkyl, alkoxyalkyl, cycloalkyl, hydroxy, alkoxy, (cycloalkyl)alkoxy, haloalkoxy, and alkoxycarbonyl.
Another aspect of the invention is a compound of formula I where ring A is piperidinyl substituted with 1 Ar² substituent and is also substituted with 0-1 hydroxy substituents.
Another aspect of the invention is a compound of formula I where ring A is selected from

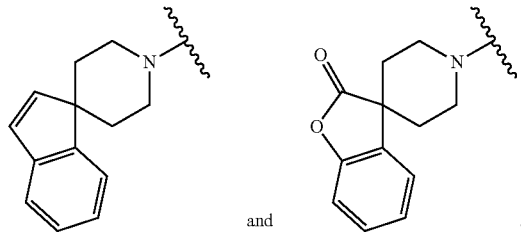

and

Another aspect of the invention is a compound of formula I where X¹ is N.
Another aspect of the invention is a compound of formula I where X¹ is CH.
Another aspect of the invention is a compound of formula I where X² is N and X³ is CH.
Another aspect of the invention is a compound of formula I where X³ is N and X² is CH.
Another aspect of the invention is a compound of formula I where Y is cyclopropyl.
Another aspect of the invention is a compound of formula I where Z is $C_{1-3}$alkyl.
Another aspect of the invention is a compound of formula I where Z is methylene.

For a compound of formula I, the scope of any instance of variable substituent, including R¹, R², R³, Ar¹, Ar², X¹, X², X³, Y, Z, and ring A, can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The formula and variable designations used to describe the synthesis of the compounds are intended only to illustrate how to make the compounds and not to be confused with variables used in the claims or in other sections of the specification. The following methods are for illustrative purposes and are not intended to limit the scope of the invention. The schemes encompass reasonable variations known in the art.

When $R^1$ is not hydrogen, the compounds of Formula I can be prepared by the methods described in Scheme 1. A trisubstituted diazine, 1, is reacted with an appropriate amine in the presence of a base such as sodium carbonate, and in a solvent such as dioxane, to give intermediate 2. Subsequent reaction of intermediate 2 with an appropriately substituted alkylhydrazide, yields intermediate 3. Alternatively, intermediate 2 can be reacted first with hydrazine, and then acylated with an appropriate carboxylic acid halide or acyl imidazole to give intermediate 3. Further cyclization of intermediate 3 under dehydrating conditions with reagents such as $POCl_3$, Burgess' reagent, or $PPh_3/TMS-N_3/DEAD$ gives the compounds of Formula I.

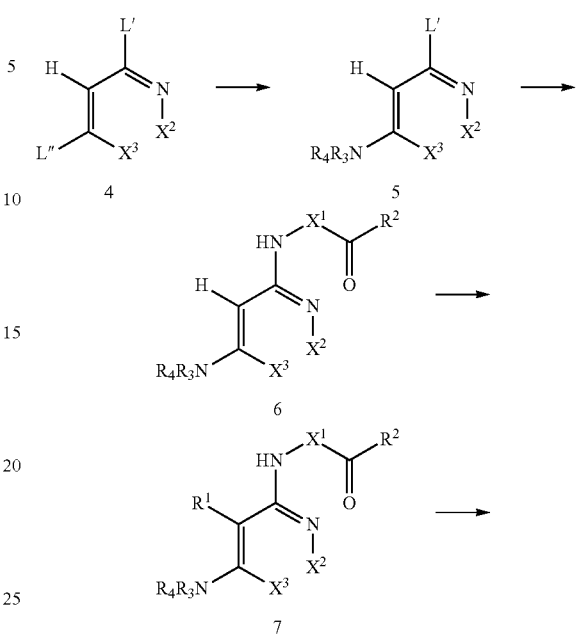

When $R^1$ is hydrogen, the compounds of Formula I can be prepared by the methods described in Scheme 2. A dihalo diazine, 4, is reacted with an appropriate amine in the presence of a base such as sodium carbonate, and in a solvent such as dioxane, to give intermediate 5. Subsequent reaction of intermediate 5 with an appropriately substituted alkylhydrazide, yields intermediate 6. Alternatively, intermediate 5 can be reacted first with hydrazine, and then acylated with an appropriate carboxylic acid halide or acyl imidazole to give intermediate 6. Reaction of intermediate 6 with reagents such as N-chlorosuccinimide give intermediate 7. Cyclization of intermediate 7 under dehydrating conditions with reagents such as $POCl_3$, Burgess' reagent, or $PPh_3/TMS-N_3/DEAD$ gives compounds of Formula I.

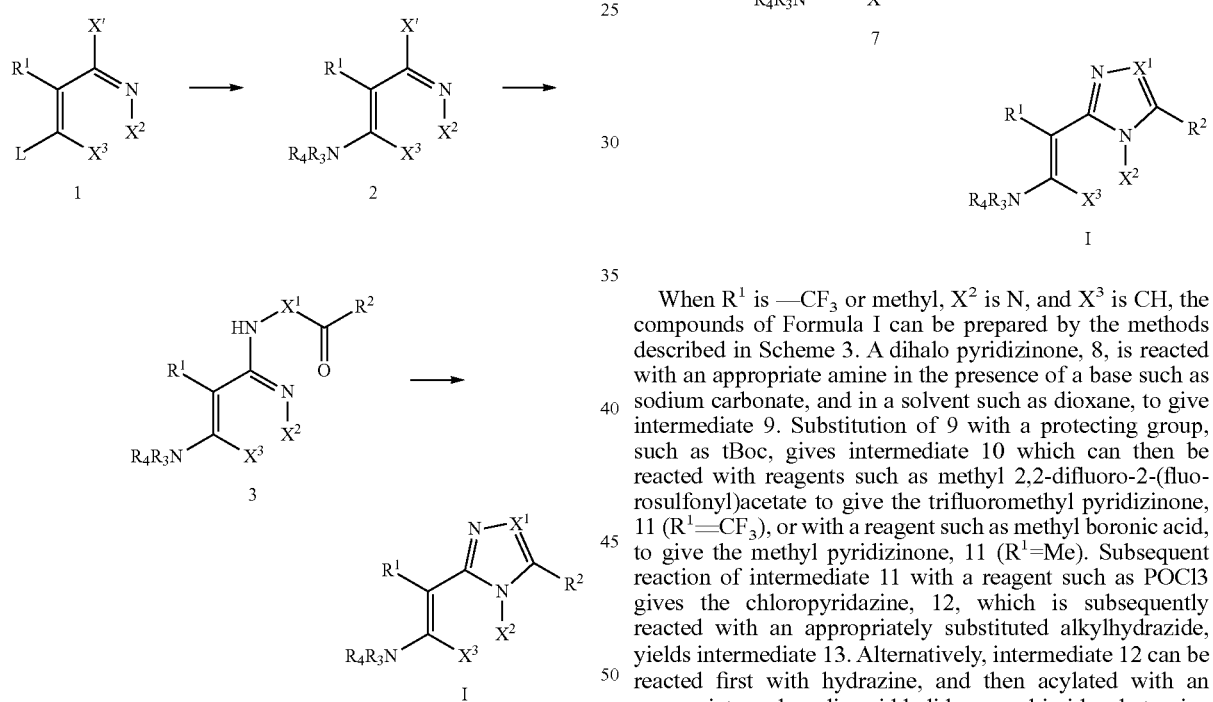

When $R^1$ is $-CF_3$ or methyl, $X^2$ is N, and $X^3$ is CH, the compounds of Formula I can be prepared by the methods described in Scheme 3. A dihalo pyridizinone, 8, is reacted with an appropriate amine in the presence of a base such as sodium carbonate, and in a solvent such as dioxane, to give intermediate 9. Substitution of 9 with a protecting group, such as tBoc, gives intermediate 10 which can then be reacted with reagents such as methyl 2,2-difluoro-2-(fluorosulfonyl)acetate to give the trifluoromethyl pyridizinone, 11 ($R^1=CF_3$), or with a reagent such as methyl boronic acid, to give the methyl pyridizinone, 11 ($R^1=Me$). Subsequent reaction of intermediate 11 with a reagent such as $POCl3$ gives the chloropyridazine, 12, which is subsequently reacted with an appropriately substituted alkylhydrazide, yields intermediate 13. Alternatively, intermediate 12 can be reacted first with hydrazine, and then acylated with an appropriate carboxylic acid halide or acyl imidazole to give intermediate 13. Cyclization of intermediate 13 under dehydrating conditions with reagents such as $POCl_3$, Burgess' reagent, or $PPh_3/TMS-N_3/DEAD$ gives compounds of Formula I.

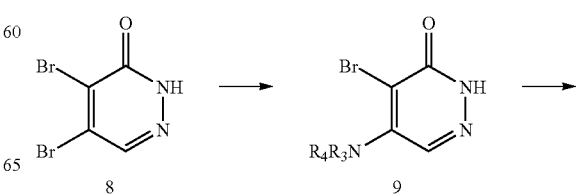

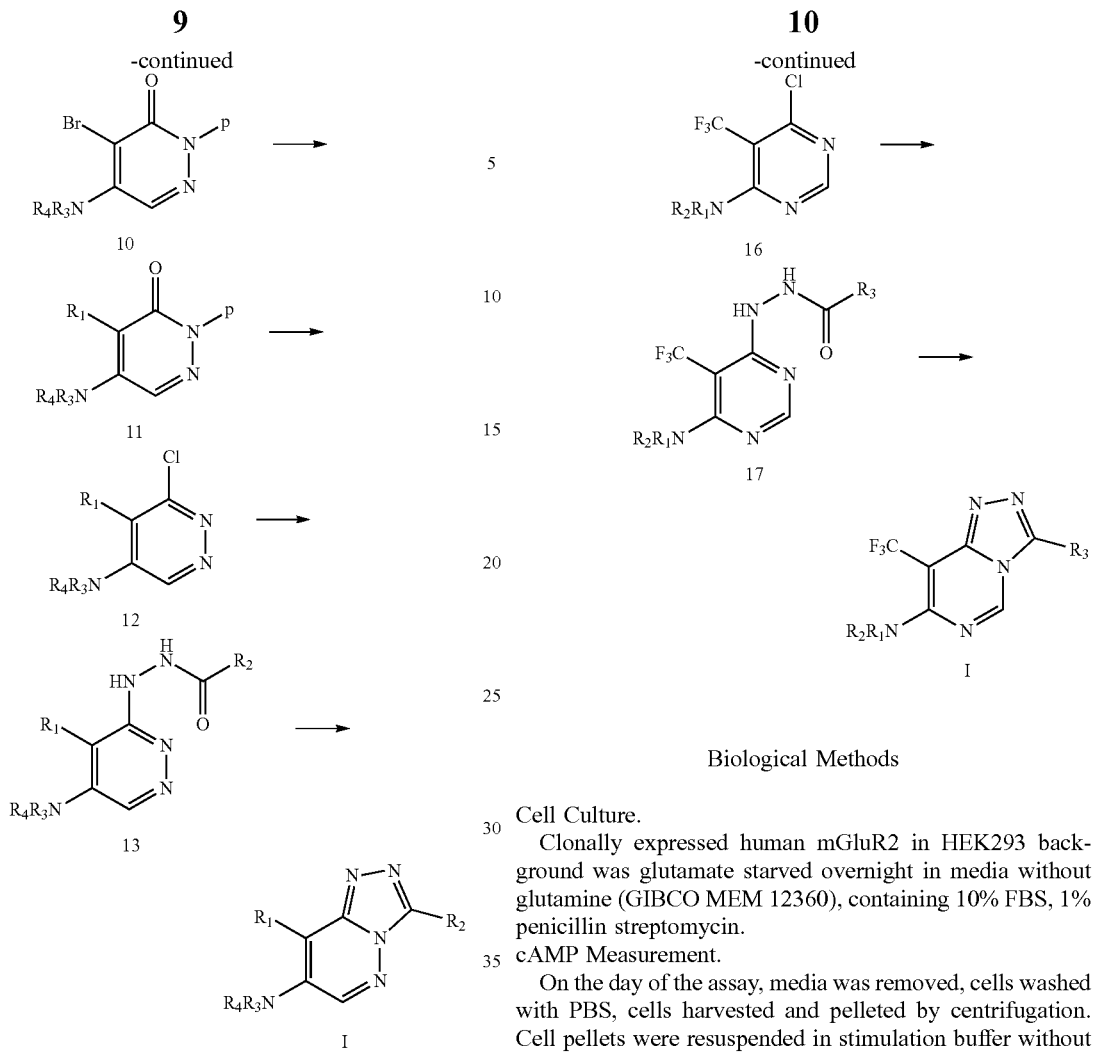

When R¹ is —CF₃, X² is CH, and X³ is N, the compounds of Formula I can be prepared by the methods described in Scheme 4. Pyrimidine, 14, is reacted with an appropriate amine in the presence of a base such as sodium carbonate, and in a solvent such as dioxane, to give intermediate 15. Subsequent reaction of intermediate 15 with a reagent such as POCl₃ gives the chloropyrimidine, 16, which is subsequently reacted with an appropriately substituted alkylhydrazide, yields intermediate 17. Alternatively, intermediate 16 can be reacted first with hydrazine, and then acylated with an appropriate carboxylic acid halide or acyl imidazole to give intermediate 17. Cyclization of intermediate 17 under dehydrating conditions with reagents such as POCl₃, Burgess' reagent, or PPh₃/TMS-N₃/DEAD gives compounds of Formula I.

Scheme 4.

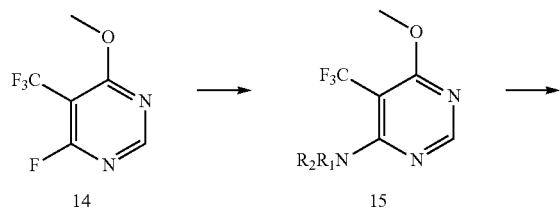

Biological Methods

Cell Culture.

Clonally expressed human mGluR2 in HEK293 background was glutamate starved overnight in media without glutamine (GIBCO MEM 12360), containing 10% FBS, 1% penicillin streptomycin.

cAMP Measurement.

On the day of the assay, media was removed, cells washed with PBS, cells harvested and pelleted by centrifugation. Cell pellets were resuspended in stimulation buffer without forskolin and counted. A solution of $1.25 \times 10^6$ cells/ml was prepared and dispensed to plates using a Combi liquid handler (Thermo). A standard curve was created using a top concentration of cAMP of 1 μM in the stimulation buffer, 1:3 dilutions over 14 points in the absence of cells. Plates were read by time-resolved fluorescence at 665 nM and 618 nM and a ratio was calculated via in house software, (665 nM/618 nM)*10⁴. In house software converted the fluorescence value ratios to units of cAMP concentration, which is then used to calculate % inhibition for each test compound.

MGluR2 cAMP Assay Materials and Methods.

Compounds were added to white, standard volume 384 non-binding surface plates (Corning 3574). Cells were resuspended in stimulation buffer consisting of Hanks Balanced Salt Solution (14175-095) pH 7.0, 20 mM HEPES, 2.0 mM CaCl₂, 5.0 mM MgCl₂, and 1 mM IBMX (Sigma 15879), 1 μM forskolin, and 1 μM LY-341495, for 30 minutes. Buffer without forskolin was used as a negative control. Solutions of D2 and cryptate detection reagents from the CISBIO dynamic cAMP kit (62AM4PEJ) were diluted 1:40 in lysis buffer. Lysis buffer consisted of 50 mM Phosphate Buffer pH 7.0, 800 mM Potassium Fluoride, 0.2% BSA, and 1.0% Triton. Assay reaction was terminated by addition of detection reagents in lysis buffer. One hour later, plates were read on a PE Viewlux. Data was extracted, and concentration response curves generated by fitting the data to a standard 4 parameter logistic equation from which EC₅₀ values were determined See table 1: A: <10 nM; B: 10-100 nM; C: 100-1000 nM; D: 1000-10000 nM.

TABLE 1

| Example | EC$_{50}$ (nM) |
|---|---|
| 1 | 8 |
| 2 | 62 |
| 3 | 540 |
| 4 | 69 |
| 5 | 19 |
| 6 | 182 |
| 7 | 3 |
| 8 | 61 |
| 9 | 76 |
| 10 | 158 |
| 11 | 60 |
| 12 | 519 |
| 13 | 286 |
| 14 | 782 |
| 15 | 280 |
| 16 | 437 |
| 17 | 46 |
| 18 | 145 |
| 19 | 614 |
| 20 | 145 |
| 21 | 2310 |
| 22 | 3 |
| 23 | 13 |
| 24 | 25 |
| 25 | 20 |
| 26 | 2 |
| 27 | 9 |
| 28 | 38 |
| 29 | 21 |
| 30 | 18 |
| 31 | 38 |
| 32 | 15 |
| 33 | 21 |
| 34 | 649 |
| 35 | 6 |
| 36 | 7 |
| 37 | 9 |
| 38 | 5 |
| 39 | 28 |
| 40 | 31 |
| 41 | 275 |
| 42 | 11 |
| 43 | 10 |
| 44 | 45 |
| 45 | 48 |
| 46 | 154 |
| 47 | 144 |
| 48 | 263 |
| 49 | 425 |
| 50 | 2 |
| 51 | 3 |
| 52 | 8 |
| 53 | 6 |
| 54 | 10 |
| 55 | 21 |
| 56 | 62 |
| 57 | 217 |
| 58 | 201 |
| 59 | 121 |
| 60 | 94 |
| 61 | 225 |
| 62 | 47 |
| 63 | 185 |
| 64 | 733 |
| 65 | 36 |
| 66 | 23 |
| 67 | 5 |
| 68 | 4 |
| 69 | 438 |
| 70 | 3 |
| 71 | 4 |
| 72 | 15 |
| 73 | 18 |
| 74 | 14 |
| 75 | 16 |
| 76 | 34 |
| 77 | 4 |
| 78 | 7 |

TABLE 1-continued

| Example | EC$_{50}$ (nM) |
|---|---|
| 79 | 382 |
| 80 | 0.2 |
| 81 | 0.4 |
| 82 | 809 |
| 83 | 42 |
| 84 | 4 |
| 85 | 10 |

Pharmaceutical Compositions and Methods of Treatment

Compounds of formula I modulate to mGluR2 and can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of anxiety, schizophrenia, epilepsy, addiction/drug dependence, Parkinson's disease, pain, sleep disorders, or Huntington's disease, or other neurological or psychiatric disorders associated with glutamate dysfunction, which comprises administering to a patient a therapeutically affective amount of a compound of formula I.

Another aspect of the invention is a method for the treatment of anxiety or schizophrenia which comprises administering to a patient a therapeutically affective amount of a compound of formula I.

Another aspect of the invention is a method for the treatment of anxiety which comprises administering to a patient a therapeutically affective amount of a compound of formula I.

Another aspect of the invention is a method for the treatment of schizophrenia which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of anxiety, schizophrenia, epilepsy, addiction/drug dependence, Parkinson's disease, pain, sleep disorders, or Huntington's disease, or other neurological or psychiatric disorders associated with glutamate dysfunction.

Another aspect of the invention is the use of a compound of formula I in the manufacture of a medicament for the treatment of anxiety.

Another aspect of the invention is the use of a compound of formula I in the manufacture of a medicament for the treatment of schizophrenia.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

$^1$H-NMR spectra were run on a Bruker 500 or 300 MHz instrument and chemical shifts were reported in ppm (δ) with reference to tetramethylsilane (=0.0). Unless otherwise stated, LCMS analyses were carried out on a Waters Acquity BEH C18, 2.0×50 mm, 1.7-µm particle size column employing a flow rate of 0.5 mL/min using a 10 mM ammonium acetate in methanol/water gradient, 5-95%, with a 5 min run time, at 40° C. and a UV detector set at 220 nM. Alternatively, LCMS Method B was used (Walters Acquity C18, 2.1×50 mm, 1.7-µm particle size column, with a flow rate of 0.8 mL/min using 0.05% TFA in acetonitrile/water gradient, 2-98%, with a 2.2 min run time, at 40° C. and a UV detector set at 220 nM).

Example 1

8-Chloro-3-(cyclopropylmethyl)-7-(4-phenylpiperidin-1-yl)-[1,2,4]triazolo[4,3-c]pyrimidine 4-Hydrazinyl-6-(4-phenylpiperidin-1-yl)pyrimidine A mixture of 4,6-dichloropyrimidine (0.924 g, 6.20 mmol), 4-phenylpiperidine (1, 6.20 mmol), saturated sodium carbonate (10 ml) and dioxane (30 ml) was stirred for 2 h. The mixture was diluted with ethyl acetate and stirred. The ethyl acetate layer was separated, washed with water, dried with brine, and concentrated to a white solid. The white solid was heated to reflux for 2 days in dioxane (10 ml) and 35% hydrazine in water (10 ml). The mixture was cooled and diluted with ethyl acetate. The ethyl acetate layer was separated, washed with water, dried with brine, and concentrated to give 4-hydrazinyl-6-(4-phenylpiperidin-1-yl)pyrimidine as a white solid (1.67 g, 100%) which was used without purification. LCMS: Rt=0.79 min, 87%, (M+H)$^+$=270, 271.

2-Cyclopropyl-N'-(6-(4-phenylpiperidin-1-yl)pyrimidin-4-yl)acetohydrazide

A solution of 2-cyclopropylacetic acid (0.745 g, 7.44 mmol) in thionyl chloride (10 ml, 115 mmol) was heated to reflux for 1 h. The solution was concentrated and the residue was dissolved in ethyl acetate (50 ml) and added to a stirred mixture of 4-hydrazinyl-6-(4-phenylpiperidin-1-yl)pyrimidine (1.67 g, 6.20 mmol) in dioxane (50 ml) and saturated sodium carbonate (25 ml). The mixture was stirred for 1 hr and then concentrated. The residue was washed with water and air dried to give 2-cyclopropyl-N'-(6-(4-phenylpiperidin-1-yl)pyrimidin-4-yl)acetohydrazide as a pink solid (1.696 g, 78%). LCMS: Rt=0.80, 72%, (M+H+=352, 353.

N'-(5-Chloro-6-(4-phenylpiperidin-1-yl)pyrimidin-4-yl)-2-cyclopropylacetohydrazide A mixture of 2-cyclopropyl-N'-(6-(4-phenylpiperidin-1-yl)pyrimidin-4-yl)acetohydrazide (0.5 g, 1.423 mmol) and NCS (0.2 g, 1.498 mmol) in THF (10 ml) was stirred at room temperature for 4 h. The solution was diluted with ethyl acetate, washed with water, dried with brine, and concentrated. The residue was dissolved in methylene chloride and applied to a silica gel column. The product was eluted with 25-100% ethyl acetate/methylene chloride. The product fractions were concentrated to give N'-(5-chloro-6-(4-phenylpiperidin-1-yl)pyrimidin-4-yl)-2-cyclopropylacetohydrazide as a red resin that solidified to a foam (0.25 g, 45.5%). $^1$H NMR (400 MHz, CHLOROFORM-d) δ 8.93 (br. s., 1H), 8.20 (s, 1H), 7.70 (br. s., 1H), 7.38-7.30 (m, 2H), 7.29-7.19 (m, 4H), 4.38 (d, J=13.1 Hz, 2H), 3.02 (td, J=12.6, 2.4 Hz, 2H), 2.77 (tt, J=12.0, 3.8 Hz, 1H), 2.29 (d, J=7.0 Hz, 2H), 2.00-1.91 (m, 2H), 1.91-1.77 (m, 2H), 1.10 (quint, J=7.6, 4.8 Hz, 1H), 0.69-0.61 (m, 2H), 0.31-0.23 (m, 2H).

8-Chloro-3-(cyclopropylmethyl)-7-(4-phenylpiperidin-1-yl)-[1,2,4]triazolo[4,3-c]pyrimidine A mixture of N'-(5-chloro-6-(4-phenylpiperidin-1-yl)pyrimidin-4-yl)-2-cyclopropylacetohydrazide (0.25 g, 0.648 mmol) and Burgess' reagent (0.310 g, 1.301 mmol) in THF (5 ml) was heated in an 80° C. oil bath for 4 h. An additional portion of Burgess' reagent (0.310 g, 1.301 mmol) was added and the mixture was heated to 80° C. in an oil bath for 4 h. The reaction with diluted with ethyl acetate and and aqueous sodium carbonate. The ethyl acetate layer was separated, washed with water, dried with brine, and concentrated to a red material. The material was dissolved in methylene chloride and applied to a silica gel column. The product was eluted with 0-100% ethyl acetate/methylene chloride. The product fractions were concentrated to give 8-chloro-3-(cyclopropylmethyl)-7-(4-phenylpiperidin-1-yl)-[1,2,4]triazolo[4,3-c]pyrimidine as a pink solid (67 mg, 28%). $^1$H NMR (400 MHz, CHLOROFORM-d) δ 8.64 (s, 1H), 7.38-7.31 (m, 2H), 7.30-7.21 (m, 4H), 4.32 (dt, J=13.1, 1.9 Hz, 2H), 3.23-3.12 (m, 2H), 3.10 (d, J=6.8 Hz, 2H), 2.79 (tt, J=11.9, 3.9 Hz, 1H), 2.03-1.95 (m, 2H), 1.95-1.82 (m, 2H), 1.18 (ttt, J=8.1, 6.7, 4.9 Hz, 1H), 0.73-0.65 (m, 2H), 0.41-0.34 (m, 2H). LCMS: Rt=0.93 min, 79%, (M+H)$^+$= 368, 370.

Example 2

3-(Cyclopropylmethyl)-8-methyl-7-(4-phenylpiperidin-1-yl)-[1,2,4]triazolo[4,3-c]pyrimidine 4-Hydrazinyl-5-methyl-6-(4-phenylpiperidin-1-yl)pyrimidine A mixture of 4,6-dichloro-5-methylpyrimidine (1 g, 6.13 mmol), 4-phenylpiperidine (1.088 g, 6.75 mmol), and potassium carbonate (2.120 g, 15.34 mmol) in dioxane (50 ml) was stirred at room temperature for 1 hr and then heated to reflux for 16 h. The mixture was cooled and 35% hydrazine (11 ml, 123 mmol) was added. The mixture was heated to reflux for 24 h. The reaction mixture was cooled and was concentrated. The residue was triturated with water (25 ml), filtered, washed with water, and air dried to a white powder. The powder was triturated with minimum amount of methanol to give 4-hydrazinyl-5-methyl-6-(4-phenylpiperidin-1-yl)pyrimidine (1.7 g, 93%) as a white solid. $^1$H NMR (400 MHz, CHLOROFORM-d) δ 8.37 (s, 1H), 7.42-7.15 (m, 5H), 5.96 (br. s., 1H), 3.74 (d, J=13.1 Hz, 2H), 2.98 (td, J=12.4, 2.5 Hz, 2H), 2.79-2.64 (m, 1H), 1.99 (s, 3H), 1.97-1.79 (m, 4H). LCMS M+1=284.2.

2-Cyclopropyl-N'-(5-methyl-6-(4-phenylpiperidin-1-yl)pyrimidin-4-yl)acetohydrazide A mixture of 2-cyclopropylacetic acid (0.265 g, 2.65 mmol), HATU (1.006 g, 2.65 mmol), and DIPEA (3.53 mmol) in DMF (3 ml) was stirred at room temperature for 10 min. A solution of 4-hydrazinyl-5-methyl-6-(4-phenylpiperidin-1-yl)pyrimidine (0.5 g, 1.764 mmol) in DMF (3 ml) was added to the mixture. The reaction mixture was stirred at room temperature for 2 h, and poured into ice water (30 ml) to give a precipitate that was filtered and air dried to give 2-cyclopropyl-N'-(5-methyl-6-(4-phenylpiperidin-1-yl)pyrimidin-4-yl)acetohydrazide as a white solid (0.3 g, 46.5%). LMCS: Rt=2.32 min, (M−H)$^-$=354, (M+H)$^+$=366.

3-(Cyclopropylmethyl)-8-methyl-7-(4-phenylpiperidin-1-yl)-[1,2,4]triazolo[4,3-c]pyrimidine A mixture of 2-cyclopropyl-N'-(5-methyl-6-(4-phenylpiperidin-1-yl)pyrimidin-4-yl)acetohydrazide (0.06 g, 0.164 mmol) and Burgess' reagent (0.039 g, 0.164 mmol) in THF (3 ml) was heated to reflux for 2 h. The reaction mixture was purified by preparative HPLC on a Phenomenex-Gemini 30×100 mm S10 column using 5-95% water/acetonitrile containing 10 mM ammonium acetate to give 3-(cyclopropylmethyl)-8-methyl-7-(4-phenylpiperidin-1-yl)-[1,2,4]triazolo[4,3-c]pyrimidine (0.03 g, 50%) as a white solid. $^1$H NMR (400 MHz, CHLOROFORM-d) δ 8.82-8.57 (m, 1H), 7.40-7.16 (m, 5H), 3.81-3.59 (m, 2H), 3.18-3.02 (m, 4H), 2.83-2.65 (m, 1H), 2.61-2.45 (m, 3H), 2.03-1.76 (m, 4H), 1.30-1.05 (m, 1H), 0.77-0.57 (m, 2H), 0.44-0.25 (m, 2H). LCMS M+1=348.3.

Example 3

3-(Cyclopropylmethyl)-8-methoxy-7-(4-phenylpiperidin-1-yl)-[1,2,4]triazolo[4,3-c]pyrimidine 4-Hydrazinyl-5-methoxy-6-(4-phenylpiperidin-1-yl)pyrimidine A mixture of 4,6-dichloro-5-methoxypyrimidine (1.0 g, 5.59 mmol), 4-phenylpiperidine (0.937 g, 5.81 mmol), and potassium carbonate (1.621 g, 11.73 mmol) in dioxane (50 ml) was stirred at room temperature for 1 hr and then heated to reflux for 1 h. The mixture was cooled and 35% hydrazine (10.12 ml, 112 mmol) was added. The mixture was heated to reflux for 16 h. The mixture was cooled, diluted with water to give an oil. The oil was suctioned out to give 4-hydrazinyl-5-methoxy-6-(4-phenylpiperidin-1-yl)pyrimidine (1.1 g, 65.8%). LCMS: Rt=2.265 min, 65%, (M+H)$^+$= 300.

2-Cyclopropyl-N'-(5-methoxy-6-(4-phenylpiperidin-1-yl)pyrimidin-4-yl)acetohydrazide A mixture of 4-hydrazinyl-5-methoxy-6-(4-phenylpiperidin-1-yl)pyrimidine (0.50 g, 1.67 mmol) in ethyl acetate (5 ml), THF (10 ml), and saturated sodium bicarbonate (10 ml) was stirred as cyclopropanecarbonyl chloride (1.837 mmol) was added. The mixture was stirred for 16 h. The reaction was cooled. The ethyl acetate layer was separated, washed with water, dried over magnesium sulfate, and concentrated to a crystalline solid (0.30 g, 46%). $^1$H NMR (500 MHz, DMSO-d$_6$) δ 7.92 (s, 1H), 7.38-7.13 (m, 5H), 4.60-4.44 (m, 2H), 3.63 (s, 3H), 3.03-2.87 (m, 2H), 2.85-2.72 (m, 1H), 2.09 (d, J=6.7 Hz, 2H), 1.92-1.79 (m, 2H), 1.77-1.60 (m, 2H), 1.07-0.92 (m, 1H), 0.53-0.41 (m, 2H), 0.26-0.13 (m, 2H)

MS (m+1)=382.2.

3-(Cyclopropylmethyl)-8-methoxy-7-(4-phenylpiperidin-1-yl)-[1,2,4]triazolo[4,3-c]pyrimidine A mixture of 2-cyclopropyl-N'-(5-methoxy-6-(4-phenylpiperidin-1-yl)pyrimidin-4-yl)acetohydrazide (0.30 g, 0.786 mmol) and phosphorus oxychloride (0.11 ml, 1.18 mmol) in acetonitrile (6 ml) was heated to 80° C. for 16 h. The reaction was cooled and quenched with saturated sodium carbonate and stirred for 15 min. The mixture was diluted with ethyl acetate (50 ml) and water. The ethyl acetate layer was separated, washed with water, dried with brine, can concentrated to an amber solid. The solid was dissolved in methylene chloride and applied to a silica gel column. The products were eluted with 0-30% ethyl acetate/methylene chloride. The product fractions were concentrated to give 3-(cyclopropylmethyl)-8-methoxy-7-(4-phenylpiperidin-1-yl)-[1,2,4]triazolo[4,3-c]pyrimidine (8.9 mg, 3.1%). $^1$H NMR (500 MHz, DMSO-$d_6$) δ 9.00 (s, 1H), 7.40-7.25 (m, 5H), 4.26 (d, J=12.8 Hz, 2H), 4.11-3.97 (m, 3H), 3.05 (d, J=6.7 Hz, 4H), 2.86-2.74 (m, 1H), 1.86 (d, J=12.2 Hz, 2H), 1.81-1.65 (m, 2H), 1.29-1.14 (m, 1H), 0.63-0.46 (m, 2H), 0.38-0.21 (m, 2H). MS (m+1)=364.1.

Example 4

3-(Cyclopropylmethyl)-7-(4-phenylpiperidin-1-yl)-8-(trifluoromethyl)-[1,2,4]triazolo[4,3-c]pyrimidine

4-Methoxy-6-(4-phenylpiperidin-1-yl)-5-(trifluoromethyl)pyrimidine

A solution of formamindine acetate (3.68 g, 35.4 mmol) in water (20 ml) and methylene chloride (25 ml) was cooled in an ice bath. The mixture was stirred as 1,3,3,3-tetrafluoro-1-methoxy-2-(trifluoromethyl)prop-1-ene (5, 23.58 mmol) was added and then 50% sodium hydroxide (7.54 g, 94 mmol) was added dropwise. The mixture was stirred for 30 min with ice bath cooling. The methylene chloride layer was separated, washed with 1N HCl, washed with water, dried with brine, and concentrated to give 4-fluoro-6-methoxy-5-(trifluoromethyl)pyrimidine as a clear oil (2.00 g, 43%). The oil was dissolved in dioxane (20 ml) and 4-phenylpiperidine (1.645 g, 10.2 mmol) and potassium carbonate (3 g, 21.71 mmol) were added. The mixture was heated to reflux for 1 hr and then cooled to room temperature. The mixture was diluted with ethyl acetate and water. The ethyl acetate layer was separated, washed with water, washed with 1N HCl, dried with brine, and concentrated to a light yellow oil that solidified upon standing to give 4-methoxy-6-(4-phenylpiperidin-1-yl)-5-(trifluoromethyl)pyrimidine as a yellow solid (2.15 g, 27%). $^1$H NMR (400 MHz, CHLOROFORM-d) δ 8.31 (s, 1H), 7.37-7.30 (m, 2H), 7.26-7.20 (m, 3H), 4.18 (d, J=13.3 Hz, 2H), 4.03 (s, 3H), 3.15 (t, J=12.0 Hz, 2H), 2.78 (tt, J=12.2, 3.7 Hz, 1H), 1.98-1.88 (m, 2H), 1.87-1.72 (m, 2H). $^{19}$F NMR (376 MHz, CHLOROFORM-d) δ-57.20 (s). LCMS: Rt=1.20 min, 93%, (M+H)$^+$=338, 339.

4-Chloro-6-(4-phenylpiperidin-1-yl)-5-(trifluoromethyl)pyrimidine

A solution of 4-methoxy-6-(4-phenylpiperidin-1-yl)-5-(trifluoromethyl)pyrimidine (1.48 g, 4.39 mmol) in phosphorus oxychloride (15 ml) was heated to reflux for 5 h. The solution was cooled and concentrated. The residue was diluted with ethyl acetate/water. The ethyl acetate layer was separated, washed with water, dried with brine, and concentrated. The dark residue dissolved in 50% methylene chloride/hexane and applied to a silica gel column. The column was washed with 25% ethyl acetate/hexane, and the product eluted with 50% ethyl acetate/hexane. The product fractions were concentrated to a clear oil (0.818 g, 54.6%). $^1$H NMR (400 MHz, CHLOROFORM-d) δ 8.36 (s, 1H), 7.36-7.30 (m, 2H), 7.27-7.19 (m, 3H), 4.29 (d, J=13.3 Hz, 2H), 3.22 (td, J=12.9, 1.5 Hz, 2H), 2.83 (tt, J=12.1, 3.7 Hz, 1H), 2.02-1.93 (m, 2H), 1.86-1.72 (m, 2H).

2-Cyclopropyl-N'-(6-(4-phenylpiperidin-1-yl)-5-(trifluoromethyl)pyrimidin-4-yl)acetohydrazide A solution of 4-chloro-6-(4-phenylpiperidin-1-yl)-5-(trifluoromethyl)pyrimidine (0.36 g, 1.053 mmol) and 35% hydrazine in water (1 ml, 11 mmol) in dioxane (10 ml) was stirred for 16 h. The mixture was diluted with ethyl acetate and water. The ethyl acetate layer was separated, washed with water, dried with brine, and partially concentrated. A mixture of the ethyl acetate solution and saturated sodium carbonate (1 ml) was stirred as 2-cyclopropylacetyl chloride (0.15 g, 1.264 mmol) was added. The mixture was stirred for 1 h. The ethyl acetate layer was separated, washed with water, dried with brine, and concentrated to a yellow oil. The material was dissolved in methylene chloride and applied to a silica gel column. The product was eluted with 0-50% ethyl acetate/methylene chloride. The product fractions were concentrated to give 2-cyclopropyl-N'-(6-(4-phenylpiperidin-1-yl)-5-(trifluoromethyl)pyrimidin-4-yl)acetohydrazide as a white powder (0.236 g, 53.4%). $^1$H NMR (400 MHz, CHLOROFORM-d) δ 8.80 (br. s., 1H), 8.19 (s, 1H), 7.64 (br. s., 1H), 7.37-7.29 (m, 2H), 7.26-7.18 (m, 3H), 4.17 (d, J=13.3 Hz, 2H), 3.14 (t, J=12.2 Hz, 2H), 2.77 (tt, J=12.0, 3.8 Hz, 1H), 2.29 (d, J=7.0 Hz, 2H), 1.98-1.88 (m, 2H), 1.86-1.72 (m, 2H), 1.10 (quint, J=7.6, 4.8 Hz, 1H), 0.71-0.63 (m, 2H), 0.33-0.25 (m, 2H). LCMS: Rt=0.92 min, 74%, (M+H)$^+$= 420, 421.

3-(Cyclopropylmethyl)-7-(4-phenylpiperidin-1-yl)-8-(trifluoromethyl)-[1,2,4]triazolo[4,3-c]pyrimidine A solution of 2-cyclopropyl-N'-(6-(4-phenylpiperidin-1-yl)-5-(trifluoromethyl)pyrimidin-4-yl)acetohydrazide (0.236 g, 0.563 mmol), azidotrimethylsilane (0.078 ml, 0.591 mmol), and triphenylphosphine (0.177 g, 0.675 mmol) in methylene chloride (4 ml) was stirred in a cold water bath as 40% DEAD in toluene (0.384 ml, 0.844 mmol) was added. The solution was stirred for 1 h. The reaction was diluted with ethyl acetate and water. The ethyl acetate layer was separated, washed with water, dried with brine, and concentrated to an oil that solidified upon standing. The material was dissolved in methylene chloride and applied to a silica gel column. The product was eluted with 0-75% ethyl acetate/methylene chloride. The product fractions were concentrated to give a clear oil that solidified to a white solid upon standing (0.218 g, 97%). The material was washed with hexane, and then crystallized from ethyl acetate/hexane to give a white powder (92 mg, 38.7%). $^1$H NMR (400 MHz, CHLOROFORM-d) δ 8.62 (s, 1H), 7.39-7.30 (m, 2H), 7.27-7.19 (m, 3H), 4.26 (d, J=13.1 Hz, 2H), 3.31 (t, J=13.1 Hz, 2H), 3.08 (d, J=6.8 Hz, 2H), 2.84 (tt, J=12.2, 3.6 Hz, 1H), 1.98 (d, J=11.0 Hz, 2H), 1.89-1.74 (m, 2H), 1.23-1.11 (m, 1H), 0.75-0.64 (m, 2H), 0.38 (q, J=5.2 Hz, 2H). $^{19}$F NMR (376 MHz, CHLOROFORM-d) δ 56.64 (s). LCMS: Rt=0.94 min, 60%, (M+H)+=402, 403.

Example 5

8-Chloro-3-(cyclopropylmethyl)-7-(4-phenylpiperidin-1-yl)-[1,2,4]triazolo[4,3-b]pyridazine N'-(4-Chloro-5-(4-phenylpiperidin-1-yl)pyridazin-3-yl)-2-cyclopropylacetohydrazide A mixture of 3,4,5-trichloropyridazine (1 g, 5.45 mmol), 4-phenylpiperidine (0.9 g, 5.58 mmol) and potassium carbonate (1.5 g, 10.85 mmol) in acetonitrile (25 ml) was stirred for 4 days. The mixture was diluted with ethyl acetate and water. The ethyl acetate layer was separated, washed with water, dried with brine, and concentrated to a red-brown solid. The solid was dissolved in dioxane (25 ml) and 35% hydrazine (10 ml, 110 mmol) was added. The mixture was heated to reflux for 16 hr overnight. The mixture was diluted with ethyl acetate and water. The ethyl acetate layer was separated, washed twice with water, dried with brine, and separated. The ethyl acetate layer was placed into a 250 ml flask with saturated sodium carbonate (15 ml). A solution of 2-cyclopropylacetyl chloride (freshly prepared from 2-cyclopropylacetic acid (0.600 g, 6.00 mmol) and thionyl chloride) in ethyl acetate (25 ml) was added and the mixture was stirred for 16 h. The mixture was diluted with water and filtered. The solid from the filtration was washed with water and ethyl acetate, and air dried to give N'-(4-chloro-5-(4-phenylpiperidin-1-yl)pyridazin-3-yl)-2-cyclopropylacetohydrazide as a white powder (0.712 g, 33.8%). LCMS: Rt=0.81 min, 95%, (M+H)+=386, 388. $^1$H NMR (400 MHz, DMSO-d6) δ 8.45 (s, 1H), 7.37-7.28 (m, 4H), 7.26-7.19 (m, 1H), 3.72 (d, J=12.3 Hz, 2H), 3.35 (s, 1H), 3.11-2.97 (m, 2H), 2.76 (tt, J=12.1, 3.5 Hz, 1H), 2.12 (d, J=6.8 Hz, 2H), 1.96-1.86 (m, 2H), 1.86-1.72 (m, 2H), 1.11-0.92 (m, 1H), 0.51-0.43 (m, 2H), 0.24-0.17 (m, 2H).

8-Chloro-3-(cyclopropylmethyl)-7-(4-phenylpiperidin-1-yl)-[1,2,4]triazolo[4,3-b]pyridazine A mixture of N'-(4-chloro-5-(4-phenylpiperidin-1-yl)pyridazin-3-yl)-2-cyclopropylacetohydrazide (0.25 g, 0.648 mmol), acetonitrile (3 ml), and phosphorus oxychloride (0.1 ml, 1.073 mmol) was sealed in a microwave vial and heated in a 110° C. oil bath for 16 hr overnight. The solution was quenched with saturated sodium carbonate (1 ml) and stirred for 15 min. The mixture was diluted with ethyl acetate (5 ml) and water. The ethyl acetate layer was separated, washed with water, dried with brine, and concentrated. The residue was washed with ethyl acetate/hexanes, and filtered. The combined filtrates from the ethyl acetate/hexane washes was allowed to concentrate and produced 8-chloro-3-(cyclopropylmethyl)-7-(4-phenylpiperidin-1-yl)-[1,2,4]triazolo[4,3-b]pyridazine as an off-white solid (115 mg, 46.3%). LCMS: Rt=0.98 min, 91%, (M+H)+=368, 370. $^1$H NMR (400 MHz, CHLOROFORM-d) δ 8.24 (s, 1H), 7.42-7.33 (m, 2H), 7.32-7.23 (m, 3H), 3.78 (d, J=12.3 Hz, 2H), 3.20 (td, J=11.8, 3.3 Hz, 2H), 3.10 (d, J=7.0 Hz, 2H), 2.83-2.68 (m, 1H), 2.10-1.91 (m, 4H), 1.38-1.24 (m, 1H), 0.59-0.51 (m, 2H), 0.41-0.32 (m, 2H).

Example 6

3-(Cyclopropylmethyl)-8-methyl-7-(4-phenylpiperidin-1-yl)-[1,2,4]triazolo[4,3-b]pyridazine 4-bromo-5-(4-phenylpiperidin-1-yl)pyridazin-3(2H)-one A mixture of 4,5-dibromopyridazin-3(2H)-one (1.5 g, 5.91 mmol), 4-phenylpiperidine (1.048 g, 6.50 mmol) and DIPEA (3.10 ml, 17.72 mmol) in DMF (20 ml) was stirred at 80° C. under nitrogen overnight. The mixture was poured into ice water (40 ml). The precipitate was collected to give 4-bromo-5-(4-phenylpiperidin-1-yl)pyridazin-3(2H)-one (1.86 g, 85%) as light-yellow solid. $^1$H NMR (500 MHz, CHLOROFORM-d) δ 7.41-7.32 (m, 2H), 7.31-7.23 (m, 3H), 4.05-3.92 (m, 2H), 3.15 (td, J=12.4, 2.4 Hz, 2H), 2.84-2.72 (m, 1H), 2.07-1.99 (m, 2H), 1.99-1.89 (m, 2H). $^1$H NMR (500 MHz, METHANOL-d$_4$) δ 7.34-7.28 (m, 2H), 7.27-7.18 (m, 3H), 4.02-3.91 (m, 2H), 3.15 (td, J=12.4, 2.3 Hz, 2H), 2.82-2.72 (m, 1H), 2.04-1.95 (m, 2H), 1.95-1.84 (m, 2H). LCMS: M+1=335.9.

tert-Butyl 5-bromo-6-oxo-4-(4-phenylpiperidin-1-yl)pyridazine-1(6H)-carboxylate

A solution of 4-bromo-5-(4-phenylpiperidin-1-yl)pyridazin-3(2H)-one (0.5 g, 1.496 mmol), di-tert-butyl dicarbonate (0.521 ml, 2.244 mmol), and triethyl amine (0.417 ml, 2.99 mmol) in dichloromethane (25 ml) was stirred at 30° C. for 16 h. The reaction was diluted with methylene chloride (30 ml), washed with 1M HCl (3×20 ml), aqueous sodium bicarbonate (20 ml), and brine (20 ml). The organic layer was dried over magnesium sulfate, filtered, and concentrated. The residue was triturated with hexane to give tert-butyl 5-bromo-6-oxo-4-(4-phenylpiperidin-1-yl)pyridazine-1(6H)-carboxylate (0.605 g, 88%) as a yellow solid. $^1$H NMR (400 MHz, CHLOROFORM-d) δ 7.63 (s, 1H), 7.39-7.32 (m, 2H), 7.27-7.22 (m, 3H), 4.06-3.94 (m, 2H), 3.24-3.10 (m, 2H), 2.84-2.72 (m, 1H), 2.07-1.98 (m, 2H), 1.97-1.83 (m, 2H), 1.64 (s, 9H). LCMS: M+1=335.9 (—BOC).

tert-Butyl 5-methyl-6-oxo-4-(4-phenylpiperidin-1-yl)pyridazine-1(6H)-carboxylate A suspension of tert-butyl 5-bromo-6-oxo-4-(4-phenylpiperidin-1-yl)pyridazine-1(6H)-carboxylate (0.1 g, 0.230 mmol), trimethylboroxane (0.029 g, 0.230 mmol), cesium carbonate (0.113 g, 0.345 mmol), and [1,1'-bis(diphenylphosphino)ferrocene]dichloropalladium(II) (0.017 g, 0.023 mmol) in dioxane (2 ml) and water (0.1 ml) was heated at 90° C. stirring for 2 h. The reaction was cooled, diluted with DCM, and filtered. The filtrate was concentrated. The residue was purified by silica gel chromatography using 0-40% ethyl acetate/hexane as the eluent give tert-butyl 5-methyl-6-oxo-4-(4-phenylpiperidin-1-yl)pyridazine-1(6H)-carboxylate (46 mg, 51.9%) as off-white solid. $^1$H NMR (400 MHz, CHLOROFORM-d) δ 7.74 (s, 1H), 7.38-7.31 (m, 2H), 7.27-7.22 (m, 3H), 3.58-3.47 (m, 2H), 3.12-3.03 (m, 2H), 2.78-2.67 (m, 1H), 2.12 (s, 3H), 2.03-1.95 (m, 2H), 1.93-1.79 (m, 2H), 1.65 (s, 9H). LCMS M+1=270 (—BOC).

3-Chloro-4-methyl-5-(4-phenylpiperidin-1-yl)pyridazine

A mixture of tert-butyl 5-methyl-6-oxo-4-(4-phenylpiperidin-1-yl)pyridazine-1(6H)-carboxylate (0.78 g, 2.111 mmol) in phosphorus oxychloride (9.84 ml, 106 mmol) was heated at 90° C. under nitrogen for 1 h and then concentrated. The residue was dissolved in ethyl acetate and ice cold aqueous sodium bicarbonate. The aqueous layer was separated and extracted with ethyl acetate (3×20 ml). The combined ethyl acetate layers were washed with aqueous sodium bicarbonate (2×20 ml) and brine (20 ml), and dried over magnesium sulfate. The residue was triturated to give 3-chloro-4-methyl-5-(4-phenylpiperidin-1-yl)pyridazine (0.55 g, 77%) as light-brown solid. $^1$H NMR (400 MHz, CHLOROFORM-d) δ 8.78 (s, 1H), 7.39-7.32 (m, 2H), 7.29-7.26 (m, 3H), 3.56-3.44 (m, 2H), 3.04 (td, J=12.3, 2.5 Hz, 2H), 2.81-2.69 (m, 1H), 2.36 (s, 3H), 2.08-2.00 (m, 2H), 1.98-1.84 (m, 2H). LCMS: M+1=288.0.

3-Hydrazinyl-4-methyl-5-(4-phenylpiperidin-1-yl) pyridazine

A mixture of 3-chloro-4-methyl-5-(4-phenylpiperidin-1-yl)pyridazine (0.75 g, 2.61 mmol) and hydrazine hydrate (1.636 ml, 52.1 mmol) in dioxane (15 ml) was stirred at 90° C. for 3 days. The reaction mixture was concentrated and the residue was triturated with water to give the crude product which was dried and was then triturated with minimum amount of methanol to give 3-hydrazinyl-4-methyl-5-(4-phenylpiperidin-1-yl)pyridazine (0.55 g, 70%) as light-brown solid. $^1$H NMR (400 MHz, CHLOROFORM-d) δ 8.53 (s, 1H), 7.39-7.32 (m, 2H), 7.29-7.25 (m, 3H), 5.54 (br. s., 1H), 4.21 (br. s., 2H), 3.43-3.31 (m, 2H), 2.98 (td, J=11.9, 2.5 Hz, 2H), 2.76-2.64 (m, 1H), 2.05 (s, 3H), 2.02-1.97 (m, 2H), 1.95-1.84 (m, 2H). LCMS: M+1=284.0.

2-Cyclopropyl-N'-(4-methyl-5-(4-phenylpiperidin-1-yl)pyridazin-3-yl)acetohydrazide A suspension of 3-hydrazinyl-4-methyl-5-(4-phenylpiperidin-1-yl)pyridazine (0.4 g, 1.412 mmol) in ethyl acetate (10 ml) and THF (3 ml) and saturated aqueous sodium carbonate (5 ml) was stirred as 20% 2-cyclopropylacetyl chloride in ethyl acetate (1.255 ml, 2.117 mmol) was added. The mixture was stirred at for 10 min and then concentrated. The residue was washed with water and the crude product was filtered. The crude solid was dried and was then sonicated in minimum amount of methanol and collected by filtering to get 2-cyclopropyl-N'-(4-methyl-5-(4-phenylpiperidin-1-yl)pyridazin-3-yl)acetohydrazide (0.3 g, 57%) as light-brown solid. $^1$H NMR (400 MHz, CHLOROFORM-d) δ 9.90 (br s, 1H), 8.53 (s, 1H), 7.39-7.33 (m, 2H), 7.29-7.24 (m, 3H), 7.21 (s, 1H), 3.42 (d, J=12.0 Hz, 2H), 2.99 (td, J=12.0, 2.6 Hz, 2H), 2.79-2.64 (m, 1H), 2.30 (d, J=7.0 Hz, 2H), 2.04-1.97 (m, 2H), 1.93 (td, J=12.2, 3.4 Hz, 2H), 1.18-1.08 (m, 1H), 0.67-0.60 (m, 2H), 0.28 (d, J=5.8 Hz, 2H). LCMS: M+1=366.1.

3-(Cyclopropylmethyl)-8-methyl-7-(4-phenylpiperidin-1-yl)-[1,2,4]triazolo[4,3-b]pyridazine A solution of 2-cyclopropyl-N'-(4-methyl-5-(4-phenylpiperidin-1-yl)pyridazin-3-yl)acetohydrazide (300 mg, 0.821 mmol) and triphenylphosphine (323 mg, 1.231 mmol) in methylene chloride (10 ml) and THF (3 ml) was stirred at room temperature as azidotrimethylsilane (0.142 ml, 1.067 mmol) was added, followed by the dropwise addition of 40% DEAD in toluene (0.561 ml, 1.231 mmol). The resulting mixture was stirred at for 10 min. The mixture was concentrated and the residue was purified by silica gel chromatography using 0-10% 2M ammonia in methanol/ ethyl acetate to give 165 mg which was further purified by preparative HPLC on a Xbridge OBD preparative Shield RP18 19×105 5 um column to give 3-(cyclopropylmethyl)-8-methyl-7-(4-phenylpiperidin-1-yl)-[1,2,4]triazolo[4,3-b] pyridazine (120 mg, 41.7%) as an off-white solid. $^1$H NMR (400 MHz, CHLOROFORM-d) δ 8.26 (s, 1H), 7.40-7.33 (m, 2H), 7.32-7.24 (m, 3H), 3.41-3.33 (m, 2H), 3.11 (d, J=6.8 Hz, 2H), 3.10-3.04 (m, J=3.0 Hz, 2H), 2.77-2.67 (m, 1H), 2.65 (s, 3H), 2.08-1.90 (m, 4H), 1.40-1.23 (m, 1H), 0.62-0.49 (m, 2H), 0.42-0.30 (m, 2H). LCMS: M+1=348.0.

Example 7

3-(Cyclopropylmethyl)-7-(4-phenylpiperidin-1-yl)-8-(trifluoromethyl)-[1,2,4]triazolo[4,3-b]pyridazine 4-Bromo-5-(4-phenylpiperidin-1-yl)pyridazin-3(2H)-one A solution of 4,5-dibromopyridazin-3(2H)-one (5.0 g, 19.69 mmol), 4-phenylpiperidine (3.49 g, 21.66 mmol), and DIPEA (7.57 ml, 43.3 mmol) in DMA (41.6 ml) was heated to 100° C. for 16 h. The reaction was cooled and diluted with saturated sodium bicarbonate to give 4-bromo-5-(4-phenylpiperidin-1-yl)pyridazin-3(2H)-one as a precipitate that was filtered and dried (6.46 g, 98%). LCMS: Rt=0.91 min, (M+H)$^+$=336.0. The material was used without purification.

tert-Butyl 5-bromo-6-oxo-4-(4-phenylpiperidin-1-yl) pyridazine-1(6H)-carboxylate A solution of 4-bromo-5-(4-phenylpiperidin-1-yl) pyridazin-3(2H)-one (0.50 g, 1.496 mmol), di-tert-butyl dicarbonate (0.417 ml, 1.795 mmol), and triethylamine (0.313 ml, 2.244 mmol) in methylene chloride (50 ml) was stirred for 16 h. The solution was washed with water. The methylene chloride layer was dried over magnesium sulfate, and concentrated to give tert-butyl 5-bromo-6-oxo-4-(4-phenylpiperidin-1-yl)pyridazine-1(6H)-carboxylate as a yellow semisolid (0.561 g, 86%). The material was used without purification.

tert-Butyl 6-oxo-4-(4-phenylpiperidin-1-yl)-5-(trifluoromethyl)pyridazine-1(6H)-carboxylate A mixture of tert-butyl 5-bromo-6-oxo-4-(4-phenylpiperidin-1-yl)pyridazine-1(6H)-carboxylate (0.250 g, 0.576 mmol) and copper(I) iodide (0.219 g, 1.151 mmol) in DMF (5.28 ml) was stirred as methyl 2,2-difluoro-2-(fluorosulfonyl)acetate (0.146 ml, 1.151 mmol) was added. The mixture was heated to 100° C. for 16 h. An additional aliquot of methyl 2,2-difluoro-2-(fluorosulfonyl)acetate (0.146 ml, 1.151 mmol) added and the reaction was allowed to continue to heat for another 4 h. The reaction was filtered through silica with ethyl acetate. The filtrate was washed with saturated sodium bicarbonate and ammonium chloride. The organic layers were combined and concentrated to give tert-butyl 6-oxo-4-(4-phenylpiperidin-1-yl)-5-(trifluoromethyl)pyridazine-1(6H)-carboxylate as an oil. LCMS: Rt=0.95 min, (M+H)$^+$=324.2. The material was used without purification.

3-Chloro-5-(4-phenylpiperidin-1-yl)-4-(trifluoromethyl)pyridazine

A solution of tert-butyl 6-oxo-4-(4-phenylpiperidin-1-yl)-5-(trifluoromethyl)pyridazine-1(6H)-carboxylate (0.250 g, 0.590 mmol) in phosphorus oxychloride (4 ml) was heated to 100° C. for 1 h. The reaction was concentrated and the residue as dissolved in methylene chloride, washed with saturated sodium bicarbonate, dried over magnesium sulfate, and concentrated to give 3-chloro-5-(4-phenylpiperidin-1-yl)-4-(trifluoromethyl)pyridazine (0.220 g, 100%) as a brown oil. $^1$H NMR (500 MHz, METHANOL-$d_4$) δ 9.16 (s, 1H), 7.37-7.10 (m, 6H), 4.43 (s, 1H), 4.22-4.09 (m, 1H), 3.64 (t, J=13.6 Hz, 1H), 3.25-3.14 (m, 1H), 2.14-1.87 (m, 4H). HPLC: Rt=1.08 min, LCMS: Rt=1.08 min, (M+H)$^+$= 342.1. The material was used without purification.

3-Hydrazinyl-5-(4-phenylpiperidin-1-yl)-4-(trifluoromethyl)pyridazine

A mixture of 3-chloro-5-(4-phenylpiperidin-1-yl)-4-(trifluoromethyl)pyridazine (0.220 g, 0.644 mmol), potassium carbonate (0.187 g, 1.352 mmol), and 35% hydrazine (1.166 ml, 12.87 mmol) in dioxane (10 ml) heated to 100° C. for 3 h. The mixture was cooled, diluted with water and extracted with ethyl acetate. The organic layers were combined and concentrated. LCMS: Rt=0.81 min, (M+H)$^+$=338.2. The material was used without purification.

2-Cyclopropyl-N'-(5-(4-phenylpiperidin-1-yl)-4-(trifluoromethyl)pyridazin-3-yl)acetohydrazide A solution of 2-cyclopropylacetyl chloride (0.085 g, 0.717 mmol) in ethyl acetate (2.5 ml) was added to a solution of 3-hydrazinyl-5-(4-phenylpiperidin-1-yl)-4-(trifluoromethyl)pyridazine (0.22 g, 0.652 mmol) in ethyl acetate (2.5 ml), THF (5.00 ml), and saturated sodium bicarbonate (5 ml) and was stirred for 16 h. The reaction was diluted with ethyl acetate and saturated sodium bicarbonate. The organic layer was washed with saturated sodium bicarbonate and concentrated to give 2-cyclopropyl-N'-(5-(4-phenylpiperidin-1-yl)-4-(trifluoromethyl)pyridazin-3-yl)acetohydrazide as a brown oil. LCMS: Rt=0.84 min, (M+H)$^+$=420.2. The material was used without purification.

3-(Cyclopropylmethyl)-7-(4-phenylpiperidin-1-yl)-8-(trifluoromethyl)-[1,2,4]triazolo[4,3-b]pyridazine A solution of 2-cyclopropyl-N'-(5-(4-phenylpiperidin-1-yl)-4-(trifluoromethyl)pyridazin-3-yl)acetohydrazide (0.275 g, 0.656 mmol), triphenylphosphine (0.206 g, 0.787 mmol), and azidotrimethylsilane (0.174 ml, 1.311 mmol) in methylene chloride (4 ml) was stirred in a cool water bath as 40% DEAD in toluene (0.896 ml, 1.967 mmol) was added. Effervescence occurred. The reaction mixture was applied to a silica gel column and the product flushed through with methylene chloride. The fractions were concentrated to a yellow oil. The oil was purified by prep-HPLC using an XBridge OBD 19×100 mm 5 uM column, and 30-95% water/acetonitrile containing 10 mM ammonium acetate as the eluent. The product fractions were concentrated, and the product extracted in to ethyl acetate. The extract was concentrated to give 3-(cyclopropylmethyl)-7-(4-phenylpiperidin-1-yl)-8-(trifluoromethyl)-[1,2,4]triazolo[4,3-b]pyridazine (7.6 mg, 2.86%) as a yellow solid. $^1$H NMR (500 MHz, METHANOL-$d_4$) δ 8.69 (s, 1H), 7.42-7.16 (m, 5H), 3.88 (d, J=13.1 Hz, 2H), 3.56-3.41 (m, 2H), 3.05 (d, J=7.0 Hz, 2H), 2.94-2.79 (m, 1H), 2.00-1.89 (m, 5H), 0.67-0.52 (m, 2H), 0.44-0.26 (m, 2H). LCMS: RT=0.96 min, (M+H)$^+$= 402.2.

Example 8

7-(4-Benzylpiperidin-1-yl)-8-chloro-3-(cyclopropylmethyl)-[1,2,4]triazolo[4,3-c]pyrimidine

4-(4-Benzylpiperidin-1-yl)-6-chloropyrimidine

A mixture of 4,6-dichloropyrimidine (3 g, 20.14 mmol), 4-benzylpiperidine (3.7 g, 21.11 mmol), and potassium carbonate (5 g, 36.2 mmol) in acetonitrile (50 ml) was heated to reflux for 16 hr overnight. The mixture was filtered and the filtrate was concentrated. The residue was dissolved in methylene chloride and applied to a silica gel column. The product was eluted with 0-20% ethyl acetate/methylene chloride. The product fractions were concentrated to give 4-(4-benzylpiperidin-1-yl)-6-chloropyrimidine as an off white solid (4.03 g, 69.5%). LCMS: Rt=1.09, 44%, (M+H)$^+$= 288, 290. $^1$H NMR (400 MHz, CHLOROFORM-d) δ 8.35 (d, J=0.8 Hz, 1H), 7.34-7.28 (m, 2H), 7.26-7.20 (m, 1H), 7.15 (d, J=6.8 Hz, 2H), 6.49 (d, J=0.8 Hz, 1H), 4.37 (br. s., 1H), 2.86 (td, J=12.9, 2.4 Hz, 2H), 2.57 (d, J=7.0 Hz, 2H), 1.93-1.81 (m, 1H), 1.82-1.74 (m, 1H), 1.75 (s, 1H), 1.79 (s, 1H), 1.26-1.16 (m, 2H).

4-(4-Benzylpiperidin-1-yl)-6-hydrazinylpyrimidine

A solution of 4-(4-benzylpiperidin-1-yl)-6-chloropyrimidine (4.03 g, 14.00 mmol) and 35% hydrazine (38.0 ml, 420 mmol) in dioxane (60 ml) was heated to reflux for 16 h. The solution was cooled and concentrated. The residue was dissolved in ethyl acetate/water. The ethyl acetate layer was washed with water, dried with brine, and concentrated to give 4-(4-benzylpiperidin-1-yl)-6-hydrazinylpyrimidine as an off-white solid (3.64 g, 92%). $^1$H NMR (400 MHz, CHLOROFORM-d) δ 8.17 (d, J=1.0 Hz, 1H), 7.35-7.28 (m, 2H), 7.26-7.19 (m, 1H), 7.16 (d, J=6.8 Hz, 2H), 5.90 (br. s., 1H), 5.87 (d, J=0.8 Hz, 1H), 4.36 (d, J=13.3 Hz, 2H), 3.70 (br. s., 2H), 2.80 (td, J=12.9, 2.6 Hz, 2H), 2.57 (d, J=7.3 Hz, 2H), 1.90-1.78 (m, 1H), 1.74 (d, J=13.6 Hz, 2H), 1.63 (br. s., 1H), 1.25 (qd, J=12.3, 4.1 Hz, 2H).

N'-(6-(4-Benzylpiperidin-1-yl)pyrimidin-4-yl)-2-cyclopropylacetohydrazide

A solution of 2-cyclopropylacetic acid (1.415 g, 14.13 mmol) and CDI (2.291 g, 14.13 mmol) in ethyl acetate (30 ml) was stirred for 30 min at rt, and then added to a solution of 4-(4-benzylpiperidin-1-yl)-6-hydrazinyl pyrimidine (3.64 g, 12.85 mmol) in THF (30 ml). The solution was heated to reflux for 16 h. The brown solution was cooled to give a fluffy precipitate which was filtered, washed with hexanes, and air dried. The filtrate was concentrated. The precipitate and the filtrate were combined, and recrystallized from isopropanol to give N'-(6-(4-benzylpiperidin-1-yl)pyrimidin-4-yl)-2-cyclopropylacetohydrazide as a light pink powder (3.33 g, 70.9%). $^1$H NMR (400 MHz, CHLOROFORM-d) δ 8.28-8.15 (m, 1H), 7.92 (br. s., 1H), 7.36-7.28 (m, 2H), 7.26-7.19 (m, 1H), 7.16 (d, J=6.8 Hz, 2H), 7.10 (d, J=15.8 Hz, 1H), 5.80-5.67 (m, 1H), 4.28 (s, 1H), 4.31 (s, 1H), 2.86-2.71 (m, 1H), 2.56 (d, J=7.3 Hz, 2H), 2.37-2.24 (m, 2H), 1.91-1.76 (m, 1H), 1.76-1.56 (m, 3H), 1.30-1.15 (m, 3H), 1.15-1.01 (m, 1H), 0.71-0.63 (m, 1H), 0.32-0.24 (m, 1H), 0.14 (q, J=4.9 Hz, 1H). LCMS: Rt=0.84 min, 66%, (M+H)$^+$=366, 367.

N'-(6-(4-Benzylpiperidin-1-yl)-5-chloropyrimidin-4-yl)-2-cyclopropylacetohydrazide A solution of N'-(6-(4-benzylpiperidin-1-yl)pyrimidin-4-yl)-2-cyclopropylacetohydrazide (0.25 g, 0.684 mmol) and NCS (0.137 g, 1.026 mmol) in methylene chloride (5 ml) was stirred in a warm water bath for 16 h. The brown solution was diluted with ethyl acetate and sat'd sodium bisulfate. The ethyl acetate layer was separated, washed with water, dried with brine, and concentrated. The residue was dissolved in methylene chloride and applied to a silica gel column. The product was eluted with 0-100% ethyl acetate/methylene chloride. The product fractions were concentrated to give a red oil (103 mg, 37.7%) that solidified to a red foam upon concentration from methylene chloride. $^1$H NMR (400 MHz, CHLOROFORM-d) δ 8.86 (d, J=3.5 Hz, 1H), 8.21-8.20 (m, 1H), 8.15 (s, 1H), 7.64 (d, J=3.3 Hz, 1H), 7.33-7.28 (m, 2H), 7.25-7.19 (m, 1H), 7.18-7.13 (m, 2H), 4.21 (d, J=13.1 Hz, 2H), 2.84 (td, J=12.7, 2.0 Hz, 2H), 2.58 (d, J=7.0 Hz, 2H), 2.27 (d, J=7.3 Hz, 2H), 1.91 (br. s., 1H), 1.85-1.67 (m, 3H), 1.44-1.30 (m, 2H), 1.09 (quint, J=7.5, 4.9 Hz, 1H), 0.67-0.60 (m, 2H), 0.30-0.22 (m, 2H). LCMS: Rt=0.94 min, 82%, (M+H)$^+$=400, 402.

7-(4-Benzylpiperidin-1-yl)-8-chloro-3-(cyclopropylmethyl)-[1,2,4]triazolo[4,3-c]pyrimidine A suspension of N'-(6-(4-benzylpiperidin-1-yl)-5-chloropyrimidin-4-yl)-2-cyclopropylacetohydrazide (0.103 g, 0.258 mmol), TMS-N3 (0.036 ml, 0.270 mmol), and triphenylphosphine (0.081 g, 0.309 mmol) in THF (3 ml) was stirred as 40% DEAD in toluene (0.176 ml, 0.386 mmol) was added by syringe to give a red solution. The solution was stirred 2 days at room temperature. The red solution was diluted with ethyl acetate and water. The ethyl acetate layer was separated, washed with water, dried with brine, and concentrated to a red film. The material was dissolved in methylene chloride and applied to a silica gel column. The product was eluted with 0-100% ethyl acetate/methylene chloride. The product fractions were concentrated to give a clear oil that solidified upon standing to give 7-(4-benzylpiperidin-1-yl)-8-chloro-3-(cyclopropylmethyl)-[1,2,4]triazolo[4,3-c]pyrimidine as a white solid (19.6 mg, 19.1%). $^1$H NMR (400 MHz, CHLOROFORM-d) δ 8.60 (s, 1H), 7.84-7.75 (m, 1H), 7.72-7.63 (m, 1H), 7.59-7.52 (m, 1H), 7.51-7.43 (m, 1H), 7.35-7.28 (m, 2H), 7.26-7.19 (m, 1H), 7.19-7.13 (m, 2H), 4.22-4.12 (m, 2H), 3.07 (d, J=6.8 Hz, 2H), 2.96 (td, J=12.7, 2.0 Hz, 2H), 2.60 (d, J=6.8 Hz, 2H), 1.96 (br. s., 1H), 1.86-1.71 (m, 3H), 1.48-1.33 (m, 2H), 1.15 (tddd, J=9.9, 4.9, 3.1, 1.9 Hz, 1H), 0.69-0.62 (m, 2H), 0.38-0.32 (m, 2H). LCMS: Rt=0.96 min, 88%, (M+H)$^+$=382, 384.

Example 9

Trans-8-chloro-3-(cyclopropylmethyl)-N-((2-(4-fluorophenyl)cyclopropyl)methyl)-[1,2,4]triazolo[4,3-b]pyridazin-7-amine 5,6-Dichloro-N-((2-(4-fluorophenyl)cyclopropyl)methyl)pyridazin-4-amine A mixture of 3,4,5-trichloropyridazine (0.50 g, 2.73 mmol), racemic (2-(4-fluorophenyl)cyclopropyl)methanamine hydrochloride (0.550 g, 2.73 mmol) and potassium carbonate (0.753 g, 5.45 mmol) in acetonitrile (10 ml) was stirred for 2 days. The mixture was filtered and the filtrated was concentrated to give 5,6-dichloro-N-((2-(4-fluorophenyl)cyclopropyl)methyl)pyridazin-4-amine as a red oil (0.766 g, 90%) LCMS: Rt=2.44 min, 80%, (M−H)$^-$=311, (M+H)$^+$=313.

5-Chloro-N-((2-(4-fluorophenyl)cyclopropyl)methyl)-6-hydrazinylpyridazin-4-amine A solution of 5,6-dichloro-N-((2-(4-fluorophenyl)cyclopropyl)methyl)pyridazin-4-amine (0.766 g, 2.454 mmol) and 35% hydrazine (4.40 ml, 49.1 mmol) in dioxane (10 ml) was heated to reflux for 16 h. The reaction was diluted with ethyl acetate and water. The ethyl acetate layer was washed with water, dried over magnesium sulfate, and concentrated to give 5-chloro-N-((2-(4-fluorophenyl)cyclopropyl)methyl)-6-hydrazinylpyridazin-4-amine an orange oil (0.56 g, 74%) that was used without purification.

N'-(4-Chloro-5-(((2-(4-fluorophenyl)cyclopropyl)methyl)amino)pyridazin-3-yl)-2-cyclopropylacetohydrazide A solution of thionyl chloride (0.296 ml, 4.06 mmol) and 2-cyclopropylacetic acid (0.089 g, 0.894 mmol) in methylene chloride (2.5 ml) was heated to reflux for 1 h and then concentrated. The residue was dissolved in ethyl acetate (2.5 ml) and added to a mixture of 5-chloro-N-((2-(4-fluorophenyl)cyclopropyl)methyl)-6-hydrazinylpyridazin-4-amine (0.250 g, 0.812 mmol) in ethyl acetate (2.5 ml), THF (5.00 ml), and saturated sodium bicarbonate (5 ml). The mixture was stirred at room temperature for 16 h. The reaction was diluted with ethyl acetate and water. The ethyl acetate layer were washed with water, dried over magnesium sulfate, and concentrated to give N'-(4-chloro-5-(((2-(4-fluorophenyl)cyclopropyl)methyl)amino) pyridazin-3-yl)-2-cyclopropylacetohydrazide as a brown oil (0.281 g, 89%). LCMS: Rt=2.30 min, 92%, (M−H)$^-$=388, (M+H)$^+$=390.

Trans-8-chloro-3-(cyclopropylmethyl)-N-((2-(4-fluorophenyl)cyclopropyl)methyl)-[1,2,4]triazolo[4,3-b]pyridazin-7-amine A solution of N'-(4-chloro-5-(((2-(4-fluorophenyl)cyclopropyl)methyl)amino) pyridazin-3-yl)-2-cyclopropylacetohydrazide (0.281 g, 0.721 mmol) and phosphorus oxychloride (0.1 ml, 1.08 mmol) in acetonitrile (6 ml) was heated to 80° C. for 16 h. The reaction was cooled and quenched with saturated sodium carbonate. The mixture was diluted with ethyl acetate and water. The ethyl acetate layer was washed with water, dried with brine, and concentrated to a brown oil. The crude material was purified by prep-HPLC to give 8-chloro-3-(cyclopropylmethyl)-N-((2-(4-fluorophenyl)cyclopropyl)methyl)-[1,2,4]triazolo[4,3-b]pyridazin-7-amine (93 mg, 33.7%). $^1$H NMR (500 MHz, DMSO-d$_6$) δ 8.69 (s, 1H), 7.18-6.96 (m, 4H), 6.76 (t, J=6.4 Hz, 1H), 3.63-3.40 (m, 2H), 2.95 (d, J=7.0 Hz, 2H), 1.98 (dt, J=8.9, 4.7 Hz, 1H), 1.50-1.33 (m, 1H), 1.28-1.13 (m, 1H), 1.02 (dt, J=8.7, 5.1 Hz, 1H), 0.95-0.86 (m, 1H), 0.55-0.43 (m, 2H), 0.33-0.19 (m, 2H). MS (m+1)=372.1.

Example 10

8-Chloro-3-(cyclopropylmethyl)-N-(((1R,2R)-2-(4-fluorophenyl)cyclopropyl)methyl)-[1,2,4]triazolo[4,3-b]pyridazin-7-amine Racemic trans-8-chloro-3-(cyclopropylmethyl)-N-((2-(4-fluorophenyl)cyclopropyl)methyl)-[1,2,4]triazolo[4,3-b]pyridazin-7-amine was separated by chiral SFC HPLC on ChiralPak AS-H, 30×250 mm, 5 µm, column using 20% methanol containing 0.1% DEA/80% CO$_2$ as the eluent, at 120 bar, and 35° C., with a flow rate of 70 ml/min, and the UV detector at 225 nm. Enantiomer 1 was collected at 9.75-11.80 min (8.5 mg).

Example 11

8-Chloro-3-(cyclopropylmethyl)-N-(((1S,2S)-2-(4-fluorophenyl)cyclopropyl)methyl)-[1,2,4]triazolo[4,3-b]pyridazin-7-amine Racemic trans-8-chloro-3-(cyclopropylmethyl)-N-((2-(4-fluorophenyl)cyclopropyl)methyl)-[1,2,4]triazolo[4,3-b]pyridazin-7-amine was separated by chiral SFC HPLC on ChiralPak AS-H, 30×250 mm, 5 μm, column using 20% methanol containing 0.1% DEA/80% $CO_2$ as the eluent, at 120 bar, and 35° C., with a flow rate of 70 ml/min, and the UV detector at 225 nm. Enantiomer 2 was collected at 12.80-15.00 min (11.6 mg).

Example 12

3-(Cyclopropylmethyl)-7-(4-(4-fluorophenyl)piperidin-1-yl)-8-methoxy-[1,2,4]triazolo[4,3-c]pyrimidine 4-(4-(Fluorophenyl)piperidin-1-yl)-6-hydrazinyl-5-methoxypyrimidine. A mixture of 4,6-dichloro-5-methoxypyrimidine (0.50 g, 2.79 mmol), 4-(4-fluorophenyl)piperidine (0.521 g, 2.90 mmol), and potassium carbonate (0.811 g, 5.87 mmol) in dioxane (10 ml) was stirred at room temperature for 1 hr and then heated to reflux for 1 h. The mixture was cooled and 35% hydrazine (5.06 ml, 55.9 mmol) was added. The mixture was heated to reflux for 16 hr overnight. The reaction was partitioned between ethyl acetate and water. The ethyl acetate layer was washed with water, dried with magnesium sulfate, and concentrated to give a yellow oil (0.88 g, 100%). LCMS: Rt=0.79 min, 50%, $(M+H)^+$=318. The material was used without purification.

2-Cyclopropyl-N'-(6-(4-(4-fluorophenyl)piperidin-1-yl)-5-methoxypyrimidin-4-yl)acetohydrazide A solution of 2-cyclopropylacetic acid (0.081 ml, 0.867 mmol) and thionyl chloride (0.287 ml, 3.94 mmol) in methylene chloride (2.5 ml) was heated to reflux for 1 h then concentrated. A solution of the residue in ethyl acetate (2.5 ml) was added to a solution of 4-(4-(4-fluorophenyl)piperidin-1-yl)-6-hydrazinyl-5-methoxypyrimidine (0.25 g, 0.788 mmol) in ethyl acetate (2.5 ml), THF (5.00 ml), and saturated sodium bicarbonate (5 ml). The mixture was stirred at room temperature for 16 h. The reaction was diluted with ethyl acetate and water. The ethyl acetate layer were washed with water and concentrated to give 2-cyclopropyl-N'-(6-(4-(4-fluorophenyl)piperidin-1-yl)-5-methoxypyrimidin-4-yl)acetohydrazide (0.315 g, 100%). LCMS: Rt=2.46 min, 95%, $(M-H)^-$=398, $(M+H)^+$=400. The material was used without purification.

3-(Cyclopropylmethyl)-7-(4-(4-fluorophenyl)piperidin-1-yl)-8-methoxy-[1,2,4]triazolo[4,3-c]pyrimidine A solution of 2-cyclopropyl-N'-(6-(4-(4-fluorophenyl)piperidin-1-yl)-5-methoxypyrimidin-4-yl)acetohydrazide (0.315 g, 0.789 mmol) and phosphorus oxychloride (0.11 ml, 1.183 mmol) in acetonitrile (6 ml) heated to 80° C. for 16 h. The reaction was cooled and quenched with saturated sodium carbonate. The mixture was diluted with ethyl acetate and water. The ethyl acetate layer was separated and concentrated to an oil that was purified by preparative HPLC to give 3-(cyclopropylmethyl)-7-(4-(4-fluorophenyl)piperidin-1-yl)-8-methoxy-[1,2,4]triazolo[4,3-c]pyrimidine (5.1 mg, 1.6%). $^1$H NMR (500 MHz, DMSO-$d_6$) δ 9.00 (s, 1H), 7.32 (dd, J=8.5, 5.8 Hz, 2H), 7.13 (t, J=8.9 Hz, 2H), 4.25 (d, J=12.8 Hz, 2H), 4.05 (s, 3H), 3.13-2.94 (m, 4H), 2.88-2.75 (m, 1H), 1.85 (d, J=11.0 Hz, 2H), 1.79-1.63 (m, 2H), 1.30-1.14 (m, 1H), 0.59-0.48 (m, 2H), 0.31 (d, J=5.2 Hz, 2H). MS (m+1)=382.2.

Example 13

7-(4-(4-Fluorophenyl)piperidin-1-yl)-8-methoxy-3-neopentyl-[1,2,4]triazolo[4,3-c]pyrimidine N'-(6-(4-(4-Fluorophenyl)piperidin-1-yl)-5-methoxypyrimidin-4-yl)-3,3-dimethylbutanehydrazide A solution of thionyl chloride (0.287 ml, 3.94 mmol) and 3,3-dimethylbutanoic acid (0.111 ml, 0.867 mmol) in methylene chloride (2.5 ml) was heated to reflux for 1 h then concentrated. A solution of the residue in ethyl acetate (2.5 ml) was added to a mixture of 4-(4-(4-fluorophenyl)piperidin-1-yl)-6-hydrazinyl-5-methoxypyrimidine (0.25 g, 0.788 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to a resin. LCMS: Rt=2.38 min, 91%, $(M-H)^-$=414, $(M+H)^+$=416. The material was used without purification, assuming 100%.

7-(4-(4-Fluorophenyl)piperidin-1-yl)-8-methoxy-3-neopentyl-[1,2,4]triazolo[4,3-c]pyrimidine A solution of N'-(6-(4-(4-fluorophenyl)piperidin-1-yl)-5-methoxypyrimidin-4-yl)-3,3-dimethylbutanehydrazide (0.315 g, 0.758 mmol) and phosphorus oxychloride (0.106 ml, 1.137 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil. The crude material was purified by preparative HPLC to give 7-(4-(4-fluorophenyl)piperidin-1-yl)-8-methoxy-3-neopentyl-[1,2,4]triazolo[4,3-c]pyrimidine (9.1 mg, 2.9%). $^1$H NMR (500 MHz, DMSO-$d_6$) δ 9.09 (s, 1H), 7.33 (dd, J=8.5, 5.5 Hz, 2H), 7.13 (t, J=8.9 Hz, 2H), 4.25 (d, J=12.8 Hz, 2H), 4.06 (s, 3H), 3.08-2.99 (m, 4H), 2.87-2.74 (m, 1H), 1.92-1.81 (m, 2H), 1.78-1.66 (m, 2H), 1.09-0.96 (m, 9H). MS (m+1)=398.2.

Example 14

1-(3-(Cyclopropylmethyl)-8-methoxy-[1,2,4]triazolo[4,3-c]pyrimidin-7-yl)-4-(4-fluorophenyl)piperidin-4-ol 2-Cyclopropyl-N'-(6-(4-(4-fluorophenyl)-4-hydroxypiperidin-1-yl)-5-methoxypyrimidin-4-yl)acetohydrazide A solution of thionyl chloride (0.274 ml, 3.75 mmol) and 2-cyclopropylacetic acid (0.077 ml, 0.825 mmol) in methylene chloride (2.5 ml) was heated to reflux for 1 h and then concentrated. A solution of the residue ethyl acetate (2.5 ml) was added to a solution of 93536-042 (0.25 g, 0.75 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give 2-cyclopropyl-N'-(6-(4-(4-fluorophenyl)-4-hydroxypiperidin-1-yl)-5-methoxypyrimidin-4-yl)acetohydrazide. The material was used without purification, assuming 100%. LCMS: Rt=2.143 min, 96%, (M−H)¯= 414, (M+H)⁺=416.

1-(3-(Cyclopropylmethyl)-8-methoxy-[1,2,4]triazolo[4,3-c]pyrimidin-7-yl)-4-(4-fluorophenyl)piperidin-4-ol A solution of 2-cyclopropyl-N'-(6-(4-(4-fluorophenyl)-4-hydroxypiperidin-1-yl)-5-methoxypyrimidin-4-yl)acetohydrazide (0.315 g, 0.758 mmol) and phosphorus oxychloride (0.106 ml, 1.137 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil that was purified by preparative HPLC to give 1-(3-(cyclopropylmethyl)-8-methoxy-[1,2,4]triazolo[4,3-c]pyrimidin-7-yl)-4-(4-fluorophenyl)piperidin-4-ol (0.8 mg, 0.3%). $^1$H NMR (500 MHz, METHANOL-d$_4$) δ 8.86 (s, 1H), 7.59-7.47 (m, 2H), 7.06 (t, J=8.9 Hz, 2H), 4.28 (d, J=13.1 Hz, 2H), 4.00 (s, 3H), 3.54 (td, J=12.8, 2.1 Hz, 2H), 3.09 (d, J=7.0 Hz, 2H), 2.18 (td, J=13.1, 4.6 Hz, 2H), 1.81 (d, J=11.9 Hz, 2H), 1.34-1.20 (m, 1H), 0.71-0.60 (m, 2H), 0.37 (d, J=5.5 Hz, 2H) MS (m+1)=398.2

Example 15

8-Chloro-3-(cyclopropylmethyl)-7-(4-(pyrimidin-2-yl)piperazin-1-yl)-[1,2,4]triazolo[4,3-b]pyridazine N'-(4-Chloro-5-(4-(pyrimidin-2-yl)piperazin-1-yl)pyridazin-3-yl)-2-cyclopropylacetohydrazide A solution of thionyl chloride (0.297 ml, 4.07 mmol) and 2-cyclopropylacetic acid (0.083 ml, 0.896 mmol) in methylene chloride (2.5 ml) was heated to reflux for 1 h and then concentrated. A solution of the residue in ethyl acetate (2.5 ml) was added to a mixture of 93536-039 (0.25 g, 0.815 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(pyrimidin-2-yl)piperazin-1-yl)pyridazin-3-yl)-2-cyclopropylacetohydrazide. The material was used without purification, assuming 100%. LCMS: Rt=1.967 min, 94%, (M−H)¯=387, (M+H)⁺=398.

8-Chloro-3-(cyclopropylmethyl)-7-(4-(pyrimidin-2-yl)piperazin-1-yl)-[1,2,4]triazolo[4,3-b]pyridazine A solution of N'-(4-chloro-5-(4-(pyrimidin-2-yl)piperazin-1-yl)pyridazin-3-yl)-2-cyclopropylacetohydrazide (0.315 g, 0.81 mmol) and phosphorus oxychloride (0.11 mg, 1.22 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil that was purified by preparative HPLC to give 8-chloro-3-(cyclopropylmethyl)-7-(4-(pyrimidin-2-yl)piperazin-1-yl)-[1,2,4]triazolo[4,3-b]pyridazine (6.7 mg, 2.2%). $^1$H NMR (500 MHz, DMSO-d$_6$) δ 8.67 (s, 1H), 8.43 (d, J=4.9 Hz, 2H), 6.70 (t, J=4.7 Hz, 1H), 3.94 (d, J=5.2 Hz, 4H), 3.50-3.38 (m, 4H), 3.02 (d, J=7.0 Hz, 2H), 1.31-1.15 (m, 1H), 0.50 (dd, J=7.9, 1.5 Hz, 2H), 0.30 (d, J=5.5 Hz, 2H). MS (m+1)=371.1.

Example 16

8-Chloro-3-neopentyl-7-(4-(pyrimidin-2-yl)piperazin-1-yl)-[1,2,4]triazolo[4,3-b]pyridazine N'-(4-Chloro-5-(4-(pyrimidin-2-yl)piperazin-1-yl)pyridazin-3-yl)-3,3-dimethylbutanehydrazide A solution of thionyl chloride (0.297 ml, 4.07 mmol) and 3,3-dimethylbutanoic acid (0.114 ml, 0.896 mmol) in methylene chloride (2.5 ml) was heated to reflux for 1 h then concentrated. A solution of the residue in ethyl acetate (2.5 ml) was added to a solution of 4-(piperidin-4-yl)pyrimidine (0.25 g, 0.815 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water, dried over magnesium sulfate, and concentrated to give N'-(4-chloro-5-(4-(pyrimidin-2-yl)piperazin-1-yl)pyridazin-3-yl)-3,3-dimethylbutanehydrazide as a brown oil. The material was used without purification, assuming 100%. LCMS: Rt=2.07 min, 63%, (M−H)¯=403, (M+H)⁺=405.

8-Chloro-3-neopentyl-7-(4-(pyrimidin-2-yl)piperazin-1-yl)-[1,2,4]triazolo[4,3-b]pyridazine A solution of N'-(4-chloro-5-(4-(pyrimidin-2-yl)piperazin-1-yl)pyridazin-3-yl)-3,3-dimethylbutanehydrazide (0.315 g, 0.788 mmol) and phosphorus oxychloride (0.109 ml, 1.167 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil which was purified by preparative HPLC to give 8-chloro-3-neopentyl-7-(4-(pyrimidin-2-yl)piperazin-1-yl)-[1,2,4]triazolo[4,3-b]pyridazine (12.3 mg, 4.1%). $^1$H NMR (500 MHz, DMSO-d$_6$) δ 8.65 (s, 1H), 8.43 (d, J=4.9 Hz, 2H), 6.70 (t, J=4.7 Hz, 1H), 3.99-3.84 (m, 4H), 3.47-3.38 (m, 4H), 3.01 (s, 2H), 1.00 (s, 9H). MS (m+1)=387.2.

Example 17

8-Chloro-3-(cyclopropylmethyl)-7-(4-(4-fluorophenyl)piperidin-1-yl)-[1,2,4]triazolo[4,3-b]pyridazine 4-Chloro-5-(4-(4-fluorophenyl)piperidin-1-yl)-3-hydrazinylpyridazine A mixture of 3,4,5-trichloropyridazine (0.50 g, 2.73 mmol), 4-(4-fluorophenyl)piperidine (0.508 g, 2.83 mmol), and potassium carbonate (0.791 g, 5.72 mmol) in dioxane (10 ml) was heated to reflux for 1 h. The mixture was cooled and 35% hydrazine (4.94 ml, 54.5 mmol) was added. The mixture was heated to reflux for 16 h overnight. The reaction was diluted with ethyl acetate and water. The ethyl acetate layer was washed with water, dried over magnesium sulfate, and concentrated to give 4-chloro-5-(4-(4-fluorophenyl)piperidin-1-yl)-3-hydrazinylpyridazine as a brown oil (0.641 g, 73%). The material was used without purification. LCMS: Rt=2.33 min, 37%, (M−H)⁻=320, (M+H)⁺=322.

N'-(4-Chloro-5-(4-(4-fluorophenyl)piperidin-1-yl)pyridazin-3-yl)-2-cyclopropylacetohydrazide A solution of thionyl chloride (0.284 ml, 3.88 mmol) and 2-cyclopropylacetic acid (0.080 ml, 0.855 mmol) in methylene chloride (2.5 ml) was heated to reflux for 1 h then concentrated. A solution of the residue in ethyl acetate (2.5 ml) was added to a mixture of 4-chloro-5-(4-(4-fluorophenyl)piperidin-1-yl)-3-hydrazinylpyridazine (0.25 g, 0.777 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(4-fluorophenyl)piperidin-1-yl)pyridazin-3-yl)-2-cyclopropylacetohydrazide. The material was used without purification, assuming 100%. LCMS: 2.353 min, 87%, (M−H)⁻=402, (M+H)⁺=404.

8-Chloro-3-(cyclopropylmethyl)-7-(4-(4-fluorophenyl)piperidin-1-yl)-[1,2,4]triazolo[4,3-b]pyridazine A solution of N'-(4-chloro-5-(4-(4-fluorophenyl)piperidin-1-yl)pyridazin-3-yl)-2-cyclopropylacetohydrazide (0.30 g, 0.743 mmol) and phosphorus oxychloride (0.104 ml, 1.11 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to give an oil which was purified by preparative HPLC to give 8-chloro-3-(cyclopropylmethyl)-7-(4-(4-fluorophenyl)piperidin-1-yl)-[1,2,4]triazolo[4,3-b]pyridazine (7 mg, 2.44%). ¹H NMR (500 MHz, DMSO-d₆) δ 8.67 (s, 1H), 7.37 (dd, J=8.5, 5.8 Hz, 2H), 7.16 (t, J=8.9 Hz, 2H), 3.74 (d, J=12.5 Hz, 2H), 3.25-3.11 (m, 2H), 3.02 (d, J=7.0 Hz, 2H), 2.87-2.70 (m, 1H), 1.99-1.74 (m, 4H), 1.30-1.16 (m, 1H), 0.51 (dd, J=7.9, 1.5 Hz, 2H), 0.30 (d, J=5.5 Hz, 2H). MS (M+1)=386.2.

Example 18

8-Chloro-7-(4-(4-fluorophenyl)piperidin-1-yl)-3-neopentyl-[1,2,4]triazolo[4,3-b]pyridazine N'-(4-Chloro-5-(4-(4-fluorophenyl)piperidin-1-yl)pyridazin-3-yl)-3,3-dimethylbutanehydrazide A solution of thionyl chloride (0.284 ml, 3.88 mmol) and 3,3-dimethylbutanoic acid (0.109 ml, 0.855 mmol) in methylene chloride (2.5 ml) was heated to reflux for 1 h then concentrated. A solution of the residue in ethyl acetate (2.5 ml) was added to a solution of 93536-064 (0.25 g, 0.777 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(4-fluorophenyl)piperidin-1-yl)pyridazin-3-yl)-3,3-dimethylbutanehydrazide (0.30 g, 92%) which was used without purification. LCMS: Rt=2.455 min, 90%, (M−H)⁻=418, (M+H)⁺=420.

8-Chloro-7-(4-(4-fluorophenyl)piperidin-1-yl)-3-neopentyl-[1,2,4]triazolo[4,3-b]pyridazine A solution of N'-(4-chloro-5-(4-(4-fluorophenyl)piperidin-1-yl)pyridazin-3-yl)-3,3-dimethylbutanehydrazide (0.30 g, 0.714 mmol) and phosphorus oxychloride (0.1 ml, 1.072 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil which was purified by preparative HPLC to give 8-chloro-7-(4-(4-fluorophenyl)piperidin-1-yl)-3-neopentyl-[1,2,4]triazolo[4,3-b]pyridazine (4.8 mg, 1.6%). ¹H NMR (500 MHz, DMSO-d₆) δ 8.66 (s, 1H), 7.37 (dd, J=8.5, 5.8 Hz, 2H), 7.16 (t, J=8.9 Hz, 2H), 3.74 (d, J=12.2 Hz, 2H), 3.25-3.11 (m, 2H), 3.01 (s, 2H), 2.85-2.72 (m, 1H), 1.95-1.73 (m, 4H), 1.00 (s, 8H). MS (m+1)=402.2

Example 19

8-Chloro-3-(cyclopropylmethyl)-7-(4-(4-fluorophenyl)piperazin-1-yl)-[1,2,4]triazolo[4,3-b]pyridazine 4-Chloro-5-(4-(4-fluorophenyl)piperazin-1-yl)-3-hydrazinylpyridazine A mixture of 3,4,5-trichloropyridazine (0.50 g, 2.73 mmol), 1-(4-fluorophenyl)piperazine (0.511 g, 2.83 mmol), and potassium carbonate (0.791 g, 5.72 mmol) in dioxane (10 ml) was heated to reflux for 1 h. The mixture was cooled and 35% hydrazine (4.94 ml, 54.5 mmol) was added. The mixture was heated to reflux for 16 h overnight. The reaction was diluted with ethyl acetate and water. The ethyl acetate layer was washed with water, dried over magnesium sulfate, and concentrated to give 4-chloro-5-(4-(4-fluorophenyl)piperazin-1-yl)-3-hydrazinylpyridazine (0.880 g, 100%), which was used without purification. LCMS: Rt=2.25 min, 51%, (M−H)=321, (M+H)⁺=323.

N'-(4-Chloro-5-(4-(4-fluorophenyl)piperazin-1-yl)pyridazin-3-yl)-2-cyclopropylacetohydrazide A solution of thionyl chloride (0.283 ml, 3.87 mmol) and 2-cyclopropylacetic acid (0.079 ml, 0.852 mmol) in methylene chloride (2.5 ml) was heated to reflux for 1 h and then concentrated. A solution of the residue in ethyl acetate (2.5 ml) and was added to a solution of 4-chloro-5-(4-(4-fluorophenyl)piperazin-1-yl)-3-hydrazinylpyridazine (0.25 g, 0.775 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(4-fluorophenyl)piperazin-1-yl)pyridazin-3-yl)-2-cyclopropylacetohydrazide (0.30 g, 96%). LCMS: Rt=2.208 min, 96%, (M−H)⁻=403, (M+H)⁺=405.

8-Chloro-3-(cyclopropylmethyl)-7-(4-(4-fluorophenyl)piperazin-1-yl)-[1,2,4]triazolo[4,3-b]pyridazine A solution of N'-(4-chloro-5-(4-(4-fluorophenyl)piperazin-1-yl)pyridazin-3-yl)-2-cyclopropylacetohydrazide (0.30 g, 0.741 mmol) and phosphorus oxychloride (0.104 ml, 1.11 mmol) in acetonitrile (6 ml) heated to 80° C. for 16 h. The reaction was cooled. The reaction was cooled and quenched with saturated sodium carbonate. The mixture was diluted with ethyl acetate and water. The ethyl acetate layer was separated and concentrated to an oil which was purified by preparative HPLC to give 8-chloro-3-(cyclopropylmethyl)-7-(4-(4-fluorophenyl)piperazin-1-yl)-[1,2,4]triazolo[4,3-b]pyridazine (9.2 mg, 3.2%). $^1$H NMR (500 MHz, DMSO-$d_6$) δ 8.69 (s, 1H), 7.19-6.97 (m, 4H), 3.56-3.43 (m, 4H), 3.30-3.26 (m, 4H), 3.03 (d, J=7.0 Hz, 2H), 1.32-1.14 (m, 1H), 0.58-0.44 (m, 2H), 0.30 (d, J=5.8 Hz, 2H). MS (m+1)=387.1.

Example 20

8-Chloro-3-(cyclopropylmethyl)-7-(spiro[indene-1,4'-piperidin]-1'-yl)-[1,2,4]triazolo[4,3-b]pyridazine 1'-(5-Chloro-6-hydrazinylpyridazin-4-yl)spiro[indene-1,4'-piperidine]

A mixture of 3,4,5-trichloropyridazine (0.5 g, 2.73 mmol), spiro[indene-1,4'-piperidine]hydrochloride (0.604 g, 2.73 mmol), and potassium carbonate (0.791 g, 5.72 mmol) in dioxane (10 ml) was heated to reflux for 16 h. The mixture was cooled and 35% hydrazine (4.94 ml, 54.5 mmol) was added. The mixture was heated to reflux for 16 h. The reaction was diluted with ethyl acetate and water. The ethyl acetate layer was washed with water, dried over magnesium sulfate, and concentrated to give 1'-(5-chloro-6-hydrazinylpyridazin-4-yl)spiro[indene-1,4'-piperidine] which was used without purification.

N'-(4-Chloro-5-(spiro[indene-1,4'-piperidin]-1'-yl)pyridazin-3-yl)-2-cyclopropylacetohydrazide A solution of thionyl chloride (0.278 ml, 3.81 mmol) and 2-cyclopropylacetic acid (0.078 ml, 0.839 mmol) in methylene chloride (2.5 ml) was heated to reflux for 1 h and then concentrated. A solution of the residue in ethyl acetate (2.5 ml) and was added to a solution of 1'-(5-chloro-6-hydrazinylpyridazin-4-yl)spiro[indene-1,4'-piperidine] (0.25 g, 0.763 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(spiro[indene-1,4'-piperidin]-1'-yl)pyridazin-3-yl)-2-cyclopropylacetohydrazide (0.25 g, 80%). LCMS: Rt=0.83 min, 20%, (M+H)$^+$=410.

8-Chloro-3-(cyclopropylmethyl)-7-(spiro[indene-1,4'-piperidin]-1'-yl)-[1,2,4]triazolo[4,3-b]pyridazine A solution of N'-(4-chloro-5-(spiro[indene-1,4'-piperidin]-1'-yl)pyridazin-3-yl)-2-cyclopropylacetohydrazide (0.25 g, 0.61 mmol) and phosphorus oxychloride (0.085 ml, 0.915 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil which was purified by preparative HPLC to give 8-chloro-3-(cyclopropylmethyl)-7-(spiro[indene-1,4'-piperidin]-1'-yl)-[1,2,4]triazolo[4,3-b]pyridazine (33.6 mg, 13.5%). $^1$H NMR (500 MHz, DMSO-$d_6$) δ 7.54 (d, J=7.6 Hz, 1H), 7.39 (d, J=7.6 Hz, 2H), 7.31-7.19 (m, 3H), 6.89 (d, J=5.8 Hz, 1H), 3.74 (d, J=13.4 Hz, 2H), 3.50 (t, J=12.2 Hz, 2H), 3.04 (d, J=6.7 Hz, 2H), 2.32-2.19 (m, 2H), 1.38 (d, J=12.2 Hz, 2H), 1.29-1.13 (m, 1H), 0.58-0.46 (m, 2H), 0.31 (d, J=5.5 Hz, 2H). MS (m+1)=392.2.

Example 21

8-Chloro-3-(cyclopropylmethyl)-N-((1-(phenoxymethyl)cyclopropyl)methyl)-[1,2,4]triazolo[4,3-b]pyridazin-7-amine 5-Chloro-6-hydrazinyl-N-((1-(phenoxymethyl)cyclopropyl)methyl)pyridazin-4-amine A mixture of 3,4,5-trichloropyridazine (0.50 g, 2.73 mmol), (1-(phenoxymethyl)cyclopropyl)methanamine (0.483 g, 2.73 mmol), and potassium carbonate (0.791 g, 5.72 mmol) in dioxane (10 ml) was heated to reflux for 1 h. The mixture was cooled and 35% hydrazine (4.94 ml, 54.5 mmol) was added. The mixture was heated to reflux for 16 h overnight. The reaction was diluted with ethyl acetate and water. The ethyl acetate layer was washed with water, dried over magnesium sulfate, and concentrated to give 5-chloro-6-hydrazinyl-N-((1-(phenoxymethyl)cyclopropyl)methyl)pyridazin-4-amine as a brown oil (0.872 g, 100%). LCMS: Rt=2.47 min, 32%, (M−H)$^-$=318, (M+H)$^+$=320.

N'-(4-Chloro-5-(((1-(phenoxymethyl)cyclopropyl)methyl)amino)pyridazin-3-yl)-2-cyclopropyl acetohydrazide A solution of thionyl chloride (0.285 ml, 3.91 mmol) and 2-cyclopropylacetic acid (0.080 ml, 0.860 mmol) in methylene chloride (2.5 ml) was heated to reflux for 1 h and then concentrated. The residue was dissolved in ethyl acetate (2.5 ml) and added to a mixture of 5-chloro-6-hydrazinyl-N-((1-(phenoxymethyl)cyclopropyl)methyl)pyridazin-4-amine (0.25 g, 0.782 mmol) in ethyl acetate (2.5 ml), THF (5 ml), and saturated sodium bicarbonate (5 ml)). The mixture was stirred for 16 h. The reaction was diluted with ethyl acetate and water. The ethyl acetate layer was washed with water and concentrated to give N'-(4-chloro-5-(((1-(phenoxymethyl)cyclopropyl)methyl)amino)pyridazin-3-yl)-2-cyclopropylacetohydrazide (0.250 g, 80%). LCMS: Rt=0.77 min, 29%, (M+H)$^+$=402.

8-Chloro-3-(cyclopropylmethyl)-N-((1-(phenoxymethyl)cyclopropyl)methyl)-[1,2,4]triazolo[4,3-b]pyridazin-7-amine A solution of N'-(4-chloro-5-(((1-(phenoxymethyl)cyclopropyl)methyl)amino) pyridazin-3-yl)-2-cyclopropylacetohydrazide (0.25 g, 0.622 mmol) and phosphorus oxychloride (0.087 ml, 0.933 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil which was purified by preparative HPLC to give 8-chloro-3-(cyclopropylmethyl)-N-((1-(phenoxymethyl)cyclopropyl)methyl)-[1,2,4]triazolo[4,3-b]pyridazin-7-amine (2.3 mg, 1%). $^1$H NMR (500 MHz, DMSO-$d_6$) δ 8.58 (s, 1H), 7.22 (t, J=7.9 Hz, 2H), 6.95-6.77 (m, 3H), 3.87 (s, 2H), 3.60 (d, J=6.4 Hz, 2H), 2.87 (d, J=7.0 Hz, 2H), 1.86 (s, 1H), 1.18-1.02 (m, 1H), 0.75-0.69 (m, 2H), 0.65-0.58 (m, 2H), 0.48-0.41 (m, 2H), 0.22 (d, J=5.5 Hz, 2H). MS (m+1)=384.1.

Example 22

8-Chloro-3-(cyclopropylmethyl)-7-(4-(2-fluoro-6-methoxyphenyl)piperidin-1-yl)-[1,2,4]triazolo[4,3-b]pyridazine

4-Chloro-5-(4-(2-fluoro-6-methoxyphenyl)piperidin-1-yl)-3-hydrazinylpyridazine A mixture of 3,4,5-trichloropyridazine (0.20 g, 1.090 mmol), 4-(2-fluoro-6-methoxyphenyl)piperidine hydrochloride (0.268 g, 1.090 mmol), and potassium carbonate (0.316 g, 2.290 mmol) in dioxane (10 ml) was heated to reflux for 1 h. The reaction was diluted with ethyl acetate and water. The ethyl acetate layer was washed with water, dried over magnesium sulfate, and concentrated to give 4-chloro-5-(4-(2-fluoro-6-methoxyphenyl)piperidin-1-yl)-3-hydrazinylpyridazine as a brown oil (0.25 g, 65%). LCMS: Rt=2.06 min, 13%, (M−H)⁻=350, (M+H)⁺=352.

N'-(4-Chloro-5-(4-(2-fluoro-6-methoxyphenyl)piperidin-1-yl)pyridazin-3-yl)-2-cyclopropylacetohydrazide A solution of thionyl chloride (0.259 ml, 3.55 mmol) and 2-cyclopropylacetic acid (0.073 ml, 0.782 mmol) in methylene chloride (2.5 ml) was heated to reflux for 1 h and then concentrated. A solution of the residue in ethyl acetate (2.5 ml) was added to a solution of 4-chloro-5-(4-(2-fluoro-6-methoxyphenyl)piperidin-1-yl)-3-hydrazinylpyridazine (0.25 g, 0.711 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(2-fluoro-6-methoxyphenyl)piperidin-1-yl)pyridazin-3-yl)-2-cyclopropylacetohydrazide (0.25 g, 81%). LCMS: Rt=2.10 min, 43%, (M−H)⁻=432, (M+H)⁺=434.

8-Chloro-3-(cyclopropylmethyl)-7-(4-(2-fluoro-6-methoxyphenyl)piperidin-1-yl)-[1,2,4]triazolo[4,3-b]pyridazine A mixture of N'-(4-chloro-5-(4-(2-fluoro-6-methoxyphenyl)piperidin-1-yl)pyridazin-3-yl)-2-cyclopropylacetohydrazide (0.250 g, 0.576 mmol) and Burgess' reagent (0.343 g, 1.440 mmol) in acetonitrile (6 ml) in a microwave vial was heated to 80° C. for 16 h. The reaction with diluted with ethyl acetate and aqueous sodium carbonate. The ethyl acetate layer was separated, washed with water, dried with brine, and concentrated to an oil that was purified by preparative HPLC to give 8-chloro-3-(cyclopropylmethyl)-7-(4-(2-fluoro-6-methoxyphenyl)piperidin-1-yl)-[1,2,4]triazolo[4,3-b]pyridazine (2.1 mg, 0.86%). $^{1}$H NMR (500 MHz, DMSO-$d_6$) δ 8.66 (s, 1H), 7.31-7.18 (m, 1H), 6.88 (d, J=8.2 Hz, 1H), 6.79 (dd, J=10.7, 8.5 Hz, 1H), 3.84 (s, 3H), 3.71 (d, J=11.9 Hz, 2H), 3.14 (t, J=12.1 Hz, 2H), 3.02 (d, J=7.0 Hz, 2H), 2.34-2.18 (m, 2H), 1.71 (d, J=11.0 Hz, 2H), 1.30-1.16 (m, 1H), 0.51 (dd, J=7.9, 1.5 Hz, 2H), 0.30 (d, J=5.8 Hz, 2H). MS (m+1)=416.0.

Example 23

8-Chloro-3-(cyclopropylmethyl)-7-(4-(2-fluorophenyl)piperidin-1-yl)-[1,2,4]triazolo[4,3-b]pyridazine

4-Chloro-5-(4-(2-fluorophenyl)piperidin-1-yl)-3-hydrazinylpyridazine

A mixture of 3,4,5-trichloropyridazine (0.50 g, 2.73 mmol), 4-(2-fluorophenyl)piperidine 4-methylbenzenesulfonate (0.958 g, 2.73 mmol), and potassium carbonate (0.791 g, 5.72 mmol) in dioxane (10 ml) was heated to reflux for 1 h. The mixture was cooled and 35% hydrazine (4.94 ml, 54.5 mmol) was added. The mixture was heated to reflux for 16 h overnight. The reaction was diluted with ethyl acetate and water. The ethyl acetate layer was washed with water, dried over magnesium sulfate, and concentrated to give 4-chloro-5-(4-(2-fluorophenyl) piperidin-1-yl)-3-hydrazinylpyridazine (0.25 g, 28%). LCMS: Rt=1.957 min, 76%, (M−H)⁻=320, (M+H)⁺=322.

N'-(4-Chloro-5-(4-(2-fluorophenyl)piperidin-1-yl)pyridazin-3-yl)-2-cyclopropylacetohydrazide A solution of thionyl chloride (0.284 ml, 3.88 mmol) and 2-cyclopropylacetic acid (0.080 ml, 0.855 mmol) in methylene chloride (2.5 ml) was heated to reflux for 1 h and then concentrated. A solution of the residue in ethyl acetate (2.5 ml) was added to a solution of 4-chloro-5-(4-(2-fluorophenyl)piperidin-1-yl)-3-hydrazinyl pyridazine (0.25 g, 0.777 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(2-fluorophenyl)piperidin-1-yl)pyridazin-3-yl)-2-cyclopropylacetohydrazide (0.250 g, 80%). LCMS: Rt=1.978 min, 34%, (M−H)=402, (M+H)⁺=404.

8-Chloro-3-(cyclopropylmethyl)-7-(4-(2-fluorophenyl)piperidin-1-yl)-[1,2,4]triazolo[4,3-b]pyridazine A mixture of N'-(4-chloro-5-(4-(2-fluorophenyl)piperidin-1-yl)pyridazin-3-yl)-2-cyclopropylacetohydrazide (0.250 g, 0.619 mmol) and phosphorus oxychloride (0.087 ml, 0.928 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil which was purified by preparative HPLC to give 8-chloro-3-(cyclopropylmethyl)-7-(4-(2-fluorophenyl)piperidin-1-yl)-[1,2,4]triazolo[4,3-b]pyridazine (15.8 mg, 6.6%). $^{1}$H NMR (500 MHz, DMSO-$d_6$) δ 8.67 (s, 1H), 7.43 (t, J=7.6 Hz, 1H), 7.35-7.26 (m, 1H), 7.25-7.12 (m, 2H), 3.75 (d, J=12.8 Hz, 1H), 3.27-3.14 (m, 3H), 3.10-2.96 (m, 3H), 1.90 (d, J=5.2 Hz, 3H), 1.32-1.15 (m, 1H), 0.58-0.46 (m, 2H), 0.35-0.24 (m, 2H). MS (m+1)=386.0.

Example 24

8-Chloro-3-(cyclopropylmethyl)-7-(4-(3-fluorophenyl)piperidin-1-yl)-[1,2,4]triazolo[4,3-b]pyridazine

4-Chloro-5-(4-(3-fluorophenyl)piperidin-1-yl)-3-hydrazinylpyridazine

A mixture of 3,4,5-trichloropyridazine (0.276 g, 1.506 mmol), 4-(3-fluorophenyl)piperidine (0.27 g, 1.506 mmol), and potassium carbonate (0.437 g, 3.16 mmol) in dioxane (10 ml) was heated to reflux for 1 h. The mixture was cooled and 35% hydrazine (2.73 ml, 30.1 mmol) was added. The mixture was heated to reflux for an additional 16 h. The reaction was diluted with ethyl acetate and water. The ethyl acetate layer was washed with water, dried over magnesium sulfate, and concentrated to give 4-chloro-5-(4-(3-fluorophenyl)piperidin-1-yl)-3-hydrazinylpyridazine (0.25 g, 52%). LCMS: Rt=1.940 min, 26%, (M−H)⁻=320, (M+H)⁺=322.

N'-(4-Chloro-5-(4-(3-fluorophenyl)piperidin-1-yl)pyridazin-3-yl)-2-cyclopropylacetohydrazide A solution of thionyl chloride (0.284 ml, 3.88 mmol) and 2-cyclopropylacetic acid (0.080 ml, 0.855 mmol) in methylene chloride (2.5 ml) was heated to reflux for 1 h and then concentrated. A solution of the residue in ethyl acetate (2.5 ml) was added to a solution of 4-chloro-5-(4-(3-fluorophenyl)piperidin-1-yl)-3-hydrazinylpyridazine (0.25 g, 0.777 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(3-fluorophenyl)piperidin-1-yl)pyridazin-3-yl)-2-cyclopropylacetohydrazide ((0.25 g, 80%). LCMS: Rt=1.972, 77%, (M−H)⁻=402, (M+H)⁺=404.

8-Chloro-3-(cyclopropylmethyl)-7-(4-(3-fluorophenyl)piperidin-1-yl)-[1,2,4]triazolo[4,3-b]pyridazine A solution of N'-(4-chloro-5-(4-(3-fluorophenyl)piperidin-1-yl)pyridazin-3-yl)-2-cyclopropylacetohydrazide (0.250 g, 0.619 mmol) and phosphorus oxychloride (0.087 ml, 0.928 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil which was purified by preparative HPLC to give 8-chloro-3-(cyclopropylmethyl)-7-(4-(3-fluorophenyl)piperidin-1-yl)-[1,2,4]triazolo[4,3-b]pyridazine (11.6 mg, 5%). $^1$H NMR (500 MHz, DMSO-$d_6$) δ 8.67 (s, 1H), 7.45-7.31 (m, 1H), 7.24-7.13 (m, 2H), 7.06 (t, J=8.4 Hz, 1H), 3.75 (d, J=12.2 Hz, 2H), 3.27-3.11 (m, 2H), 3.02 (d, J=6.7 Hz, 2H), 2.88-2.75 (m, 1H), 1.99-1.73 (m, 4H), 1.31-1.15 (m, 1H), 0.51 (d, J=6.4 Hz, 2H), 0.30 (d, J=4.9 Hz, 2H). MS (m+1)=386.2.

Example 25

8-Chloro-7-(4-(2-fluorophenyl)piperidin-1-yl)-3-(2,2,2-trifluoroethyl)-[1,2,4]triazolo[4,3-b]pyridazine N'-(4-Chloro-5-(4-(2-fluorophenyl)piperidin-1-yl)pyridazin-3-yl)-3,3,3-trifluoropropanehydrazide A solution of 3,3,3-trifluoropropanoyl chloride (0.125 g, 0.855 mmol) in ethyl acetate (2.5 ml) was added to a mixture of 4-chloro-5-(4-(2-fluorophenyl) piperidin-1-yl)-3-hydrazinylpyridazine (0.25 g, 0.777 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(2-fluorophenyl)piperidin-1-yl)pyridazin-3-yl)-3,3,3-trifluoropropanehydrazide (0.25 g, 74%). LCMS: Rt=2.08 min, (M−H)⁻=430, (M+H)⁺=432.

8-Chloro-7-(4-(2-fluorophenyl)piperidin-1-yl)-3-(2,2,2-trifluoroethyl)-[1,2,4]triazolo[4,3-b]pyridazine A solution of N'-(4-chloro-5-(4-(2-fluorophenyl)piperidin-1-yl)pyridazin-3-yl)-3,3,3-trifluoropropanehydrazide (0.25 g, 0.579 mmol) and phosphorus oxychloride (0.081 ml in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to an oil which was purified by preparative HPLC to give 8-chloro-7-(4-(2-fluorophenyl)piperidin-1-yl)-3-(2,2,2-trifluoroethyl)-[1,2,4]triazolo[4,3-b]pyridazine (13.6 mg, 5.5%). $^1$H NMR (500 MHz, DMSO-$d_6$) δ 8.77 (s, 1H), 7.42 (t, J=7.6 Hz, 1H), 7.34-7.27 (m, 1H), 7.24-7.16 (m, 2H), 4.47-4.25 (m, 1H), 3.87-3.74 (m, 1H), 3.30-3.18 (m, 3H), 3.14-2.97 (m, 1H), 2.00-1.84 (m, 4H), 1.82-1.58 (m, 1H). LCMS (M+H)⁺=414.0.

Example 26

8-Chloro-7-(4-(2-fluoro-6-methoxyphenyl)piperidin-1-yl)-3-(2,2,2-trifluoroethyl)-[1,2,4]triazolo[4,3-b]pyridazine N'-(4-Chloro-5-(4-(2-fluoro-6-methoxyphenyl)piperidin-1-yl)pyridazin-3-yl)-3,3,3-trifluoropropanehydrazide A mixture of 4-chloro-5-(4-(2-fluoro-6-methoxyphenyl)piperidin-1-yl)-3-hydrazinylpyridazine (0.50 g, 1.421 mmol) in ethyl acetate (2.5 ml), THF (5 ml), and saturated sodium bicarbonate (5 ml) and was stirred as 3,3,3-trifluoropropanoyl chloride (0.229 g, 1.563 mmol) was added. The mixture was stirred at room temperature for 16 h. The reaction was diluted with ethyl acetate and water. The ethyl acetate layer was washed with water and concentrated to give N'-(4-chloro-5-(4-(2-fluoro-6-methoxyphenyl)piperidin-1-yl)pyridazin-3-yl)-3,3,3-trifluoropropanehydrazide as a brown oil (0.570 g, 87%).

8-Chloro-7-(4-(2-fluoro-6-methoxyphenyl)piperidin-1-yl)-3-(2,2,2-trifluoroethyl)-[1,2,4]triazolo[4,3-b]pyridazine A mixture of N'-(4-chloro-5-(4-(2-fluoro-6-methoxyphenyl)piperidin-1-yl)pyridazin-3-yl)-3,3,3-trifluoropropanehydrazide (0.570 g, 1.234 mmol) and phosphorus oxychloride (0.173 ml, 1.851 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil which was purified by preparative HPLC to give 8-chloro-7-(4-(2-fluoro-6-methoxyphenyl)piperidin-1-yl)-3-(2,2,2-trifluoroethyl)-[1,2,4]triazolo[4,3-b]pyridazine (10.4 mg, 1.8%) as a tan solid. $^1$H NMR (500 MHz, METHANOL-$d_4$) δ 8.64 (s, 1H), 7.25-7.15 (m, 1H), 6.82 (d, J=8.2 Hz, 1H), 6.70 (dd, J=10.4, 8.9 Hz, 1H), 4.23 (q, J=10.2 Hz, 2H), 3.97-3.82 (m, 5H), 3.52-3.15 (m, 1H), 2.56-2.36 (m, 2H), 1.78 (d, J=12.5 Hz, 2H), 1.38-1.22 (m, 2H). LCMS (M+H)⁺=444.04.

Example 27

8-Chloro-3-(cyclopropylmethyl)-7-(4-(2-methoxyphenyl)piperidin-1-yl)-[1,2,4]triazolo[4,3-b]pyridazine 4-Chloro-3-hydrazinyl-5-(4-(2-methoxyphenyl)piperidin-1-yl)pyridazine A mixture of 3,4,5-trichloropyridazine (0.250 g, 1.363 mmol), 4-(2-methoxyphenyl)piperidine (0.261 g, 1.363 mmol), and potassium carbonate (0.396 g, 2.86 mmol) in dioxane (10 ml) was heated to reflux for 1 h. The mixture was cooled and 35% hydrazine (2.469 ml, 27.3 mmol) was added. The mixture was heated to reflux for 16 h. The mixture was heated to reflux for an additional 16 h. The reaction was diluted with ethyl acetate and water. The ethyl acetate layer was washed with water, dried over magnesium sulfate, and concentrated to give 4-chloro-3-hydrazinyl-5-(4-(2-methoxyphenyl)piperidin-1-yl)pyridazine as a brown oil that was used without purification. LCMS: Rt=0.77 min, 22%, (M+H)$^+$=334.

N'-(4-Chloro-5-(4-(2-methoxyphenyl) piperidin-1-yl)pyridazin-3-yl)-2-cyclopropylacetohydrazide A solution of thionyl chloride (0.273 ml, 3.74 mmol) and 2-cyclopropylacetic acid (0.077 ml, 0.824 mmol) in methylene chloride (2.5 ml) was heated to reflux for 1 h then concentrated. A solution of the residue in ethyl acetate (2.5 ml) was added to a mixture of 4-chloro-3-hydrazinyl-5-(4-(2-methoxyphenyl)piperidin-1-yl)pyridazine (0.25 g, 0.749 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(2-methoxyphenyl) piperidin-1-yl)pyridazin-3-yl)-2-cyclopropylacetohydrazide as a brown oil that was used without purification. LCMS: Rt=2.10 min, 56%, (M−H)$^-$=414, (M+H)$^+$=416.

8-Chloro-3-(cyclopropylmethyl)-7-(4-(2-methoxyphenyl)piperidin-1-yl)-[1,2,4]triazolo[4,3-b]pyridazine A mixture of N'-(4-chloro-5-(4-(2-methoxyphenyl)piperidin-1-yl)pyridazin-3-yl)-2-cyclopropylacetohydrazide (0.25 g, 0.601 mmol) and phosphorus oxychloride (0.084 ml, 0.902 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil which was purified by preparative HPLC to give 8-chloro-3-(cyclopropylmethyl)-7-(4-(2-methoxyphenyl)piperidin-1-yl)-[1,2,4]triazolo[4,3-b]pyridazine (28.2 mg, 11.8%). $^1$H NMR (500 MHz, DMSO-d$_6$) δ 8.67 (s, 1H), 7.33-7.16 (m, 2H), 7.07-6.89 (m, 2H), 3.83 (s, 3H), 3.73 (d, J=11.9 Hz, 2H), 3.26-3.07 (m, 2H), 3.02 (d, J=6.7 Hz, 2H), 1.92-1.70 (m, 4H), 1.31-1.15 (m, 1H), 0.56-0.44 (m, 2H), 0.30 (d, J=5.2 Hz, 2H). LCMS (M+H)$^+$=398.2.

Example 28

8-Chloro-3-(cyclopropylmethyl)-7-(4-(3-methoxyphenyl)piperidin-1-yl)-[1,2,4]triazolo[4,3-b]pyridazine 4-Chloro-3-hydrazinyl-5-(4-(3-methoxyphenyl)piperidin-1-yl)pyridazine A mixture of 3,4,5-trichloropyridazine (0.250 g, 1.363 mmol), 4-(3-methoxyphenyl)piperidine (0.261 g, 1.363 mmol), and potassium carbonate (0.396 g, 2.86 mmol) in dioxane (10 ml) was heated to reflux for 1 h. The mixture was cooled and 35% hydrazine (2.469 ml, 27.3 mmol) was added. The mixture was heated to reflux for 16 h overnight. The mixture was heated to reflux for an additional 16 h. The reaction was diluted with ethyl acetate and water. The ethyl acetate layer was washed with water, dried over magnesium sulfate, and concentrated to give 4-chloro-3-hydrazinyl-5-(4-(3-methoxyphenyl)piperidin-1-yl)pyridazine as a brown oil. LCMS: Rt=0.74 min, 35%, (M+H)$^+$=334.

N'-(4-Chloro-5-(4-(3-methoxyphenyl)piperidin-1-yl) pyridazin-3-yl)-2-cyclopropylacetohydrazide A solution of thionyl chloride (0.273 ml, 3.74 mmol) and 2-cyclopropylacetic acid (0.077 ml, 0.824 mmol) in methylene chloride (2.5 ml) was heated to reflux for 1 h and then concentrated. A solution of the residue in ethyl acetate (2.5 ml) was added to a mixture of 4-chloro-3-hydrazinyl-5-(4-(3-methoxyphenyl)piperidin-1-yl)pyridazine (0.25 g, 0.749 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(3-methoxyphenyl)piperidin-1-yl)pyridazin-3-yl)-2-cyclopropylacetohydrazide (0.25 g, 80%). LCMS: Rt=2.00 min, 73%, (M−H)$^-$=414, (M+H)$^+$=416.

8-Chloro-3-(cyclopropylmethyl)-7-(4-(3-methoxyphenyl)piperidin-1-yl)-[1,2,4]triazolo[4,3-b]pyridazine A solution of N'-(4-chloro-5-(4-(3-methoxyphenyl)piperidin-1-yl)pyridazin-3-yl)-2-cyclopropylacetohydrazide (0.250 g, 0.601 mmol) and phosphorus oxychloride (0.084 ml, 0.902 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(3-methoxyphenyl) piperidin-1-yl)-[1,2,4]triazolo[4,3-b]pyridazine (17.4 mg, 7%). $^1$H NMR (500 MHz, DMSO-d$_6$) δ 8.67 (s, 1H), 7.25 (t, J=7.9 Hz, 1H), 6.95-6.84 (m, 2H), 6.80 (dd, J=8.1, 2.0 Hz, 1H), 3.82-3.68 (m, 5H), 3.25-3.11 (m, 2H), 3.02 (d, J=6.7 Hz, 2H), 2.87-2.68 (m, 1H), 1.98-1.75 (m, 4H), 1.29-1.17 (m, 1H), 0.51 (dd, J=7.9, 1.5 Hz, 2H), 0.30 (d, J=5.5 Hz, 2H). LCMS (M+H)$^+$=398.2.

Example 29

8-Chloro-3-(cyclopropylmethyl)-7-(4-(o-tolyl)piperidin-1-yl)-[1,2,4]triazolo[4,3-b]pyridazine 4-Chloro-3-hydrazinyl-5-(4-(o-tolyl)piperidin-1-yl) pyridazine A mixture of 3,4,5-trichloropyridazine (0.250 g, 1.363 mmol), 4-(o-tolyl)piperidine 4-methylbenzenesulfonate (0.474 g, 1.363 mmol), and potassium carbonate (0.396 g, 2.86 mmol) in dioxane (10 ml) was heated to reflux for 1 h. The mixture was cooled and 35% hydrazine (2.469 ml, 27.3 mmol) was added. The mixture was heated to reflux for 16 h overnight. The reaction was diluted with ethyl acetate and water. The ethyl acetate layer was washed with water, dried over magnesium sulfate, and concentrated to give 4-chloro-3-hydrazinyl-5-(4-(o-tolyl)piperidin-1-yl)pyridazine as a brown oil. LCMS: Rt=1.58 min, 37%, (M−H)$^-$=320, (M+H)$^+$=322.

N'-(4-Chloro-5-(4-(o-tolyl)piperidin-1-yl)pyridazin-3-yl)-2-cyclopropylacetohydrazide A solution of thionyl chloride (0.287 ml, 3.93 mmol) and 2-cyclopropylacetic acid (0.081 ml, 0.865 mmol) in methylene chloride (2.5 ml) was heated to reflux for 1 h then and concentrated. A solution of the residue in ethyl acetate (2.5 ml) and was added to a solution of 4-chloro-3-hydrazinyl-5-(4-(o-tolyl)piperidin-1-yl)pyridazine (0.25 g, 0.787 mmol) in ethyl acetate (2.5 ml), THF (5 ml), and saturated sodium bicarbonate (5 ml). The mixture was stirred temperature for 16 h. The reaction was diluted with ethyl acetate and water. The ethyl acetate layer was washed with water and concentrated to give N'-(4-chloro-5-(4-(o-tolyl)piperidin-1-yl)pyridazin-3-yl)-2-cyclopropylacetohydrazide as a brown oil. LCMS: Rt=2.12 min, (M−H)⁻=398, (M+H)⁺=400.

8-Chloro-3-(cyclopropylmethyl)-7-(4-(o-tolyl)piperidin-1-yl)-[1,2,4]triazolo[4,3-b]pyridazine A mixture of N'-(4-chloro-5-(4-(o-tolyl)piperidin-1-yl)pyridazin-3-yl)-2-cyclopropylacetohydrazide (0.25 g, 0.625 mmol) and phosphorus oxychloride (0.087 ml, 0.938 mmol) in acetonitrile (6 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(o-tolyl)piperidin-1-yl)-[1,2,4]triazolo[4,3-b]pyridazine (4.1 mg, 1.7%). $^1$H NMR (500 MHz, DMSO-$d_6$) δ 8.68 (s, 1H), 7.28 (s, 1H), 7.24-7.05 (m, 3H), 3.75 (d, J=11.9 Hz, 2H), 3.22 (d, J=5.8 Hz, 2H), 3.06-2.87 (m, 2H), 2.37 (s, 3H), 1.90-1.74 (m, 4H), 1.30-1.16 (m, 1H), 0.51 (d, J=7.0 Hz, 2H), 0.30 (d, J=4.9 Hz, 2H). LCMS (M+H)⁺=382.

Example 30

8-Chloro-3-(cyclopropylmethyl)-7-(4-(4-methoxyphenyl)piperidin-1-yl)-[1,2,4]triazolo[4,3-b]pyridazine

4-Chloro-3-hydrazinyl-5-(4-(4-methoxyphenyl)piperidin-1-yl)pyridazine

A mixture of 3,4,5-trichloropyridazine (0.250 g, 1.363 mmol), 4-(4-methoxyphenyl)piperidine (0.261 g, 1.363 mmol), and potassium carbonate (0.396 g, 2.86 mmol) in dioxane (10 ml) was heated to reflux for 1 h. The mixture was cooled and 35% hydrazine (2.469 ml, 27.3 mmol) was added. The mixture was heated to reflux for 16 h overnight. The reaction was diluted with ethyl acetate and water. The ethyl acetate layer was washed with water, dried over magnesium sulfate, and concentrated to give 4-chloro-3-hydrazinyl-5-(4-(4-methoxyphenyl)piperidin-1-yl)pyridazine as a brown oil. LCMS: Rt=2.25 min, 8%, (M−H)⁻=336, (M+H)⁺=338.

N'-(4-chloro-5-(4-(4-methoxyphenyl)piperidin-1-yl)pyridazin-3-yl)-2-cyclopropylacetohydrazide To a solution of thionyl chloride (0.273 ml, 3.74 mmol) and 2-cyclopropylacetic acid (0.077 ml, 0.824 mmol) in methylene chloride (2.5 ml) was heated to reflux for 1 h then concentrated. A solution of the residue in ethyl acetate (2.5 ml) and was added to a solution of 4-chloro-3-hydrazinyl-5-(4-(4-methoxyphenyl)piperidin-1-yl)pyridazine (0.25 g, 0.749 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give N'-(4-chloro-5-(4-(4-methoxyphenyl)piperidin-1-yl)pyridazin-3-yl)-2-cyclopropylacetohydrazide as a brown oil. LCMS: Rt=0.80 min, 18%, (M+H)⁺=416.

8-Chloro-3-(cyclopropylmethyl)-7-(4-(4-methoxyphenyl)piperidin-1-yl)-[1,2,4]triazolo[4,3-b]pyridazine A mixture of N'-(4-chloro-5-(4-(4-methoxyphenyl)piperidin-1-yl)pyridazin-3-yl)-2-cyclopropylacetohydrazide (0.250 g, 0.601 mmol) and phosphorus oxychloride (0.084 ml, 0.902 mmol) in acetonitrile (5 ml) was placed in a microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(4-methoxyphenyl)piperidin-1-yl)-[1,2,4]triazolo[4,3-b]pyridazine (4.3 mg, 1.8%). $^1$H NMR (500 MHz, DMSO-$d_6$) δ 8.67 (s, 1H), 7.24 (d, J=8.5 Hz, 2H), 6.90 (d, J=8.5 Hz, 2H), 3.79-3.67 (m, 5H), 3.18 (t, J=11.4 Hz, 2H), 3.02 (d, J=7.0 Hz, 2H), 2.71 (t, J=12.1 Hz, 1H), 1.96-1.71 (m, 4H), 1.30-1.16 (m, 1H), 0.51 (dd, J=7.9, 1.5 Hz, 2H), 0.30 (d, J=5.5 Hz, 2H). LCMS (M+H)⁺=398.

Example 31

Methyl 2-(1-(8-chloro-3-(cyclopropylmethyl)-[1,2,4]triazolo[4,3-b]pyridazin-7-yl)piperidin-4-yl)benzoate

Methyl 2-(1-(5-chloro-6-hydrazinylpyridazin-4-yl)piperidin-4-yl)benzoate

A mixture of 3,4,5-trichloropyridazine (0.250 g, 1.363 mmol), methyl 2-(piperidin-4-yl)benzoate (0.299 g, 1.363 mmol), and potassium carbonate (0.396 g, 2.86 mmol) in dioxane (10 ml) was heated to reflux for 1 h. The mixture was cooled and 35% hydrazine (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give methyl 2-(1-(5-chloro-6-hydrazinylpyridazin-4-yl)piperidin-4-yl)benzoate. LCMS: Rt=2.01 min, 9%, (M−H)⁻=360, (M+H)⁺=362.

Methyl 2-(1-(5-chloro-6-(2-(2-cyclopropylacetyl)hydrazinyl)pyridazin-4-yl)piperidin-4-yl)benzoate A solution of thionyl chloride (0.252 ml, 3.45 mmol) and 2-cyclopropylacetic acid (0.071 ml, 0.760 mmol) in methylene chloride (2.5 ml) was heated to reflux for 1 h and then concentrated. A solution of the residue in ethyl acetate (2.5 ml) was added to a solution of methyl 2-(1-(5-chloro-6-hydrazinylpyridazin-4-yl)piperidin-4-yl)benzoate (0.25 g, 0.691 mmol) in ethyl acetate (2.5 ml), THF (5 ml), and saturated sodium bicarbonate (5 ml). The mixture was stirred at room temperature for 16 h. The reaction was diluted with ethyl acetate and water. The ethyl acetate layer was washed with water and concentrated to give methyl 2-(1-(5-chloro-6-(2-(2-cyclopropylacetyl)hydrazinyl)

pyridazin-4-yl)piperidin-4-yl)benzoate. LCMS: Rt=2.06 min, 38%, (M−H)⁻=442, (M+H)⁺=444.

Methyl 2-(1-(8-chloro-3-(cyclopropylmethyl)-[1,2,4]triazolo[4,3-b]pyridazin-7-yl)piperidin-4-yl)benzoate A mixture of methyl 2-(1-(5-chloro-6-(2-(2-cyclopropylacetyl)hydrazinyl)pyridazin-4-yl)piperidin-4-yl)benzoate (0.250 g, 0.563 mmol) and phosphorus oxychloride (0.079 ml, 0.845 mmol) in acetonitrile (5 ml) was placed in a microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give methyl 2-(1-(8-chloro-3-(cyclopropylmethyl)-[1,2,4]triazolo[4,3-b]pyridazin-7-yl)piperidin-4-yl)benzoate (4.5 mg, 1.7%). $^1$H NMR (500 MHz, DMSO-$d_6$) δ 8.68 (s, 1H), 7.74 (d, J=7.3 Hz, 1H), 7.63-7.49 (m, 2H), 7.41-7.27 (m, 1H), 3.93-3.81 (m, 3H), 3.74 (d, J=12.2 Hz, 2H), 3.45 (t, J=6.9 Hz, 1H), 3.25-3.10 (m, 2H), 3.02 (d, J=6.7 Hz, 2H), 1.95-1.82 (m, 4H), 1.31-1.13 (m, 1H), 0.59-0.43 (m, 2H), 0.30 (d, J=5.8 Hz, 2H). LCMS (M+H)⁺=426.

Example 32

Methyl 2-(1-(8-chloro-3-(2,2,2-trifluoroethyl)-[1,2,4]triazolo[4,3-b]pyridazin-7-yl)piperidin-4-yl)benzoate Methyl 2-(1-(5-chloro-6-(2-(3,3,3-trifluoropropanoyl)hydrazinyl)pyridazin-4-yl)piperidin-4-yl)benzoate 3,3,3-Trifluoropropanoyl chloride (0.111 g, 0.76 mmol) was added to a solution of methyl 2-(1-(5-chloro-6-hydrazinylpyridazin-4-yl)piperidin-4-yl)benzoate (0.25 g, 0.691 mmol) in ethyl acetate (2.5 ml), THF (5 ml), and saturated sodium bicarbonate (5 ml). The mixture was stirred at room temperature for 16 h. The mixture was diluted with ethyl acetate and water. The ethyl acetate layer was separated and concentrated to a brown oil that was purified by preparative HPLC to give methyl 2-(1-(5-chloro-6-(2-(3,3,3-trifluoropropanoyl)hydrazinyl)pyridazin-4-yl)piperidin-4-yl)benzoate. LCMS: Rt=1.98 min, 61%, (M−H)⁻=470, (M+H)⁺=472.

Methyl 2-(1-(8-chloro-3-(2,2,2-trifluoroethyl)-[1,2,4]triazolo[4,3-b]pyridazin-7-yl)piperidin-4-yl)benzoate A mixture of methyl 2-(1-(5-chloro-6-(2-(3,3,3-trifluoropropanoyl)hydrazinyl)pyridazin-4-yl)piperidin-4-yl)benzoate (0.250 g, 0.530 mmol) and phosphorus oxychloride (0.074 ml, 0.795 mmol) in acetonitrile (5 ml) was placed in a microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give methyl 2-(1-(8-chloro-3-(2,2,2-trifluoroethyl)-[1,2,4]triazolo[4,3-b]pyridazin-7-yl)piperidin-4-yl)benzoate (0.7 mg, 0.3%). $^1$H NMR (500 MHz, METHANOL-$d_4$) δ 8.65 (s, 1H), 7.80 (d, J=7.6 Hz, 1H), 7.59-7.49 (m, 2H), 7.32 (ddd, J=8.0, 5.4, 3.1 Hz, 1H), 4.23 (q, J=10.3 Hz, 2H), 3.98-3.88 (m, 5H), 3.72-3.59 (m, 1H), 3.38-3.22 (m, 2H), 2.08-1.97 (m, 4H). LCMS (M+H)⁺=454.

Example 33

8-Chloro-3-(cyclopropylmethyl)-N-((2,3-dihydro-1H-inden-2-yl)methyl)-[1,2,4]triazolo[4,3-b]pyridazin-7-amine 5-Chloro-N-((2,3-dihydro-1H-inden-2-yl)methyl)-6-hydrazinylpyridazin-4-amine A mixture of 3,4,5-trichloropyridazine (0.250 g, 1.363 mmol), (2,3-dihydro-1H-inden-2-yl)methanamine hydrochloride (0.250 g, 1.363 mmol), and potassium carbonate (0.396 g, 2.86 mmol) in dioxane (10 ml) was heated to reflux for 1 h. The mixture was cooled and 35% hydrazine (2.469 ml, 27.3 mmol) was added. The mixture was heated to reflux for 16 h overnight. The reaction was diluted with ethyl acetate and water. The ethyl acetate layer was washed with water, dried over magnesium sulfate, and concentrated to give 5-chloro-N-((2,3-dihydro-1H-inden-2-yl)methyl)-6-hydrazinylpyridazin-4-amine LCMS: Rt=1.85 min, (M+H)⁺=290.1. The material was used without purification.

N'-(4-Chloro-5-(((2,3-dihydro-1H-inden-2-yl)methyl)amino)pyridazin-3-yl)-2-cyclopropylacetohydrazide A solution of thionyl chloride (0.315 ml, 4.31 mmol) and 2-cyclopropylacetic acid (0.088 ml, 0.949 mmol) in methylene chloride (2.5 ml) was heated to reflux for 1 h and then concentrated. A solution of the reside in ethyl acetate (2.5 ml) was added to a mixture of 5-chloro-N-((2,3-dihydro-1H-inden-2-yl)methyl)-6-hydrazinylpyridazin-4-amine (0.25 g, 0.863 mmol) in ethyl acetate (2.5 ml), THF (5 ml), and saturated sodium bicarbonate (5 ml). The mixture was stirred at room temperature for 16 h. The mixture was diluted with ethyl acetate and water. The ethyl acetate layer was separated and concentrated to a brown oil that was purified by preparative HPLC to give N'-(4-chloro-5-(((2,3-dihydro-1H-inden-2-yl)methyl)amino)pyridazin-3-yl)-2-cyclopropylacetohydrazide. LCMS: Rt=1.94 min, 18%, (M−H)⁻=370, (M+H)⁺=372.

8-Chloro-3-(cyclopropylmethyl)-N-((2,3-dihydro-1H-inden-2-yl)methyl)-[1,2,4]triazolo[4,3-b]pyridazin-7-amine A mixture of N'-(4-chloro-5-(((2,3-dihydro-1H-inden-2-yl)methyl)amino)pyridazin-3-yl)-2-cyclopropylacetohydrazide (0.250 g, 0.672 mmol) and phosphorus oxychloride (0.094 ml, 1 mmol) in acetonitrile (5 ml) was placed in a microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-N-((2,3-dihydro-1H-inden-2-yl)methyl)-[1,2,4]triazolo[4,3-b]pyridazin-7-amine (8.7 mg, 3.7%). $^1$H NMR (500 MHz, DMSO-$d_6$) δ 8.65 (s, 1H), 7.22 (dd, J=5.2, 3.4 Hz, 2H), 7.13 (dd, J=5.5, 3.1 Hz, 2H), 6.78 (t, J=6.3 Hz, 1H), 3.49 (t, J=6.7 Hz, 2H), 3.08-2.90 (m, 4H), 2.83-2.67 (m, 3H), 1.26-1.14 (m, 1H), 0.49 (dd, J=8.1, 1.7 Hz, 2H), 0.28 (d, J=5.8 Hz, 2H). LCMS (M+H)⁺=354.

Example 34

3-(Cyclopropylmethyl)-7-(4-(2-fluoro-6-methoxyphenyl)piperidin-1-yl)-[1,2,4]triazolo[4,3-c]pyrimidine

4-(4-(2-Fluoro-6-methoxyphenyl)piperidin-1-yl)-6-hydrazinylpyrimidine

A mixture of 4,6-dichloropyrimidine (1 g, 6.7 mmol), 4-(2-fluoro-6-methoxyphenyl)piperidine (1.405 g, 6.7 mmol), and potassium carbonate (1.948 g, 14.1 mmol) in dioxane (50 ml) was heated to reflux for 1 h. The mixture was cooled and 35% hydrazine in water (12.16 ml, 134 mmol) was added. The mixture was heated to reflux for 16 h overnight. The reaction was diluted with ethyl acetate and water. The ethyl acetate layer was washed with water, dried over magnesium sulfate, and concentrated to give 4-(4-(2-fluoro-6-methoxyphenyl) piperidin-1-yl)-6-hydrazinylpyrimidine (2.22 g, 100%) as a white crytalline solid. $(M+H)^+$= 318.3 at 1.96 min.

2-Cyclopropyl-N'-(6-(4-(2-fluoro-6-methoxyphenyl)piperidin-1-yl)pyrimidin-4-yl)acetohydrazide A solution of thionyl chloride (2.55 ml, 35 mmol) and 2-cyclopropylacetic acid (0.716 ml, 7.69 mmol) in methylene chloride (25 ml) was heated to reflux for 1 h and then concentrated. A solution of the residue in ethyl acetate (25 ml) was added to a solution of 4-(4-(2-fluoro-6-methoxyphenyl)piperidin-1-yl)-6-hydrazinylpyrimidine (2.22 g, 7 mmol) in ethyl acetate (25 ml), THF (50 ml), and saturated sodium bicarbonate) (5 ml). The mixture was stirred at room temperature for 16 h. The mixture was diluted with ethyl acetate and water. The ethyl acetate layer was separated and concentrated to a grey solid that was purified by preparative HPLC to give 2-cyclopropyl-N'-(6-(4-(2-fluoro-6-methoxyphenyl)piperidin-1-yl)pyrimidin-4-yl)acetohydrazide (2.1 g, 75%). $^1$H NMR (500 MHz, METHANOL-$d_4$) δ 8.09 (d, J=0.9 Hz, 1H), 7.17 (td, J=8.4, 6.6 Hz, 1H), 6.78 (d, J=8.4 Hz, 1H), 6.66 (ddd, J=10.8, 8.4, 1.0 Hz, 1H), 5.85 (d, J=0.8 Hz, 1H), 4.45 (d, J=13.6 Hz, 2H), 3.90-3.77 (m, 4H), 3.54-3.43 (m, 1H), 3.05-2.88 (m, 2H), 2.25-1.99 (m, 4H), 1.66 (d, J=10.1 Hz, 2H), 1.18-1.06 (m, 1H), 0.64-0.51 (m, 2H), 0.34-0.20 (m, 2H).

3-(Cyclopropylmethyl)-7-(4-(2-fluoro-6-methoxyphenyl)piperidin-1-yl)-[1,2,4]triazolo[4,3-c]pyrimidine A mixture of 2-cyclopropyl-N'-(6-(4-(2-fluoro-6-methoxyphenyl)piperidin-1-yl)pyrimidin-4-yl)acetohydrazide (1.0 g, 2.5 mmol) and phosphorus oxychloride (0.35 ml, 3.76 mmol) in acetonitrile (20 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 3-(cyclopropylmethyl)-7-(4-(2-fluoro-6-methoxyphenyl)piperidin-1-yl)-[1,2,4]triazolo[4,3-c]pyrimidine. $^1$H NMR (500 MHz, METHANOL-$d_4$) δ 9.11-8.91 (m, 1H), 7.17 (td, J=8.3, 6.6 Hz, 1H), 6.87-6.74 (m, 1H), 6.73-6.60 (m, 1H), 6.46-6.35 (m, 1H), 4.67-4.45 (m, 2H), 3.83 (s, 3H), 3.58-3.42 (m, 1H), 3.07 (d, J=6.7 Hz, 3H), 2.76-2.60 (m, 1H), 2.37-2.13 (m, 2H), 1.79-1.64 (m, 2H), 1.37-1.10 (m, 1H), 0.73-0.51 (m, 2H), 0.45-0.23 (m, 2H). LCMS $(M+H)^+$=382.

Example 35

8-Chloro-3-(cyclopropylmethyl)-7-(4-(2,5-dimethoxyphenyl)piperidin-1-yl)-[1,2,4]triazolo[4,3-b]pyridazine

4-Chloro-5-(4-(2,5-dimethoxyphenyl)piperidin-1-yl)-3-hydrazinylpyridazine

A mixture of 3,4,5-trichloropyridazine (0.5 g, 2.73 mmol), 4-(2,5-dimethoxyphenyl)piperidine hydrochloride (0.703 g, 2.73 mmol), and potassium carbonate (0.791 g, 5.72 mmol) in dioxane (10 ml) was heated to reflux for 1 h. The mixture was cooled and 35% hydrazine in water (2.469 ml, 27.3 mmol) was added and the mixture was heated to reflux for 16 h. The reaction was diluted with ethyl acetate and water. The ethyl acetate layer was washed with water, dried over magnesium sulfate, and concentrated to give 4-chloro-5-(4-(2,5-dimethoxyphenyl)piperidin-1-yl)-3-hydrazinylpyridazine as a brown oil. $(M+H)^+$=364.2.

N'-(4-Chloro-5-(4-(2,5-dimethoxyphenyl)piperidin-1-yl)pyridazin-3-yl)-2-cyclopropylacetohydrazide A solution of thionyl chloride (0.251 ml, 3.44 mmol) and 2-cyclopropylacetic acid (0.070 ml, 0.756 mmol) in methylene chloride (2.5 ml) was heated to reflux for 1 h then concentrated. A solution of the residue in ethyl acetate (2.5 ml) was added to a solution of 4-chloro-5-(4-(2,5-dimethoxyphenyl)piperidin-1-yl)-3-hydrazinylpyridazine (0.25 g, 0.687 mmol) in ethyl acetate (2.5 ml), THF (5 ml), and saturated sodium bicarbonate (5 ml). The mixture was stirred for 16 h. The mixture was diluted with ethyl acetate and water. The ethyl acetate layer was separated and concentrated to a grey solid that was purified by preparative HPLC to give N'-(4-chloro-5-(4-(2,5-dimethoxyphenyl)piperidin-1-yl)pyridazin-3-yl)-2-cyclopropylacetohydrazide. $(M+H)^+$=446.2.

8-Chloro-3-(cyclopropylmethyl)-7-(4-(2,5-dimethoxyphenyl)piperidin-1-yl)-[1,2,4]triazolo[4,3-b]pyridazine A mixture of N'-(4-chloro-5-(4-(2,5-dimethoxyphenyl)piperidin-1-yl)pyridazin-3-yl)-2-cyclopropylacetohydrazide (0.25 g, 0.561 mmol) and phosphorus oxychloride (0.078 ml, 0.841 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(2,5-dimethoxyphenyl)piperidin-1-yl)-[1,2,4]triazolo[4,3-b]pyridazine (40 mg, 16.3%). $^1$H NMR (500 MHz, DMSO-$d_6$) δ 8.67 (s, 1H), 6.93 (d, J=8.9 Hz, 1H), 6.86-6.71 (m, 2H), 3.82-3.65 (m, 6H), 3.25-3.14 (m, 2H), 3.08 (dq, J=10.6, 5.2 Hz, 1H), 3.02 (d, J=7.0 Hz, 1H), 2.53-2.50 (m, 6H), 1.84 (dd, J=9.3, 3.8 Hz, 3H), 1.26-1.19 (m, 1H), 0.53-0.48 (m, 1H), 0.32-0.28 (m, 1H). LCMS $(M+H)^+$=428.2.

Example 36

8-Chloro-7-(4-(2,5-dimethoxyphenyl)piperidin-1-yl)-3-(2,2,2-trifluoroethyl)-[1,2,4]triazolo[4,3-b]pyridazine

N'-(4-Chloro-5-(4-(2,5-dimethoxyphenyl)piperidin-1-yl)pyridazin-3-yl)-3,3,3-trifluoropropanehydrazide 3,3,3-Trifluoropropanoyl chloride (0.111 g, 0.756 mmol) was added to a solution of 4-chloro-5-(4-(2,5-dimethoxyphenyl)piperidin-1-yl)-3-hydrazinylpyridazine (0.250 g, 0.687 mmol) in ethyl acetate (2.500 ml), THF (5 ml), and saturated sodium bicarbonate (5 ml) and the mixture was stirred for 16 h. The mixture was diluted with ethyl acetate and water. The ethyl acetate layer was separated and concentrated to give N'-(4-chloro-5-(4-(2,5-dimethoxyphenyl)piperidin-1-yl)pyridazin-3-yl)-3,3,3-trifluoropropanehydrazide as a brown oil. (M+H)$^+$=474.2.

8-Chloro-7-(4-(2,5-dimethoxyphenyl)piperidin-1-yl)-3-(2,2,2-trifluoroethyl)-[1,2,4]triazolo[4,3-b]pyridazine A mixture of N'-(4-chloro-5-(4-(2,5-dimethoxyphenyl)piperidin-1-yl)pyridazin-3-yl)-3,3,3-trifluoropropanehydrazide (0.25 g, 0.528 mmol) and phosphorus oxychloride (0.074 ml, 0.791 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-7-(4-(2,5-dimethoxyphenyl)piperidin-1-yl)-3-(2,2,2-trifluoroethyl)-[1,2,4]triazolo[4,3-b]pyridazine (2.2 mg, 0.9%). $^1$H NMR (500 MHz, DMSO-d$_6$) δ 8.76 (s, 1H), 6.93 (d, J=8.9 Hz, 1H), 6.84-6.69 (m, 2H), 4.36 (q, J=10.7 Hz, 2H), 3.83-3.75 (m, 6H), 3.25-3.02 (m, 5H), 1.89-1.76 (m, 4H). LCMS: Rt=2.03 min, (M+H)$^+$=456.2, (M+NH4)+=472.3.

Example 37

8-Chloro-3-(cyclopropylmethyl)-7-(4-(2,4-dimethoxyphenyl)piperidin-1-yl)-[1,2,4]triazolo[4,3-b]pyridazine 4-Chloro-5-(4-(2,4-dimethoxyphenyl)piperidin-1-yl)-3-hydrazinylpyridazine A mixture of 3,4,5-trichloropyridazine (0.5 g, 2.73 mmol), 4-(2,4-dimethoxyphenyl)piperidine hydrochloride (0.703 g, 2.73 mmol), and potassium carbonate (0.791 g, 5.72 mmol) in dioxane (10 ml) was heated to reflux for 1 h. One drop of water was added and stirred at 100° C. for 16 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 4-chloro-5-(4-(2,4-dimethoxyphenyl)piperidin-1-yl)-3-hydrazinylpyridazine as a brown oil. (M+H)$^+$=364.2.

N'-(4-Chloro-5-(4-(2,4-dimethoxyphenyl)piperidin-1-yl)pyridazin-3-yl)-2-cyclopropylacetohydrazide A solution of thionyl chloride (0.251 ml, 3.44 mmol) and 2-cyclopropylacetic acid (0.070 ml, 0.756 mmol) in methylene chloride (2.5 ml) was heated to reflux for 1 h and then concentrated. A solution of the residue in ethyl acetate (2.5 ml) was added to a solution of 4-chloro-5-(4-(2,4-dimethoxyphenyl)piperidin-1-yl)-3-hydrazinylpyridazine (0.25 g, 0.687 mmol) in ethyl acetate (2.5 ml), THF (5 ml), and saturated sodium bicarbonate (5 ml). The mixture was stirred at room temperature for 16 h. The mixture was diluted with ethyl acetate and water. The ethyl acetate layer was separated and concentrated to give N'-(4-chloro-5-(4-(2,4-dimethoxyphenyl)piperidin-1-yl)pyridazin-3-yl)-2-cyclopropylacetohydrazide. (M+H)$^+$=446.3.

8-Chloro-3-(cyclopropylmethyl)-7-(4-(2,4-dimethoxyphenyl)piperidin-1-yl)-[1,2,4]triazolo[4,3-b]pyridazine A mixture of N'-(4-chloro-5-(4-(2,4-dimethoxyphenyl)piperidin-1-yl)pyridazin-3-yl)-2-cyclopropylacetohydrazide (0.25 g, 0.561 mmol) and phosphorus oxychloride (0.078 ml, 0.841 mmol) in acetonitrile (5 ml) was heated to 80° C. for 16 h. The mixture was diluted with ethyl acetate and water. The ethyl acetate layer was separated and concentrated to a brown oil that was purified by preparative HPLC to give 8-chloro-3-(cyclopropylmethyl)-7-(4-(2,4-dimethoxyphenyl)piperidin-1-yl)-[1,2,4]triazolo[4,3-b]pyridazine (29.2 mg, 12%). $^1$H NMR (500 MHz, DMSO-d$_6$) δ 8.66 (s, 1H), 7.14 (d, J=8.2 Hz, 1H), 6.60-6.44 (m, 2H), 3.86-3.64 (m, 8H), 3.26-3.13 (m, 2H), 3.02 (d, J=7.0 Hz, 3H), 1.89-1.70 (m, 4H), 1.29-1.17 (m, 1H), 0.51 (dd, J=7.9, 1.5 Hz, 2H), 0.30 (d, J=5.8 Hz, 2H). (M+H)$^+$=428.3.

Example 38

8-Chloro-7-(4-(2,4-dimethoxyphenyl)piperidin-1-yl)-3-(2,2,2-trifluoroethyl)-[1,2,4]triazolo[4,3-b]pyridazine N'-(4-Chloro-5-(4-(2,4-dimethoxyphenyl)piperidin-1-yl)pyridazin-3-yl)-3,3,3-trifluoropropanehydrazide 3,3,3-Trifluoropropanoyl chloride (0.111 g, 0.756 mmol) was added to a solution of 4-chloro-5-(4-(2,4-dimethoxyphenyl)piperidin-1-yl)-3-hydrazinylpyridazine (0.25 g, 0.687 mmol) in ethyl acetate (2.5 ml), THF (5 ml), and saturated sodium bicarbonate (5 ml). The mixture was stirred at room temperature for 16 h. The mixture was diluted with ethyl acetate and water. The ethyl acetate layer was separated and concentrated to give N'-(4-chloro-5-(4-(2,4-dimethoxyphenyl)piperidin-1-yl)pyridazin-3-yl)-3,3,3-trifluoropropanehydrazide. [M+H+]=476.2.

8-Chloro-7-(4-(2,4-dimethoxyphenyl)piperidin-1-yl)-3-(2,2,2-trifluoroethyl)-[1,2,4]triazolo[4,3-b]pyridazine A mixture of N'-(4-chloro-5-(4-(2,4-dimethoxyphenyl)piperidin-1-yl)pyridazin-3-yl)-3,3,3-trifluoropropanehydrazide (0.25 g, 0.528 mmol) and phosphorus oxychloride (0.074 ml, 0.791 mmol) in acetonitrile (5 ml) was heated to 80° C. for 16 h. The mixture was cooled and diluted with ethyl acetate and water. The ethyl acetate layer was separated and concentrated to a brown oil that was purified by preparative HPLC to give 8-chloro-7-(4-(2,4-dimethoxyphenyl)piperidin-1-yl)-3-(2,2,2-trifluoroethyl)-[1,2,4]triazolo[4,3-b]pyridazine (1.2 mg, 0.5%). $^1$H NMR (500 MHz, DMSO-d$_6$) δ 8.76 (s, 1H), 7.14 (d, J=8.2 Hz, 1H), 6.63-6.44 (m, 2H), 4.35 (q, J=10.7 Hz, 2H), 3.86-3.68 (m, 8H), 3.27-3.14 (m, 2H), 3.08-2.94 (m, 1H), 1.91-1.67 (m, 4H). (M+H)$^+$=456.5.

Example 39

8-Chloro-3-(cyclopropylmethyl)-N-((2-(2-fluoro-6-methoxyphenyl)cyclopropyl)methyl)-[1,2,4]triazolo[4,3-b]pyridazin-7-amine 5-Chloro-N-((2-(2-fluoro-6-methoxyphenyl)cyclopropyl)methyl)-6-hydrazinylpyridazin-4-amine A mixture of 3,4,5-trichloropyridazine (0.25 g, 1.363 mmol), (2-(2-fluoro-6-methoxyphenyl)cyclopropyl)methanamine (0.266 g, 1.363 mmol), and potassium carbonate (0.396 g, 2.86 mmol) in dioxane (10 ml) was heated to reflux for 16 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 5-chloro-N-((2-(2-fluoro-6-methoxyphenyl)cyclopropyl)methyl)-6-hydrazinylpyridazin-4-amine as a brown oil. (M+H)$^+$=338.1.

N'-(4-chloro-5-(((2-(2-fluoro-6-methoxyphenyl)cyclopropyl)methyl)amino)pyridazin-3-yl)-2-cyclopropylacetohydrazide A solution of thionyl chloride (0.27 ml, 3.70 mmol) and 2-cyclopropylacetic acid (0.076 ml, 0.814 mmol) in methylene chloride (2.5 ml) was heated to reflux for 1 h and then concentrated. A solution of the residue in ethyl acetate (2.5 ml) was added to a solution of 5-chloro-N-((2-(2-fluoro-6-methoxyphenyl)cyclopropyl)methyl)-6-hydrazinylpyridazin-4-amine (0.25 g, 0.74 mmol) in ethyl acetate (2.500 ml), THF (5.00 ml), and saturated sodium bicarbonate (5 ml) and was stirred at room temperature for 16 h. The mixture was diluted with ethyl acetate and water. The ethyl acetate layer was separated and concentrated to give N'-(4-chloro-5-(((2-(2-fluoro-6-methoxyphenyl)cyclopropyl)methyl)amino) pyridazin-3-yl)-2-cyclopropylacetohydrazide. (M+H)$^+$=420.3.

8-Chloro-3-(cyclopropylmethyl)-N-((2-(2-fluoro-6-methoxyphenyl)cyclopropyl)methyl)-[1,2,4]triazolo[4,3-b]pyridazin-7-amine A mixture of N'-(4-chloro-5-(((2-(2-fluoro-6-methoxyphenyl)cyclopropyl)methyl)amino)pyridazin-3-yl)-2-cyclopropylacetohydrazide (0.250 g, 0.595 mmol) and phosphorus oxychloride (0.083 ml, 0.893 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-N-((2-(2-fluoro-6-methoxyphenyl)cyclopropyl)methyl)-[1,2,4]triazolo[4,3-b]pyridazin-7-amine (2.1 mg, 0.9%). $^1$H NMR (500 MHz, DMSO-d$_6$) δ 8.66 (s, 1H), 7.21-7.09 (m, 1H), 6.84-6.56 (m, 3H), 3.73 (s, 3H), 3.70-3.59 (m, 1H), 3.47-3.38 (m, 1H), 2.96 (d, J=7.0 Hz, 2H), 1.88-1.74 (m, 1H), 1.64-1.49 (m, 1H), 1.28-1.14 (m, 1H), 1.11-1.02 (m, 1H), 0.99-0.90 (m, 1H), 0.54-0.43 (m, 2H), 0.34-0.22 (m, 2H). LCMS (M+H)$^+$=402.2.

Example 40

8-Chloro-N-((2-(2-fluoro-6-methoxyphenyl)cyclopropyl)methyl)-3-(2,2,2-trifluoroethyl)-[1,2,4]triazolo[4,3-b]pyridazin-7-amine

N'-(4-Chloro-5-(((2-(2-fluoro-6-methoxyphenyl)cyclopropyl)methyl)amino)pyridazin-3-yl)-3,3,3-trifluoropropanehydrazide 3,3,3-Trifluoropropanoyl chloride (0.119 g, 0.814 mmol) was added to a solution of 5-chloro-N-((2-(2-fluoro-6-methoxyphenyl)cyclopropyl)methyl)-6-hydrazinylpyridazin-4-amine (0.25 g, 0.740 mmol) in ethyl acetate (2.5 ml), THF (5.00 ml), and saturated sodium bicarbonate (5 ml) and was stirred at room temperature for 16 h. The mixture was diluted with ethyl acetate and water. The ethyl acetate layer was separated and concentrated to give N'-(4-chloro-5-(((2-(2-fluoro-6-methoxyphenyl)cyclopropyl)methyl)amino)pyridazin-3-yl)-3,3,3-trifluoropropanehydrazide as a brown oil. (M+H)$^+$=448.2.

8-Chloro-N-((2-(2-fluoro-6-methoxyphenyl)cyclopropyl)methyl)-3-(2,2,2-trifluoroethyl)-[1,2,4]triazolo[4,3-b]pyridazin-7-amine A mixture of N'-(4-chloro-5-(((2-(2-fluoro-6-methoxyphenyl)cyclopropyl)methyl)amino)pyridazin-3-yl)-3,3,3-trifluoropropanehydrazide (0.250 g, 0.558 mmol) and phosphorus oxychloride (0.078 ml, 0.837 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-N-((2-(2-fluoro-6-methoxyphenyl)cyclopropyl)methyl)-3-(2,2,2-trifluoroethyl)-[1,2,4]triazolo[4,3-b]pyridazin-7-amine (1.1 mg, 0.5%). $^1$H NMR (500 MHz, DMSO-d$_6$) δ 8.77 (s, 1H), 7.25-7.08 (m, 1H), 6.90-6.60 (m, 3H), 4.29 (q, J=10.7 Hz, 2H), 3.71 (s, 5H), 1.88-1.73 (m, 1H), 1.63-1.49 (m, 1H), 1.13-1.01 (m, 1H), 1.00-0.88 (m, 1H). LCMS (M+H)$^+$=430.2.

Example 41

8-Chloro-3-(cyclopropylmethyl)-7-(4-(pyridin-4-yl)piperidin-1-yl)-[1,2,4]triazolo[4,3-b]pyridazine

4-Chloro-3-hydrazinyl-5-(4-(pyridin-4-yl)piperidin-1-yl)pyridazine

A mixture of 3,4,5-trichloropyridazine (0.5 g, 2.73 mmol), 4-(piperidin-4-yl)pyridine (0.442 g, 2.73 mmol), and potassium carbonate (0.791 g, 5.72 mmol) in dioxane (10 ml) was heated to reflux for 16 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 4-chloro-3-hydrazinyl-5-(4-(pyridin-4-yl)piperidin-1-yl)pyridazine as a brown oil. (M+H)$^+$=305.1.

N'-(4-Chloro-5-(4-(pyridin-4-yl)piperidin-1-yl)pyridazin-3-yl)-2-cyclopropylacetohydrazide A solution of thionyl chloride (0.299 ml, 4.10 mmol) and 2-cyclopropylacetic acid (0.084 ml, 0.902 mmol) in methylene chloride (2.5 ml) was heated to reflux for 1 h then concentrated. A solution of the residue in ethyl acetate (2.5 ml) was added to a solution of 4-chloro-3-hydrazinyl-5-(4-(pyridin-4-yl)piperidin-1-yl)pyridazine (0.25 g, 0.82 mmol) in ethyl acetate (2.5 ml), THF (5 ml), and saturated sodium bicarbonate (5 ml) and stirred at room temperature for 16 h. The mixture was diluted with ethyl acetate and water. The ethyl acetate layer was separated and concentrated to give N'-(4-chloro-5-(4-(pyridin-4-yl)piperidin-1-yl)pyridazin-3-yl)-2-cyclopropylacetohydrazide as a brown oil. (M+H)$^+$=387.3.

8-Chloro-3-(cyclopropylmethyl)-7-(4-(pyridin-4-yl)piperidin-1-yl)-[1,2,4]triazolo[4,3-b]pyridazine A mixture of N'-(4-chloro-5-(4-(pyridin-4-yl)piperidin-1-yl)pyridazin-3-yl)-2-cyclopropylacetohydrazide (0.25 g, 0.646 mmol) and phosphorus oxychloride (0.09 ml, 0.969 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(pyridin-4-yl)piperidin-1-yl)-[1,2,4]triazolo[4,3-b]pyridazine (18.5 mg, 7.8%). (M+H)$^+$=369.3 at 1.94 min. $^1$H NMR (500 MHz, DMSO-d$_6$) δ 8.67 (s, 1H), 8.52 (d, J=4.9 Hz, 2H), 7.36 (d, J=4.9 Hz, 2H), 3.75 (d, J=12.5 Hz, 2H), 3.20 (t, J=11.6 Hz, 2H), 3.02 (d, J=6.7 Hz, 2H), 2.82 (t, J=12.1 Hz, 1H), 2.03-1.75 (m, 4H), 1.30-1.15 (m, 1H), 0.51 (d, J=7.9 Hz, 2H), 0.30 (d, J=4.9 Hz, 2H). LCMS (M+H)$^+$=369.2.

Example 42

8-Chloro-3-(cyclopropylmethyl)-7-(4-(4,6-dimethoxypyrimidin-2-yl)piperidin-1-yl)-[1,2,4]triazolo[4,3-b]pyridazine 4-Chloro-5-(4-(4,6-dimethoxypyrimidin-2-yl)piperidin-1-yl)-3-hydrazinylpyridazine A mixture of 3,4,5-trichloropyridazine (0.5 g, 2.73 mmol), 4,6-dimethoxy-2-(piperidin-4-yl)pyrimidine (0.609 g, 2.73 mmol), and potassium carbonate (0.791 g, 5.72 mmol) in dioxane (10 ml) was heated to reflux for 16 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 4-chloro-5-(4-(4,6-dimethoxypyrimidin-2-yl)piperidin-1-yl)-3-hydrazinylpyridazine as a brown oil. (M+H)$^+$=366.2.

N'-(4-Chloro-5-(4-(4,6-dimethoxypyrimidin-2-yl)piperidin-1-yl)pyridazin-3-yl)-2-cyclopropylacetohydrazide A solution of thionyl chloride (0.249 ml, 3.42 mmol) and 2-cyclopropylacetic acid (0.07 ml, 0.752 mmol) in methylene chloride (2.5 ml) was heated to reflux for 1 h and then concentrated. A solution of the residue in ethyl acetate (2.5 ml) was added to a solution of 4-chloro-5-(4-(4,6-dimethoxypyrimidin-2-yl)piperidin-1-yl)-3-hydrazinylpyridazine (0.25 g, 0.683 mmol) in ethyl acetate (2.5 ml), THF (5 ml), and saturated sodium bicarbonate (5 ml) and was stirred at room temperature for 16 h. The mixture was diluted with ethyl acetate and water. The ethyl acetate layer was separated and concentrated to give N'-(4-chloro-5-(4-(4,6-dimethoxypyrimidin-2-yl)piperidin-1-yl)pyridazin-3-yl)-2-cyclopropylacetohydrazide as a brown oil. (M+H)$^+$=448.3.

8-Chloro-3-(cyclopropylmethyl)-7-(4-(4,6-dimethoxypyrimidin-2-yl)piperidin-1-yl)-[1,2,4]triazolo[4,3-b]pyridazine A mixture of N'-(4-chloro-5-(4-(4,6-dimethoxypyrimidin-2-yl)piperidin-1-yl)pyridazin-3-yl)-2-cyclopropylacetohydrazide (0.250 g, 0.558 mmol) and phosphorus oxychloride (0.078 ml, 0.837 mmol) in acetonitrile (5 ml) was placed in a microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(4,6-dimethoxypyrimidin-2-yl)piperidin-1-yl)-[1,2,4]triazolo[4,3-b]pyridazine as a brown oil (13.2 mg, 5.5%). $^1$H NMR (500 MHz, DMSO-d$_6$) δ 8.66 (s, 1H), 6.11 (s, 1H), 3.91 (s, 6H), 3.71 (d, J=12.5 Hz, 2H), 3.21 (t, J=10.8 Hz, 2H), 3.02 (d, J=6.7 Hz, 2H), 2.94-2.84 (m, 1H), 2.10 (d, J=11.0 Hz, 2H), 2.04-1.87 (m, 2H), 1.30-1.13 (m, 1H), 0.57-0.43 (m, 2H), 0.30 (d, J=5.2 Hz, 2H). LCMS (M+H)$^+$=430.2.

Example 43

8-Chloro-7-(4-(4,6-dimethoxypyrimidin-2-yl)piperidin-1-yl)-3-(2,2,2-trifluoroethyl)-[1,2,4]triazolo[4,3-b]pyridazine N'-(4-Chloro-5-(4-(4,6-dimethoxypyrimidin-2-yl)piperidin-1-yl)pyridazin-3-yl)-3,3,3-trifluoropropanehydrazide 3,3,3-Trifluoropropanoyl chloride (0.11 g, 0.752 mmol) was added to a solution of 4-chloro-5-(4-(4,6-dimethoxypyrimidin-2-yl)piperidin-1-yl)-3-hydrazinylpyridazine (0.25 g, 0.683 mmol) in ethyl acetate (2.5 ml), THF (5 ml), and saturated sodium bicarbonate (5 ml) and was stirred at room temperature for 16 h. The mixture was diluted with ethyl acetate and water. The ethyl acetate layer was separated and concentrated to give N'-(4-chloro-5-(4-(4,6-dimethoxypyrimidin-2-yl)piperidin-1-yl)pyridazin-3-yl)-3,3,3-trifluoropropanehydrazide as a brown oil. (M+H)$^+$=476.2.

8-Chloro-7-(4-(4,6-dimethoxypyrimidin-2-yl)piperidin-1-yl)-3-(2,2,2-trifluoroethyl)-[1,2,4]triazolo[4,3-b]pyridazine A mixture of N'-(4-chloro-5-(4-(4,6-dimethoxypyrimidin-2-yl)piperidin-1-yl)pyridazin-3-yl)-3,3,3-trifluoropropanehydrazide (0.25 g, 0.525 mmol) and phosphorus oxychloride (0.073 ml, 0.788 mmol) in acetonitrile (5 ml) heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-7-(4-(4,6-dimethoxypyrimidin-2-yl)piperidin-1-yl)-3-(2,2,2-trifluoroethyl)-[1,2,4]triazolo[4,3-b]pyridazine (5.4 mg, 2.25%) as a brown oil. $^1$H NMR (500 MHz, DMSO-d$_6$) δ 8.75 (s, 1H), 6.11 (s, 1H), 4.35 (q, J=10.7 Hz, 2H), 3.91 (s, 6H), 3.76 (d, J=12.2 Hz, 2H), 3.30-3.18 (m, 2H), 2.98-2.82 (m, 1H), 2.11 (d, J=10.4 Hz, 2H), 2.03-1.89 (m, 2H). LCMS (M+H)$^+$=458.2.

Example 44

8-Chloro-7-(4-(2-chlorophenyl)piperidin-1-yl)-3-(cyclopropylmethyl)-[1,2,4]triazolo[4,3-b]pyridazine 4-Chloro-5-(4-(2-chlorophenyl)piperidin-1-yl)-3-hydrazinylpyridazine A mixture of 3,4,5-trichloropyridazine (0.25 g, 1.363 mmol), 4-(2-chlorophenyl)piperidine, 4-methylbenzenesulfonate salt (0.5 g, 1.363 mmol), and potassium carbonate (0.396 g, 2.86 mmol) in dioxane (5 ml) was heated to reflux for 1 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 4-chloro-5-(4-(2-chlorophenyl)piperidin-1-yl)-3-hydrazinylpyridazine as a brown oil. (M+H)$^+$=338.1.

N'-(4-Chloro-5-(4-(2-chlorophenyl)piperidin-1-yl)pyridazin-3-yl)-2-cyclopropylacetohydrazide A solution of thionyl chloride (0.135 ml, 1.848 mmol) and 2-cyclopropylacetic acid (0.038 ml, 0.407 mmol) in methylene chloride (1.5 ml) was heated to reflux for 1 h and then concentrated. A solution of the residue in ethyl acetate (1.5 ml) was added to a solution of 4-chloro-5-(4-(2-chlorophenyl)piperidin-1-yl)-3-hydrazinylpyridazine (0.125 g, 0.37 mmol) in ethyl acetate (1.5 ml), THF (3 ml), and saturated sodium bicarbonate (3 ml). The mixture was stirred at room temperature for 16 h. The mixture was diluted with ethyl acetate and water. The ethyl acetate layer was separated and concentrated to give N'-(4-chloro-5-(4-(2-chlorophenyl)piperidin-1-yl)pyridazin-3-yl)-2-cyclopropylacetohydrazide as a brown oil. (M+H)$^+$=420.3.

8-Chloro-7-(4-(2-chlorophenyl)piperidin-1-yl)-3-(cyclopropylmethyl)-[1,2,4]triazolo[4,3-b]pyridazine A mixture of N'-(4-chloro-5-(4-(2-chlorophenyl)piperidin-1-yl)pyridazin-3-yl)-2-cyclopropylacetohydrazide (0.125 g, 0.297 mmol) and phosphorus oxychloride (0.042 ml, 0.446 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-7-(4-(2-chlorophenyl)piperidin-1-yl)-3-(cyclopropylmethyl)-[1,2,4]triazolo[4,3-b]pyridazine as a brown oil (4.4 mg, 3.6%). $^1$H NMR (500 MHz, DMSO-d$_6$) δ 8.68 (s, 1H), 7.51-7.33 (m, 3H), 7.33-7.22 (m, 1H), 3.76 (d, J=12.5 Hz, 2H), 3.28-3.13 (m, 3H), 3.02 (d, J=6.7 Hz, 2H), 2.00-1.79 (m, 4H), 1.22 (d, J=7.3 Hz, 1H), 0.51 (d, J=7.9 Hz, 2H), 0.30 (d, J=4.9 Hz, 2H). LCMS (M+H)$^+$=402.2.

Example 45

8-Chloro-7-(4-(2-chlorophenyl)piperidin-1-yl)-3-(2,2,2-trifluoroethyl)-[1,2,4]triazolo[4,3-b]pyridazine

N'-(4-Chloro-5-(4-(2-chlorophenyl)piperidin-1-yl)pyridazin-3-yl)-3,3,3-trifluoropropanehydrazide 3,3,3-Trifluoropropanoyl chloride (0.042 ml, 0.407 mmol) was added to a solution of 4-chloro-5-(4-(2-chlorophenyl)piperidin-1-yl)-3-hydrazinylpyridazine (0.125 g, 0.370 mmol) in ethyl acetate (1.5 ml), THF (3 ml), and saturated sodium bicarbonate (3 ml) and was stirred at room temperature for 16 h. The mixture was diluted with ethyl acetate and water. The ethyl acetate layer was separated and concentrated to give N'-(4-chloro-5-(4-(2-chlorophenyl)piperidin-1-yl)pyridazin-3-yl)-3,3,3-trifluoropropanehydrazide. (M+H)$^+$=448.2.

8-Chloro-7-(4-(2-chlorophenyl)piperidin-1-yl)-3-(2,2,2-trifluoroethyl)-[1,2,4]triazolo[4,3-b]pyridazine A mixture of N'-(4-chloro-5-(4-(2-chlorophenyl)piperidin-1-yl)pyridazin-3-yl)-3,3,3-trifluoropropanehydrazide (0.125 g, 0.279 mmol) and phosphorus oxychloride (0.039 ml, 0.418 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-7-(4-(2-chlorophenyl)piperidin-1-yl)-3-(2,2,2-trifluoroethyl)-[1,2,4]triazolo[4,3-b]pyridazine as a brown oil (2.8 mg, 2.2%). $^1$H NMR (500 MHz, DMSO-d$_6$) δ 8.77 (s, 1H), 7.53-7.43 (m, 2H), 7.40-7.34 (m, 1H), 7.31-7.26 (m, 1H), 4.36 (q, J=10.7 Hz, 2H), 3.82 (d, J=12.5 Hz, 2H), 3.31-3.10 (m, 3H), 2.01-1.74 (m, 4H). LCMS (M+H)$^+$=430.2.

Example 46

8-Chloro-3-(cyclopropylmethyl)-7-(4-(2,3-dichlorophenyl)piperidin-1-yl)-[1,2,4]triazolo[4,3-b]pyridazine

4-Chloro-5-(4-(2,3-dichlorophenyl)piperidin-1-yl)-3-hydrazinylpyridazine

A mixture of 3,4,5-trichloropyridazine (0.25 g, 1.363 mmol), 4-(2,3-dichlorophenyl)piperidine, 4-methylbenzenesulfonate salt (0.547 g, 1.363 mmol), and potassium carbonate (0.396 g, 2.86 mmol) in dioxane (5 ml) was heated to reflux for 1 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 4-chloro-5-(4-(2,3-dichlorophenyl)piperidin-1-yl)-3-hydrazinylpyridazine as a brown oil. (M+H)$^+$=374.1.

N'-(4-Chloro-5-(4-(2,3-dichlorophenyl)piperidin-1-yl)pyridazin-3-yl)-2-cyclopropylacetohydrazide A solution of thionyl chloride (0.122 ml, 1.677 mmol) and 2-cyclopropylacetic acid (0.034 ml, 0.369 mmol) in methylene chloride (1.500 ml) was heated to reflux for 1 h and then concentrated. A solution of the residue in ethyl acetate (2.5 ml) was added to a solution of 4-chloro-5-(4-(2,3-dichlorophenyl)piperidin-1-yl)-3-hydrazinylpyridazine (0.125 g, 0.335 mmol) in ethyl acetate (1.5 ml), THF (3 ml), and saturated sodium bicarbonate (3 ml) and was stirred at room temperature for 16 h. The mixture was diluted with ethyl acetate and water. The ethyl acetate layer was separated and concentrated to give N'-(4-chloro-5-(4-(2,3-dichlorophenyl)piperidin-1-yl)pyridazin-3-yl)-2-cyclopropylacetohydrazide as a brown oil. (M+H]$^+$=456.1.

8-Chloro-3-(cyclopropylmethyl)-7-(4-(2,3-dichlorophenyl)piperidin-1-yl)-[1,2,4]triazolo[4,3-b]pyridazine A mixture of N'-(4-chloro-5-(4-(2,3-dichlorophenyl)piperidin-1-yl)pyridazin-3-yl)-2-cyclopropylacetohydrazide (0.125 g, 0.275 mmol) and phosphorus oxychloride (0.038 ml, 0.412 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(2,3-dichlorophenyl)piperidin-1-yl)-[1,2,4]triazolo[4,3-b]pyridazine as a brown oil (5 mg, 4.16%). $^1$H NMR (500 MHz, DMSO-d$_6$) δ 8.68 (s, 1H), 7.56 (dd, J=7.8, 1.4 Hz, 1H), 7.48 (dd, J=7.8, 1.4 Hz, 1H), 7.42-7.37 (m, 1H), 3.76

(d, J=12.5 Hz, 2H), 3.29-3.18 (m, 3H), 3.02 (d, J=7.0 Hz, 2H), 2.03-1.76 (m, 4H), 1.29-1.12 (m, 1H), 0.51 (dd, J=8.1, 1.7 Hz, 2H), 0.35-0.25 (m, 2H). LCMS (M+H)$^+$=438.

Example 47

8-Chloro-3-(cyclopropylmethyl)-7-(4-(3,5-dichlorophenyl)piperidin-1-yl)-[1,2,4]triazolo[4,3-b]pyridazine 4-Chloro-5-(4-(3,5-dichlorophenyl)piperidin-1-yl)-3-hydrazinylpyridazine A mixture of 3,4,5-trichloropyridazine (0.25 g, 1.363 mmol), 4-(3,5-dichlorophenyl)piperidine, 4-methylbenzenesulfonate salt (0.547 g, 1.363 mmol), and potassium carbonate (0.396 g, 2.86 mmol) in dioxane (5 ml) was heated to reflux for 1 h. The mixture was cooled and 35% hydrazine in water (2.469 ml, 27.3 mmol) was added. The mixture was heated to reflux for 16 h. The reaction was diluted with ethyl acetate and water. The ethyl acetate layer was washed with water, dried over magnesium sulfate, and concentrated to give 4-chloro-5-(4-(3,5-dichlorophenyl)piperidin-1-yl)-3-hydrazinylpyridazine as a brown oil. (M+H)$^+$=374.1.

N'-(4-Chloro-5-(4-(3,5-dichlorophenyl)piperidin-1-yl)pyridazin-3-yl)-2-cyclopropylacetohydrazide A solution of thionyl chloride (0.122 ml, 1.677 mmol) and 2-cyclopropylacetic acid (0.034 ml, 0.369 mmol) in methylene chloride (1.5 ml) was heated to reflux for 1 h and then concentrated. A solution of the residue in ethyl acetate (1.5 ml) was added to a solution of 4-chloro-5-(4-(3,5-dichlorophenyl)piperidin-1-yl)-3-hydrazinylpyridazine (0.125 g, 0.335 mmol) in ethyl acetate (1.5 ml), THF (3 ml), and saturated sodium bicarbonate (3 ml). The mixture was stirred at room temperature for 16 h. The mixture was diluted with ethyl acetate and water. The ethyl acetate layer was separated and concentrated to give N'-(4-chloro-5-(4-(3,5-dichlorophenyl)piperidin-1-yl)pyridazin-3-yl)-2-cyclopropylacetohydrazide as a brown oil. LCMS (M+H)$^+$=456.1.

8-Chloro-3-(cyclopropylmethyl)-7-(4-(3,5-dichlorophenyl)piperidin-1-yl)-[1,2,4]triazolo[4,3-b]pyridazine A mixture of N'-(4-chloro-5-(4-(3,5-dichlorophenyl)piperidin-1-yl)pyridazin-3-yl)-2-cyclopropylacetohydrazide (0.125 g, 0.275 mmol) and phosphorus oxychloride (0.038 ml, 0.412 mmol) in acetonitrile (5 ml) was heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-7-(4-(3,5-dichlorophenyl)piperidin-1-yl)-[1,2,4]triazolo[4,3-b]pyridazine as a brown oil (9.9 mg, 8.25%). $^1$H NMR (500 MHz, DMSO-d$_6$) δ 8.66 (s, 1H), 7.47 (t, J=2.0 Hz, 1H), 7.42 (d, J=2.1 Hz, 2H), 3.75 (d, J=12.5 Hz, 2H), 3.24-3.12 (m, 2H), 3.02 (d, J=6.7 Hz, 2H), 2.93-2.79 (m, 1H), 1.97- 1.72 (m, 4H), 1.30-1.16 (m, 1H), 0.51 (dd, J=8.1, 1.7 Hz, 2H), 0.30 (d, J=5.8 Hz, 2H). LCMS (M+H)$^+$=438.2.

Example 48

8-Chloro-7-(4-(3,5-dichlorophenyl)piperidin-1-yl)-3-(2,2,2-trifluoroethyl)-[1,2,4]triazolo[4,3-b]pyridazine N'-(4-Chloro-5-(4-(3,5-dichlorophenyl)piperidin-1-yl)pyridazin-3-yl)-3,3,3-trifluoropropanehydrazide 3,3,3-Trifluoropropanoyl chloride (0.038 ml, 0.369 mmol) was added to a solution of 4-chloro-5-(4-(3,5-dichlorophenyl)piperidin-1-yl)-3-hydrazinylpyridazine (0.125 g, 0.335 mmol) in ethyl acetate (1.5 ml), THF (3.0 ml), and saturated sodium bicarbonate (3 ml) and was stirred at room temperature for 16 h. The mixture was diluted with ethyl acetate and water. The ethyl acetate layer was separated and concentrated to give N'-(4-chloro-5-(4-(3,5-dichlorophenyl)piperidin-1-yl)pyridazin-3-yl)-3,3,3-trifluoropropanehydrazide as a brown oil. LCMS (M+H)$^+$=484.1.

8-Chloro-7-(4-(3,5-dichlorophenyl)piperidin-1-yl)-3-(2,2,2-trifluoroethyl)-[1,2,4]triazolo[4,3-b]pyridazine A mixture of N'-(4-chloro-5-(4-(3,5-dichlorophenyl)piperidin-1-yl)pyridazin-3-yl)-3,3,3-trifluoropropanehydrazide (0.125 g, 0.259 mmol) and phosphorus oxychloride (0.036 ml, 0.388 mmol) in acetonitrile (5 ml) was placed in a sealed microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-7-(4-(3,5-dichlorophenyl)piperidin-1-yl)-3-(2,2,2-trifluoroethyl)-[1,2,4]triazolo[4,3-b]pyridazine as a brown oil (4.3 mg, 3.4%). $^1$H NMR (500 MHz, DMSO-d$_6$) δ 8.76 (s, 1H), 7.48 (t, J=1.8 Hz, 1H), 7.42 (d, J=1.8 Hz, 2H), 4.36 (q, J=10.7 Hz, 2H), 3.81 (d, J=12.5 Hz, 2H), 3.26-3.13 (m, 2H), 2.92-2.80 (m, 1H), 1.99-1.75 (m, 4H). LCMS (M+H)$^+$=464.1.

Example 49

8-Chloro-3-(cyclopropylmethyl)-N-ethyl-N-((2-(4-fluorophenyl)cyclopropyl)methyl)-[1,2,4]triazolo[4,3-b]pyridazin-7-amine 5-Chloro-N-ethyl-N-((2-(4-fluorophenyl)cyclopropyl)methyl)-6-hydrazinylpyridazin-4-amine A mixture of 3,4,5-trichloropyridazine (0.250 g, 1.363 mmol), N-((2-(4-fluorophenyl)cyclopropyl)methyl)ethanamine HCl (0.313 g, 1.363 mmol), and potassium carbonate (0.396 g, 2.86 mmol) in dioxane (5 ml) was heated to reflux for 16 h. The mixture was cooled and 35% hydrazine in water (2.469 ml, 27.3 mmol) was added. The mixture was heated to reflux for 16 h overnight. The reaction was diluted with ethyl acetate and water. The ethyl acetate layer was washed with water, dried over magnesium sulfate, and concentrated to give 5-chloro-N-ethyl-N-((2-(4-fluorophenyl)cyclopropyl)methyl)-6-hydrazinylpyridazin-4-amine as a brown oil. (M+H)$^+$=336.2.

N'-(4-Chloro-5-(ethyl((2-(4-fluorophenyl)cyclopropyl)methyl)amino)pyridazin-3-yl)-2-cyclopropylacetohydrazide A solution of 5-chloro-N-ethyl-N-((2-(4-fluorophenyl)cyclopropyl)methyl)-6-hydrazinylpyridazin-4-amine (0.125 g, 0.372 mmol) and 2-cyclopropylacetyl chloride (0.049 g, 0.409 mmol) in ethyl acetate (1.5 ml), THF (3 ml), and saturated sodium bicarbonate) (3 ml) was stirred at room temperature for 16 h. The mixture was diluted with ethyl acetate and water. The ethyl acetate layer was separated and concentrated to give N'-(4-chloro-5-(ethyl((2-(4-fluorophenyl)cyclopropyl)methyl)amino)pyridazin-3-yl)-2-cyclopropylacetohydrazide as a brown oil.

8-Chloro-3-(cyclopropylmethyl)-N-ethyl-N-((2-(4-fluorophenyl)cyclopropyl)methyl)-[1,2,4]triazolo[4,3-b]pyridazin-7-amine A mixture of N'-(4-chloro-5-(ethyl((2-(4-fluorophenyl)cyclopropyl)methyl)amino)pyridazin-3-yl)-2-cyclopropylacetohydrazide (0.125 g, 0.299 mmol) and phosphorus oxychloride (0.042 ml, 0.449 mmol) in acetonitrile (5 ml) was placed in a sealed microwave vial and heated to 80° C. for 16 h. The reaction was cooled and quenched with saturated sodium carbonate. The mixture was diluted with ethyl acetate and water. The ethyl acetate layer was separated and concentrated to a brown oil that was purified by preparative HPLC to give 8-chloro-3-(cyclopropylmethyl)-N-ethyl-N-((2-(4-fluorophenyl)cyclopropyl)methyl)-[1,2,4]triazolo[4,3-b]pyridazin-7-amine as a brown oil (0.3 g, 0.25%). $^1$H NMR (400 MHz, METHANOL-$d_4$) δ 8.51 (s, 1H), 7.01-6.76 (m, 4H), 3.71-3.53 (m, 3H), 3.44-3.35 (m, 1H), 3.03 (d, J=7.0 Hz, 2H), 1.84-1.68 (m, 1H), 1.41-1.11 (m, 5H), 1.06-0.86 (m, 2H), 0.57 (dd, J=8.0, 1.5 Hz, 2H), 0.35 (d, J=5.8 Hz, 2H). LCMS (M+H)$^+$=400.1.

Example 50

8-Chloro-3-(cyclopropylmethyl)-7-(4-(2-(difluoromethoxy)-3,6-difluorophenyl)piperidin-1-yl)-[1,2,4]triazolo[4,3-b]pyridazine 2-Bromo-3-(difluoromethoxy)-1,4-difluorobenzene A mixture of 2-bromo-3,6-difluorophenol (2.5 g, 11.96 mmol), sodium 2-chloro-2,2-difluoroacetate (2.189 g, 14.35 mmol), and potassium carbonate (1.984 g, 14.35 mmol) in DMF (7 ml) was heated in a 100° C. oil bath for 2 h. The mixture was diluted with water and methylene chloride. The methylene chloride layer was separated, washed 3 times with water, dried over magnesium sulfate, and concentrated to give 2-bromo-3-(difluoromethoxy)-1,4-difluorobenzene as a clear oil (2.87 g, 93%). $^1$H NMR (400 MHz, CHLOROFORM-d) δ 7.17 (td, J=9.3, 4.8 Hz, 1H), 7.06 (ddd, J=9.3, 7.5, 4.3 Hz, 1H), 6.64 (td, J=73.0, 1.5 Hz, 1H).

tert-Butyl 4-(2-(difluoromethoxy)-3,6-difluorophenyl)-5,6-dihydropyridine-1(2H)-carboxylate A mixture of tert-butyl 4-(4,4,5,5-tetramethyl-1,3,2-dioxaborolan-2-yl)-5,6-dihydropyridine-1(2H)-carboxylate (0.800 g, 2.59 mmol), 2-bromo-3-(difluoromethoxy)-1,4-difluorobenzene (0.838 g, 3.24 mmol), potassium carbonate (0.805 g, 5.82 mmol), and tetrakis (trlphenylphosphine) palladium (0) (0.08 g, 0.069 mmol) in dioxane (12 ml) and water (3 ml) was heated in a 100° C. oil bath for 2 h. The tan solution was cooled and diluted with ethyl acetate and water. The ethyl acetate layer was washed with water and sodium carbonate, dried with brine, and concentrated. The oil was dissolved in 50% methylene chloride/hexane and applied to a silica gel column. The product was eluted with 50-100% methylene chloride/hexane. The product fractions were concentrated to give tert-butyl 4-(2-(difluoromethoxy)-3,6-difluorophenyl)-5,6-dihydropyridine-1(2H)-carboxylate as a clear oil (0.65 g, 69.5%). $^1$H NMR (400 MHz, CHLOROFORM-d) δ 7.07 (td, J=9.4, 4.8 Hz, 1H), 6.96 (td, J=8.8, 4.1 Hz, 1H), 6.47 (td, J=73.8, 0.8 Hz, 1H), 5.86-5.68 (m, 1H), 4.08 (d, J=2.5 Hz, 2H), 3.63 (t, J=5.5 Hz, 2H), 2.38 (br. s., 2H), 1.51 (s, 9H).

tert-Butyl 4-(2-(difluoromethoxy)-3,6-difluorophenyl)piperidine-1-carboxylate

A mixture of tert-butyl 4-(2-(difluoromethoxy)-3,6-difluorophenyl)-5,6-dihydropyridine-1(2H)-carboxylate (0.65 g, 1.799 mmol) and PtO2 (0.1 g, 0.44 mmol) in methanol (20 ml) was shaken under 50 psi of hydrogen in a Parr bottle for 2 h. The mixture was filtered through celite and the filtrate was concentrated to give tert-butyl 4-(2-(difluoromethoxy)-3,6-difluorophenyl)piperidine-1-carboxylate (0.62 g, 85%) as colorless gum. $^1$H NMR (400 MHz, CHLOROFORM-d) δ 6.99 (td, J=9.4, 4.8 Hz, 1H), 6.88 (td, J=9.7, 4.1 Hz, 1H), 6.56 (t, J=75.0 Hz, 1H), 4.22 (br. s., 2H), 3.31-3.14 (m, 1H), 2.76 (br. s., 2H), 2.10-1.94 (m, 2H), 1.61 (d, J=11.8 Hz, 2H), 1.47 (s, 9H). LCMS: M+1=264 (—BOC).

4-Chloro-5-(4-(2-(difluoromethoxy)-3,6-difluorophenyl)piperidin-1-yl)-3-hydrazinylpyridazine A mixture of 4-(2-(difluoromethoxy)-3,6-difluorophenyl)piperidine (0.57 g, 2.165 mmol), 20% aqueous potassium carbonate (2.72 ml, 4.33 mmol) and 3,4,5-trichloropyridazine (0.397 g, 2.165 mmol) in dioxane (10 ml) was stirred at 90° C. for 2 h. Hydrazine hydrate (0.799 g, 15.96 mmol) was added and the reaction mixture was stirred at 90° C. for 16 h. The mixture was concentrated and the residue was diluted with ethyl acetate and saturated aqueous sodium bicarbonate. The aqueous layer was extracted with ethyl acetate (4×10 ml). The combined organic layers were washed with additional saturated aqueous sodium bicarbonate, and was used for next step. An aliquot was purified by Prep. HPLC on a Phenomenex-Luna 30×100 mm S10 Axia column, using 20-80% methanol/water containing 0.1% TFA to give 4-chloro-5-(4-(2-(difluoromethoxy)-3,5-difluorophenyl)piperidin-1-yl)-3-hydrazinylpyridazine for characterization. $^1$H NMR (400 MHz, METHANOL-$d_4$) δ 8.39 (s, 1H), 7.23-7.14 (m, 1H), 7.12-7.05 (m, 1H), 6.86 (t, J=74.0 Hz, 1H), 3.89-3.79 (m, 2H), 3.44-3.34 (m, 1H), 3.05 (t, J=12.4 Hz, 2H), 2.42-2.24 (m, 2H), 1.87-1.73 (m, 2H). LCMS: M+1=405.9.

N'-(4-Chloro-5-(4-(2-(difluoromethoxy)-3,6-difluorophenyl)piperidin-1-yl)pyridazin-3-yl)-2-cyclopropylacetohydrazide A mixture of 4-chloro-5-(4-(2-(difluoromethoxy)-3,6-difluorophenyl)piperidin-1-yl)-3-hydrazinylpyridazine (0.25 g, 0.616 mmol), saturated sodium carbonate (15 ml), and THF (25 ml) was stirred as 2-cyclopropylacetyl chloride (0.365 ml, 0.616 mmol) was added. The mixture was stirred at for 20 min. The reaction mixture was diluted with ethyl acetate and aqueous sodium bicarbonate. The aqueous layer was extracted with ethyl acetate (3×20 ml). The combined organic layers were washed with aqueous sodium bicarbonate (2×20 ml) and brine (20 ml), dried over magnesium sulfate, and concentrated. The residue was purified by silica gel chromatography, using 0-100% ethyl acetate/hexane as the eluent to give N'-(4-chloro-5-(4-(2-(difluoromethoxy)-3,6-difluorophenyl)piperidin-1-yl)pyridazin-3-yl)-2-cyclopropylacetohydrazide (0.1 g, 30.6% for 2 steps) as a brown solid. $^1$H NMR (400 MHz, METHANOL-d$_4$) δ 8.46 (s, 1H), 7.19 (td, J=9.5, 4.8 Hz, 1H), 7.12-7.05 (m, 1H), 6.86 (t, J=75.0 Hz, 1H), 3.87 (d, J=12.5 Hz, 2H), 3.46-3.34 (m, 1H), 3.15-2.99 (m, 2H), 2.32 (dd, J=12.9, 10.9 Hz, 2H), 2.27 (d, J=7.0 Hz, 2H), 1.88-1.77 (m, 2H), 1.17-1.04 (m, 1H), 0.61-0.52 (m, 2H), 0.31-0.23 (m, 2H). LCMS: M+1=487.9.

8-Chloro-3-(cyclopropylmethyl)-7-(4-(2-(difluoromethoxy)-3,6-difluorophenyl)piperidin-1-yl)-[1,2,4]triazolo[4,3-b]pyridazine A solution of N'-(4-chloro-5-(4-(2-(difluoromethoxy)-3,6-difluorophenyl)piperidin-1-yl)pyridazin-3-yl)-2-cyclopropylacetohydrazide (100 mg, 0.205 mmol) and triphenylphosphine (81 mg, 0.307 mmol) in methylene chloride (9 ml) and THF (3 ml) was stirred as azidotrimethylsilane (0.035 ml, 0.266 mmol) was added, followed by the dropwise addition of 40% DEAD in toluene (0.140 ml, 0.307 mmol). The resulting mixture was stirred at for 10 min. The reaction mixture was diluted with ethyl acetate and saturated sodium bicarbonate. The aqueous layer was extracted with ethyl acetate (3×5 ml). The combined organic layers were washed with saturated aqueous sodium bicarbonate (10 ml) and were then concentrated under vacuum. The residue was purified by preparative HPLC on a Phenomenex-Gemini 30×100 mm S10 column, using 20-80% acetonitrile/water containing 10 mM ammonium acetate as the elutent. The product fractions were concentrated. The residue was dissolved in ethyl acetate and saturated sodium bicarbonate. The aqueous layer was extracted with ethyl acetate (3×10 ml). The combined organic layers were washed with aqueous sodium bicarbonate (20 ml) and brine (20 ml), dried over magnesium sulfate, and concentrated. The material was further purified by silica gel chromatography using 2.0 M ammonia in methanol/ethyl acetate as the eluent to give 8-chloro-3-(cyclopropylmethyl)-7-(4-(2-(difluoromethoxy)-3,6-difluorophenyl)piperidin-1-yl)-[1,2,4]triazolo[4,3-b]pyridazine (46 mg, 45.9%) as a white solid. $^1$H NMR (400 MHz, METHANOL-d$_4$) δ 8.45 (s, 1H), 7.12 (td, J=9.5, 4.8 Hz, 1H), 7.05-6.95 (m, 1H), 6.73 (t, J=75.0 Hz, 1H), 3.85 (d, J=12.3 Hz, 2H), 3.42-3.33 (m, 1H), 3.23 (t, J=12.3 Hz, 2H), 3.05 (d, J=7.0 Hz, 2H), 2.44-2.26 (m, 2H), 1.92-1.77 (m, 2H), 1.34-1.19 (m, 1H), 0.59-0.51 (m, 2H), 0.38-0.30 (m, 2H). LCMS: M+1=469.9.

Example 51

8-Chloro-7-(4-(2-(difluoromethoxy)-3,6-difluorophenyl)piperidin-1-yl)-3-(2,2,2-trifluoroethyl)-[1,2,4]triazolo[4,3-b]pyridazine N'-(4-Chloro-5-(4-(2-(difluoromethoxy)-3,6-difluorophenyl)piperidin-1-yl)pyridazin-3-yl)-3,3,3-trifluoropropanehydrazide A mixture of 4-chloro-5-(4-(2-(difluoromethoxy)-3,6-difluorophenyl)piperidin-1-yl)-3-hydrazinylpyridazine (0.25 g, 0.616 mmol), saturated sodium carbonate (15 ml), and THF (25 ml) was stirred as 3,3,3-trifluoropropanoyl chloride (0.090 g, 0.616 mmol) was added. The mixture was stirred at for 20 min. The reaction mixture was diluted with ethyl acetate and aqueous sodium bicarbonate. The aqueous layer was extracted with ethyl acetate (3×20 ml). The combined organic layers were washed with aqueous sodium bicarbonate (2×20 ml) and brine (20 ml), dried over magnesium sulfate, and concentrated. The residue was purified by silica gel chromatography, using 0-100% ethyl acetate/hexane as the eluent to give N'-(4-chloro-5-(4-(2-(difluoromethoxy)-3,6-difluorophenyl)piperidin-1-yl)pyridazin-3-yl)-3,3,3-trifluoropropanehydrazide (0.08 g, 24.2% for 2 steps) as a brown solid. $^1$H NMR (400 MHz, METHANOL-d$_4$) δ 8.47 (s, 1H), 7.19 (td, J=9.5, 4.9 Hz, 1H), 7.11-7.05 (m, 1H), 6.86 (t, J=75.0 Hz, 1H), 3.87 (d, J=12.5 Hz, 2H), 3.43-3.38 (m, 1H), 3.35 (q, J=10.5 Hz, 2H), 3.07 (t, J=12.4 Hz, 2H), 2.42-2.25 (m, 2H), 1.88-1.75 (m, 2H). LCMS: M+1=515.9.

8-Chloro-7-(4-(2-(difluoromethoxy)-3,6-difluorophenyl)piperidin-1-yl)-3-(2,2,2-trifluoroethyl)-[1,2,4]triazolo[4,3-b]pyridazine A mixture of N'-(4-chloro-5-(4-(2-(difluoromethoxy)-3,6-difluorophenyl)piperidin-1-yl)pyridazin-3-yl)-3,3,3-trifluoropropanehydrazide (80 mg, 0.155 mmol) and Burgess' reagent (73.9 mg, 0.310 mmol) in THF (5 ml) was stirred in a microwave vial at 90° C. for 18 h. The reaction mixture was purified by preparative HPLC on a Phenomenex-Gemini 30×100 mm S10 column, using 20-80% acetonitrile/water, 10 mmol in ammonium acetate to give 8-chloro-7-(4-(2-(difluoromethoxy)-3,6-difluorophenyl)piperidin-1-yl)-3-(2,2,2-trifluoroethyl)-[1,2,4]triazolo[4,3-b]pyridazine (33 mg, 39.8%) as a white solid. $^1$H NMR (400 MHz, CHLOROFORM-d) δ 8.30 (s, 1H), 7.07 (td, J=9.3, 4.8 Hz, 1H), 6.97 (td, J=9.7, 4.3 Hz, 1H), 6.63 (t, J=75.0 Hz, 1H), 4.09 (q, J=9.8 Hz, 2H), 3.87-3.75 (m, 2H), 3.36 (tt, J=12.4, 3.3 Hz, 1H), 3.23 (t, J=12.2 Hz, 2H), 2.47-2.29 (m, 2H), 1.93-1.78 (m, 2H). LCMS: M+1=497.9.

Example 52

8-Chloro-3-(cyclopropylmethyl)-7-(4-(2-(difluoromethoxy)-4,5-difluorophenyl)piperidin-1-yl)-[1,2,4]triazolo[4,3-b]pyridazine 1-Bromo-2-(difluoromethoxy)-4,5-difluorobenzene A mixture of 2-bromo-4,5-difluorophenol (2.5 g, 11.96 mmol), sodium 2-chloro-2,2-difluoroacetate (2.189 g, 14.35 mmol), and potassium carbonate (1.984 g, 14.35 mmol) in DMF (7 ml) was heated in a 100° C. oil bath for 2 h. The mixture was diluted with water and methylene chloride. The methylene chloride layer was separated, washed 3 times with water, dried over magnesium sulfate, and concentrated to give 1-bromo-2-(difluoromethoxy)-4,5-difluorobenzene as a brown solid (1.90 g, 61%). $^1$H NMR (400 MHz, CHLOROFORM-d) δ 7.52-7.45 (m, 1H), 7.17 (dd, J=10.4, 7.2 Hz, 1H), 6.48 (t, J=72.8 Hz, 1H).

tert-Butyl 4-(2-(difluoromethoxy)-4,5-difluorophenyl)-5,6-dihydropyridine-1(2H)-carboxylate A mixture of tert-butyl 4-(4,4,5,5-tetramethyl-1,3,2-dioxaborolan-2-yl)-5,6-dihydropyridine-1(2H)-carboxylate (0.8 g, 2.59 mmol), 1-bromo-2-(difluoromethoxy)-4,5-difluorobenzene (0.838 g, 3.23 mmol), potassium carbonate (0.805 g, 5.82 mmol), and tetrakis (trlphenylphosphine) palladium (0) (0.08 g, 0.069 mmol) in dioxane (12 ml) and water (3 ml) was heated in a 100° C. oil bath for 2 h. The tan solution was cooled and diluted with ethyl acetate and water. The ethyl acetate layer was washed with water and sodium carbonate, dried with brine, and concentrated. The oil was dissolved in 50% methylene chloride/hexane and applied to a silica gel column. The product was eluted with 50-100% methylene chloride/hexane. The product fractions were concentrated to give tert-butyl 4-(2-(difluoromethoxy)-4,5-difluorophenyl)-5,6-dihydropyridine-1(2H)-carboxylate as a clear oil (0.53 g, 56.7%). $^1$H NMR (400 MHz, CHLOROFORM-d) δ 7.64-7.61 (m, 1H), 7.12-6.97 (m, J=10.7, 8.7 Hz, 2H), 6.39 (t, J=73.5 Hz, 1H), 5.89-5.72 (m, 1H), 4.05 (d, J=2.5 Hz, 2H), 3.59 (t, J=5.5 Hz, 2H), 2.43 (br. s., 2H), 1.50 (s, 9H).

tert-Butyl 4-(2-(difluoromethoxy)-4,5-difluorophenyl)piperidine-1-carboxylate

A mixture of tert-butyl 4-(2-(difluoromethoxy)-4,5-difluorophenyl)-5,6-dihydropyridine-1(2H)-carboxylate (0.53 g, 1.467 mmol) and PtO2 (0.1 g, 0.44 mmol) in methanol (20 ml) was shaken under 50 psi of hydrogen in a Parr bottle for 2 h. The mixture was filtered through celite and the filtrate was concentrated to give tert-butyl 4-(2-(difluoromethoxy)-4,5-difluorophenyl)piperidine-1-carboxylate (0.43 g, 72.6%) as light-brown gum. $^1$H NMR (400 MHz, CHLOROFORM-d) δ 7.03 (dd, J=11.0, 8.5 Hz, 1H), 6.99 (dd, J=11.0, 6.8 Hz, 1H), 6.48 (t, J=72.0 Hz, 1H), 4.23 (br. s., 2H), 3.12-2.94 (m, 1H), 2.79 (t, J=12.0 Hz, 2H), 1.74 (d, J=13.1 Hz, 2H), 1.57-1.49 (m, J=4.3 Hz, 2H), 1.47 (s, 9H). LCMS: M+1=264(—BOC).

4-Chloro-5-(4-(2-(difluoromethoxy)-4,5-difluorophenyl)piperidin-1-yl)-3-hydrazinylpyridazine A mixture of 4-(2-(difluoromethoxy)-4,5-difluorophenyl)piperidine (0.42 g, 1.596 mmol), 20% aqueous potassium carbonate (2.005 ml, 3.19 mmol) in dioxane (10 ml) and 3,4,5-trichloropyridazine (0.293 g, 1.596 mmol) was stirred at 90° C. for 2 h. Hydrazine hydrate (0.799 g, 15.96 mmol) was added and the reaction mixture was stirred at 90° C. for 16 h. The mixture was concentrated and the residue was diluted with ethyl acetate and saturated aqueous sodium bicarbonate. The aqueous layer was extracted with ethyl acetate (4×10 ml). The combined organic layers were washed with additional saturated aqueous sodium bicarbonate, and was used for next step. An aliquot was purified by Prep. HPLC on a Phenomenex-Luna 30×100 mm S10 Axia column, using 20-80% methanol/water containing 0.1% TFA to give 4-chloro-5-(4-(2-(difluoromethoxy)-4,5-difluorophenyl)piperidin-1-yl)-3-hydrazinylpyridazine for characterization. $^1$H NMR (400 MHz, METHANOL-d$_4$) δ 8.39 (s, 1H), 7.40-7.30 (m, 1H), 7.18 (dd, J=11.2, 6.9 Hz, 1H), 6.97-6.79 (m, 1H), 3.84 (d, J=12.3 Hz, 2H), 3.24-3.15 (m, 1H), 3.14-3.02 (m, 2H), 1.97-1.81 (m, 4H). LCMS: M+1=405.9.

N'-(4-Chloro-5-(4-(2-(difluoromethoxy)-4,5-difluorophenyl)piperidin-1-yl)pyridazin-3-yl)-2-cyclopropylacetohydrazide A mixture of 4-chloro-5-(4-(2-(difluoromethoxy)-4,5-difluorophenyl)piperidin-1-yl)-3-hydrazinylpyridazine (0.25 g, 0.616 mmol) in ethyl acetate (50 ml), THF (25 ml), and saturated aqueous sodium carbonate (15 ml) was added 2-cyclopropylacetyl chloride (0.365 mL, 0.616 mmol), The mixture was stirred at for 20 min. The mixture was diluted with ethyl acetate and aqueous sodium bicarbonate. The aqueous layer was extracted with ethyl acetate (3×20 ml). The combined organic layers were washed with aqueous sodium bicarbonate (2×20 ml) and brine (20 ml), dried over magnesium sulfate, and concentrated. The residue was purified by silica gel chromatography, using 0-100% ethyl acetate/hexane as the eluent to give N'-(4-chloro-5-(4-(2-(difluoromethoxy)-4,5-difluorophenyl)piperidin-1-yl)pyridazin-3-yl)-2-cyclopropylacetohydrazide (0.06 g, 18.2% for 2 steps) as a white solid. $^1$H NMR (400 MHz, METHANOL-d$_4$) δ 8.46 (s, 1H), 7.35 (dd, J=11.7, 8.9 Hz, 1H), 7.18 (dd, J=11.3, 7.0 Hz, 1H), 6.88 (t, J=75.0 Hz, 1H), 3.86 (d, J=12.3 Hz, 2H), 3.25-3.15 (m, 1H), 3.14-3.04 (m, 2H), 2.26 (d, J=7.0 Hz, 2H), 1.97-1.80 (m, 4H), 1.18-1.04 (m, 1H), 0.61-0.52 (m, 2H), 0.31-0.24 (m, 2H). LCMS: M+1=487.9.

8-Chloro-3-(cyclopropylmethyl)-7-(4-(2-(difluoromethoxy)-4,5-difluorophenyl)piperidin-1-yl)-[1,2,4]triazolo[4,3-b]pyridazine A solution of N'-(4-chloro-5-(4-(2-(difluoromethoxy)-4,5-difluorophenyl)piperidin-1-yl)pyridazin-3-yl)-2-cyclopropylacetohydrazide (60 mg, 0.123 mmol) and triphenylphosphine (48.4 mg, 0.184 mmol) in methylene chloride (4 ml) and THF (2 ml) was stirred at room temperature as azidotrimethylsilane (0.021 ml, 0.160 mmol) was added, followed by dropwise addition of 40% DEAD in toluene (0.084 ml, 0.184 mmol). The resulting mixture was stirred at for 10 min. The reaction mixture was diluted with ethyl acetate and saturated sodium bicarbonate. The aqueous layer was extracted with ethyl acetate (3×5 ml). The combined organic layers were washed with saturated aqueous sodium bicarbonate (10 ml) and were then concentrated under vacuum. The residue was purified by preparative HPLC on a Phenomenex-Gemini 30×100 mm S10 column, using 20-80% acetonitrile/water containing 10 mM ammonium acetate as the elutent. The product fractions were concentrated. The residue was dissolved in ethyl acetate and saturated sodium bicarbonate. The aqueous layer was extracted with ethyl acetate (3×10 ml). The combined organic layers were washed with aqueous sodium bicarbonate (20 ml) and brine (20 ml), dried over magnesium sulfate, and concentrated under vacuum to give 8-chloro-3-(cyclopropylmethyl)-7-(4-(2-(difluoromethoxy)-4,5-difluorophenyl)piperidin-1-yl)-[1,2,4]triazolo[4,3-b]pyridazine (31 mg, 51%) as a white solid. $^1$H NMR (400 MHz, CHLOROFORM-d) δ 8.21 (s, 1H), 7.17 (dd, J=11.2, 8.7 Hz, 1H), 7.04 (dd, J=10.7, 6.9 Hz, 1H), 6.53 (t, J=75.0 Hz, 1H), 3.80-3.68 (m, 2H), 3.20 (td, J=11.9, 2.5 Hz, 2H), 3.13 (t, J=3.6 Hz, 1H), 3.10 (d, J=7.0 Hz, 2H), 2.01-1.94 (m, 2H), 1.94-1.81 (m, 2H), 1.37-1.23 (m, 1H), 0.59-0.51 (m, 2H), 0.39-0.31 (m, 2H). LCMS: (M+H)$^+$=469.9.

Example 53

8-Chloro-7-(4-(2-(difluoromethoxy)-4,5-difluorophenyl)piperidin-1-yl)-3-(2,2,2-trifluoroethyl)-[1,2,4]triazolo[4,3-b]pyridazine N'-(4-Chloro-5-(4-(2-(difluoromethoxy)-4,5-difluorophenyl)piperidin-1-yl)pyridazin-3-yl)-3,3,3-trifluoropropanehydrazide A mixture of 4-chloro-5-(4-(2-(difluoromethoxy)-4,5-difluorophenyl)piperidin-1-yl)-3-hydrazinylpyridazine (0.25 g, 0.616 mmol) in ethyl acetate (50 ml), THF (25 ml), and saturated aqueous sodium carbonate (15 ml) was added 3,3,3-trifluoropropanoyl chloride (0.090 g, 0.616 mmol). The mixture was stirred at for 20 min. The mixture was diluted with ethyl acetate and aqueous sodium bicarbonate. The aqueous layer was extracted with ethyl acetate (3×20 ml). The combined organic layers were washed with aqueous sodium bicarbonate (2×20 ml) and brine (20 ml), dried over magnesium sulfate, and concentrated. The residue was purified by silica gel chromatography, using 0-100% ethyl acetate/hexane as the eluent to give N'-(4-chloro-5-(4-(2-(difluoromethoxy)-4,5-difluorophenyl)piperidin-1-yl)pyridazin-3-yl)-3,3,3-trifluoropropanehydrazide (0.07 g, 20.7% for 2 steps). $^1$H NMR (400 MHz, METHANOL-d$_4$) δ 8.47 (s, 1H), 7.34 (dd, J=11.7, 8.9 Hz, 1H), 7.18 (dd, J=11.0, 7.0 Hz, 1H), 6.88 (t, J=75.0 Hz, 1H), 3.87 (d, J=12.5 Hz, 2H), 3.35 (q, J=10.5 Hz, 2H), 3.19 (dd, J=10.8, 4.8 Hz, 1H), 3.15-3.01 (m, 2H), 1.96-1.79 (m, 4H). LCMS: M+1=515.9.

8-Chloro-7-(4-(2-(difluoromethoxy)-4,5-difluorophenyl)piperidin-1-yl)-3-(2,2,2-trifluoroethyl)-[1,2,4]triazolo[4,3-b]pyridazine A mixture of N'-(4-Chloro-5-(4-(2-(difluoromethoxy)-4,5-difluorophenyl)piperidin-1-yl)pyridazin-3-yl)-3,3,3-trifluoropropanehydrazide (70 mg, 0.136 mmol) and Burgess' reagent (73.9 mg, 0.310 mmol) in THF (5 mL) was stirred in a microwave vial at 90° C. for 18 h. The reaction mixture was purified by preparative HPLC on a Phenomenex-Gemini 30×100 mm S10 column, using 20-80% water/acetonitrile containing 10 mM ammonium acetate as the eluent to give 8-chloro-7-(4-(2-(difluoromethoxy)-4,5-difluorophenyl)piperidin-1-yl)-3-(2,2,2-trifluoroethyl)-[1,2,4]triazolo[4,3-b]pyridazine (23 mg, 0.044 mmol, 34% yield). $^1$H NMR (400 MHz, CHLOROFORM-d) δ 8.29 (s, 1H), 7.17 (dd, J=11.2, 8.7 Hz, 1H), 7.04 (dd, J=10.5, 7.0 Hz, 1H), 6.53 (t, J=75.0 Hz, 1H), 4.09 (q, J=9.6 Hz, 2H), 3.83-3.73 (m, 2H), 3.23 (td, J=12.0, 2.5 Hz, 2H), 3.19-3.07 (m, 1H), 2.03-1.95 (m, 2H), 1.95-1.79 (m, 2H). LCMS: M+1=497.9.

Example 54

8-Chloro-3-(cyclopropylmethyl)-7-(4-(2-(difluoromethoxy)-3,5-difluorophenyl)piperidin-1-yl)-[1,2,4]triazolo[4,3-b]pyridazine

1-Bromo-2-(difluoromethoxy)-3,5-difluorobenzene

A mixture of 2-bromo-4,6-difluorophenol (5 g, 23.92 mmol), sodium 2-chloro-2,2-difluoroacetate (4.38 g, 28.7 mmol). and potassium carbonate (3.97 g, 28.7 mmol) in DMF (20 ml) was heated in a 100° C. oil bath for 2 h. The mixture was diluted with water and methylene chloride. The methylene chloride layer was separated, washed 3 times with water, dried over magnesium sulfate, and concentrated to give 1-bromo-2-(difluoromethoxy)-3,5-difluorobenzene as a clear oil (5.44 g, 44%). $^1$H NMR (400 MHz, CHLOROFORM-d) δ 7.25-7.15 (m, 1H), 6.95 (ddd, J=9.8, 8.0, 3.0 Hz, 1H), 6.79-6.33 (m, 1H).

tert-Butyl 4-(2-(difluoromethoxy)-3,5-difluorophenyl)-5,6-dihydropyridine-1(2H)-carboxylate A mixture of tert-butyl 4-(4,4,5,5-tetramethyl-1,3,2-dioxaborolan-2-yl)-5,6-dihydropyridine-1(2H)-carboxylate (0.8 g, 2.59 mmol), 1-bromo-2-(difluoromethoxy)-3,5-difluorobenzene (0.838 g, 3.23 mmol), potassium carbonate (0.805 g, 5.82 mmol), and tetrakis (trlphenylphosphine) palladium (0) (0.08 g, 0.069 mmol) in dioxane (12 ml) and water (3 ml) was heated in a 100° C. oil bath for 2 h. The tan solution was cooled and diluted with ethyl acetate and water. The ethyl acetate layer was washed with water and sodium carbonate, dried with brine, and concentrated. The oil was dissolved in 50% methylene chloride/hexane and applied to a silica gel column. The product was eluted with 50-100% methylene chloride/hexane. The product fractions were concentrated to give tert-butyl 4-(2-(difluoromethoxy)-3,5-difluorophenyl)-5,6-dihydropyridine-1(2H)-carboxylate as a clear oil (0.53 g, 57%). $^1$H NMR (400 MHz, CHLOROFORM-d) δ 6.85 (ddd, J=10.3, 8.0, 3.0 Hz, 1H), 6.77 (ddd, J=8.8, 3.0, 2.0 Hz, 1H), 6.43 (td, J=74.5, 0.8 Hz, 1H), 5.92-5.83 (m, 1H), 4.07 (d, J=2.5 Hz, 2H), 3.61 (t, J=5.5 Hz, 2H), 2.46 (d, J=1.5 Hz, 2H), 1.51 (s, 9H).

tert-Butyl 4-(2-(difluoromethoxy)-3,5-difluorophenyl)piperidine-1-carboxylate A mixture of tert-butyl 4-(2-(difluoromethoxy)-3,5-difluorophenyl)-5,6-dihydropyridine-1(2H)-carboxylate (0.53 g, 1.467 mmol) and PtO2 (0.1 g, 0.44 mmol) in methanol (20 ml) was shaken under 50 psi of hydrogen in a Parr bottle for 2 h. The mixture was filtered through celite and the filtrate was concentrated to give tert-butyl 4-(2-(difluoromethoxy)-3,5-difluorophenyl)piperidine-1-carboxylate (0.45 g, 76%) as colorless gum. $^1$H NMR (400 MHz, CHLOROFORM-d) δ 6.81-6.72 (m, 2H), 6.52 (t, J=76.0 Hz, 1H), 4.23 (br. s., 2H), 3.15 (t, J=12.2 Hz, 1H), 2.80 (t, J=12.0 Hz, 2H), 1.74 (d, J=12.8 Hz, 2H), 1.52 (d, J=4.0 Hz, 2H), 1.49-1.43 (m, 9H). LCMS: M+1=264 (—BOC).

4-Chloro-5-(4-(2-(difluoromethoxy)-3,5-difluorophenyl)piperidin-1-yl)-3-hydrazinylpyridazine A mixture of 4-(2-(difluoromethoxy)-3,5-difluorophenyl)piperidine (0.44 g, 1.672 mmol), 20% aqueous POTASSIUM CARBONATE (2.100 ml, 3.34 mmol) in dioxane (10 ml) and 3,4,5-trichloropyridazine (0.307 g, 1.672 mmol) was stirred at 90° C. for 2 h. Hydrazine hydrate (0.799 g, 15.96 mmol) was added and the reaction mixture was stirred at 90° C. for 16 h. The mixture was concentrated and the residue was diluted with ethyl acetate and saturated aqueous sodium bicarbonate. The aqueous layer was extracted with ethyl acetate (4×10 ml). The combined organic layers were washed with additional saturated aqueous sodium bicarbonate, and was used for next step. An aliquot was purified by Prep. HPLC on a Phenomenex-Luna 30×100 mm S10 Axia column, using 20-80% methanol/water containing 0.1% TFA to give 4-chloro-5-(4-(2-(difluoromethoxy)-3,5-difluorophenyl)piperidin-1-yl)-3-hydrazinylpyridazine for characterization. $^1$H NMR (400 MHz, METHANOL-d$_4$) δ 8.40 (s, 1H), 7.08-7.00 (m, 2H), 6.81 (t, J=75.0 Hz, 1H), 3.91-3.77 (m, 2H), 3.30-3.22 (m, J=5.5 Hz, 1H), 3.18-3.02 (m, 2H), 1.98-1.81 (m, 4H). LCMS: M+1=405.9.

N'-(4-Chloro-5-(4-(2-(difluoromethoxy)-3,5-difluorophenyl)piperidin-1-yl)pyridazin-3-yl)-2-cyclopropylacetohydrazide A mixture of 4-chloro-5-(4-(2-(difluoromethoxy)-3,5-difluorophenyl)piperidin-1-yl)-3-hydrazinylpyridazine (0.25 g, 0.616 mmol), ethyl acetate (50 ml), THF (25 ml), and saturated sodium carbonate (15 ml) was stirred as 2-cyclopropylacetyl chloride (0.365 mL, 0.616 mmol) was added. The mixture was stirred for 20 min. The mixture was diluted with ethyl acetate and saturated sodium bicarbonate. The aqueous layer was extracted with ethyl acetate (3×20 ml). The combined organic layers were washed with saturated sodium bicarbonate (2×20 ml) and brine (20 ml), dried over magnesium sulfate, and concentrated. The residue was purified by silica gel chromatography using 0-100% ethyl acetate/hexane as the eluent to give N'-(4-chloro-5-(4-(2-

(difluoromethoxy)-3,5-difluorophenyl)piperidin-1-yl) pyridazin-3-yl)-2-cyclopropylacetohydrazide (0.1 g, 31.9%) as a brown solid. $^1$H NMR (400 MHz, METHANOL-d$_4$) δ 8.47 (s, 1H), 7.09-7.00 (m, 2H), 6.81 (t, J=74.0 Hz, 1H), 3.87 (d, J=12.3 Hz, 2H), 3.31-3.24 (m, 1H), 3.18-3.03 (m, 2H), 2.27 (d, J=7.0 Hz, 2H), 1.97-1.82 (m, 4H), 1.18-1.05 (m, 1H), 0.63-0.53 (m, 2H), 0.32-0.23 (m, 2H). LCMS: M+1=487.9.

8-Chloro-3-(cyclopropylmethyl)-7-(4-(2-(difluoromethoxy)-3,5-difluorophenyl)piperidin-1-yl)-[1,2,4]triazolo[4,3-b]pyridazine A solution of N'-(4-chloro-5-(4-(2-(difluoromethoxy)-3,5-difluorophenyl)piperidin-1-yl)pyridazin-3-yl)-2-cyclopropylacetohydrazide (100 mg, 0.205 mmol), and triphenylphosphine (80.7 mg, 0.306 mmol) in methylene chloride (4 ml) and THF (2 ml) was stirred at room temperature as azidotrimethylsilane (0.035 ml, 0.267 mmol), followed by dropwise addition of 40% DEAD in toluene (0.140 ml, 0.306 mmol). The resulting mixture was stirred at for 10 min. The reaction mixture was diluted with ethyl acetate and saturated sodium bicarbonate. The aqueous layer was extracted with ethyl acetate (3×5 ml). The combined organic layers were washed with saturated aqueous sodium bicarbonate (10 ml) and were then concentrated under vacuum. The residue was purified by preparative HPLC on a Phenomenex-Gemini 30×100 mm S10 column, using 20-80% acetonitrile/water containing 10 mM ammonium acetate as the elutent. The product fractions were concentrated. The residue was dissolved in ethyl acetate and saturated sodium bicarbonate. The aqueous layer was extracted with ethyl acetate (3×10 ml). The combined organic layers were washed with aqueous sodium bicarbonate (20 ml) and brine (20 ml), dried over magnesium sulfate, and concentrated under vacuum to give 8-chloro-3-(cyclopropylmethyl)-7-(4-(2-(difluoromethoxy)-3,5-difluorophenyl)piperidin-1-yl)-[1,2,4]triazolo[4,3-b]pyridazine (45 mg, 47%). $^1$H NMR (400 MHz, CHLOROFORM-d) δ 8.22 (s, 1H), 6.90 (dt, J=9.2, 2.4 Hz, 1H), 6.84 (ddd, J=10.5, 7.8, 3.0 Hz, 1H), 6.58 (t, J=75.0 Hz, 1H), 3.79-3.67 (m, 2H), 3.33-3.25 (m, 1H), 3.21 (td, J=11.9, 2.5 Hz, 2H), 3.10 (d, J=7.0 Hz, 2H), 2.02-1.95 (m, 2H), 1.91 (td, J=12.2, 3.5 Hz, 2H), 1.36-1.20 (m, 1H), 0.59-0.50 (m, 2H), 0.40-0.32 (m, 2H). LCMS: Rt=1.01 min, (M+H)$^+$=469.9.

Example 55

8-Chloro-7-(4-(2-(difluoromethoxy)-3,5-difluorophenyl)piperidin-1-yl)-3-(2,2,2-trifluoroethyl)-[1,2,4]triazolo[4,3-b]pyridazine N'-(4-Chloro-5-(4-(2-(difluoromethoxy)-3,5-difluorophenyl)piperidin-1-yl)pyridazin-3-yl)-3,3,3-trifluoropropanehydrazide A mixture of 4-chloro-5-(4-(2-(difluoromethoxy)-3,5-difluorophenyl)piperidin-1-yl)-3-hydrazinylpyridazine (0.25 g, 0.616 mmol), ethyl acetate (50 ml), THF (25 ml), and saturated sodium carbonate (15 ml) was stirred as 3,3,3-trifluoropropanoyl chloride (0.090 g, 0.616 mmol) was added. The mixture was stirred for 20 min. The mixture was diluted with ethyl acetate and saturated sodium bicarbonate. The aqueous layer was extracted with ethyl acetate (3×20 ml). The combined organic layers were washed with saturated sodium bicarbonate (2×20 ml) and brine (20 ml), dried over magnesium sulfate, and concentrated. The residue was purified by silica gel chromatography using 0-100% ethyl acetate/hexane as the eluent to give N'-(4-chloro-5-(4-(2-(difluoromethoxy)-3,5-difluorophenyl)piperidin-1-yl)pyridazin-3-yl)-3,3,3-trifluoropropanehydrazide (0.085 g, 0.152 mmol, 24.61% yield) brown solid. $^1$H NMR (400 MHz, METHANOL-d$_4$) δ 8.48 (s, 1H), 7.08-7.00 (m, 2H), 6.81 (t, J=74.0 Hz, 1H), 3.88 (d, J=12.3 Hz, 2H), 3.35 (q, J=10.5 Hz, 2H), 3.31-3.24 (m, J=4.5 Hz, 1H), 3.17-3.04 (m, 2H), 1.97-1.86 (m, J=9.2, 3.1 Hz, 4H). LCMS: M+1=515.9.

8-Chloro-7-(4-(2-(difluoromethoxy)-3,5-difluorophenyl)piperidin-1-yl)-3-(2,2,2-trifluoroethyl)-[1,2,4]triazolo[4,3-b]pyridazine A mixture of 8-chloro-7-(4-(2-(difluoromethoxy)-3,5-difluorophenyl)piperidin-1-yl)-3-(2,2,2-trifluoroethyl)-[1,2,4]triazolo[4,3-b]pyridazine (85 mg, 0.165 mmol) and Burgess' reagent (73.9 mg, 0.310 mmol) in THF (5 mL) was stirred at 90° C. for 18 h. The reaction mixture was purified by preparative HPLC on a Phenomenex-Gemini 30×100 mm S10 column, using 20-80% water/acetonitrile containing 10 mM ammonium acetate as the eluent to give 8-chloro-7-(4-(2-(difluoromethoxy)-3,5-difluorophenyl)piperidin-1-yl)-3-(2,2,2-trifluoroethyl)-[1,2,4]triazolo[4,3-b]pyridazine (27 mg, 33.2%) as a white solid. $^1$H NMR (400 MHz, CHLOROFORM-d) δ 8.30 (s, 1H), 6.93-6.88 (m, 1H), 6.88-6.81 (m, 1H), 6.59 (t, J=75.0 Hz, 1H), 4.09 (q, J=9.8 Hz, 2H), 3.85-3.71 (m, 2H), 3.29 (br. s., 1H), 3.28-3.20 (m, 2H), 2.03-1.96 (m, 2H), 1.89 (qd, J=12.3, 3.9 Hz, 2H). LCMS: M+1=497.9.

Example 56

8-Chloro-7-(4-phenylpiperidin-1-yl)-3-(2,2,2-trifluoroethyl)-[1,2,4]triazolo[4,3-b]pyridazine N'-(4-Chloro-5-(4-phenylpiperidin-1-yl)pyridazin-3-yl)-3,3,3-trifluoropropanehydrazide A solution of 4-chloro-3-hydrazinyl-5-(4-phenylpiperidin-1-yl)pyridazine (0.15 g, 0.494 mmol) in ethyl acetate (1.5 ml), THF (3 ml), and saturated sodium bicarbonate (3 ml) was stirred as 3,3,3-trifluoropropanoyl chloride (0.056 ml, 0.543 mmol) was added. The mixture was stirred for 16 h. The reaction was diluted with ethyl acetate and water. The ethyl acetate layers was washed with water and concentrated to give N'-(4-chloro-5-(4-phenylpiperidin-1-yl)pyridazin-3-yl)-3,3,3-trifluoropropanehydrazide a brown oil. LCMS: Rt=0.82 min, (M+H)$^+$=414.08. The material was used without purification.

8-Chloro-7-(4-phenylpiperidin-1-yl)-3-(2,2,2-trifluoroethyl)-[1,2,4]triazolo[4,3-b]pyridazine A mixture of N'-(4-chloro-5-(4-phenylpiperidin-1-yl)pyridazin-3-yl)-3,3,3-trifluoropropanehydrazide (0.20 g, 0.483 mmol) and phosphorus oxychloride (0.068 ml, 0.725 mmol) in acetonitrile (5 ml) was heated to 80° C. for 16 h. The reaction was diluted with saturated sodium bicarbonate and ethyl acetate. The ethyl acetate layer was separated and concentrated to give as a brown oil. The crude material was purified via prep-HPLC using a Waters XBridge C18, 19×200 mm column, and 50-95% acetonitrile:water with 20-mM ammonium acetate as the eluent to give 8-chloro-7-(4-phenylpiperidin-1-yl)-3-(2,2,2-trifluoroethyl)-[1,2,4]triazolo[4,3-b]pyridazine (17.6 mg, 9.2%). $^1$H NMR (500 MHz, DMSO-d$_6$) δ 8.74 (s, 1H), 7.38-7.26 (m, 4H), 7.26-

7.17 (m, 1H), 4.42-4.25 (m, 2H), 3.79 (d, J=12.5 Hz, 2H), 3.21 (t, J=11.3 Hz, 2H), 2.85-2.72 (m, 1H), 1.98-1.72 (m, 4H). LCMS: Rt=1.01 min, (M+H)$^+$=396.2.

Example 57

3-Benzyl-8-chloro-7-(4-phenylpiperidin-1-yl)-[1,2,4]triazolo[4,3-b]pyridazine

N'-(4-Chloro-5-(4-phenylpiperidin-1-yl)pyridazin-3-yl)-2-phenylacetohydrazide

A solution of 2-phenylacetic acid (74 mg, 0.543 mmol) and thionyl chloride (0.18 ml, 2.469 mmol) in methylene chloride (1.5 ml) was heated to reflux for 1 h and then concentrated. A solution of residue in ethyl acetate (1.5 ml) was added to a solution of 4-chloro-3-hydrazinyl-5-(4-phenylpiperidin-1-yl)pyridazine (0.15 g, 0.494 mmol) in ethyl acetate (1.5 ml), THF (3 ml), and saturated sodium bicarbonate (3 ml). The mixture was stirred for 16 h. The reaction was diluted with ethyl acetate and water. The ethyl acetate layer was washed with water and concentrated to give N'-(4-chloro-5-(4-phenylpiperidin-1-yl)pyridazin-3-yl)-2-phenylacetohydrazide as a brown oil. LCMS: Rt=0.84 min, (M+H)$^+$=422.1. The material was used without purification.

3-Benzyl-8-chloro-7-(4-phenylpiperidin-1-yl)-[1,2,4]triazolo[4,3-b]pyridazine

A mixture of N'-(4-chloro-5-(4-phenylpiperidin-1-yl)pyridazin-3-yl)-2-phenylacetohydrazide (0.20 g, 0.474 mmol) and phosphorus oxychloride (0.066 ml, 0.711 mmol) in acetonitrile (5 ml) was heated to 80° C. for 16 h. The reaction was diluted with saturated sodium bicarbonate and ethyl acetate. The ethyl acetate layer was concentrated to a brown oil. The crude material was purified via preparative HPLC using a Waters XBridge C18, 19×200 mm column, using 55-95% acetonitrile:water with 20-mM ammonium acetate as the eluent to give 3-benzyl-8-chloro-7-(4-phenylpiperidin-1-yl)-[1,2,4]triazolo[4,3-b]pyridazine (16.9 mg, 8.8%). $^1$H NMR (500 MHz, DMSO-d$_6$) δ 8.64 (s, 1H), 7.38-7.26 (m, 8H), 7.26-7.16 (m, 2H), 4.47 (s, 2H), 3.73 (d, J=12.2 Hz, 2H), 3.24-3.10 (m, 2H), 2.83-2.69 (m, 1H), 1.96-1.71 (m, 4H). LMCS: Rt=4.30 min, (M+H)$^+$=404.3.

Example 58

8-Chloro-3-isobutyl-7-(4-phenylpiperidin-1-yl)-[1,2,4]triazolo[4,3-b]pyridazine

N'-(4-Chloro-5-(4-phenylpiperidin-1-yl)pyridazin-3-yl)-3-methylbutanehydrazide

To a solution of 3-methylbutanoic acid (0.050 g, 0.494 mmol) and thionyl chloride (0.180 ml, 2.469 mmol) in methylene chloride (1.500 ml) was heated to reflux for 1 h then concentrated. A solution of the residue in ethyl acetate (1.5 ml) was added to a solution of 4-chloro-3-hydrazinyl-5-(4-phenylpiperidin-1-yl)pyridazine (0.15 g, 0.494 mmol) in ethyl acetate (1.5 ml), THF (3 ml), and saturated sodium bicarbonate (3 ml) was stirred for 16 h. The reaction was diluted with ethyl acetate and water. The ethyl acetate layer was washed with water and concentrated to give N'-(4-chloro-5-(4-phenylpiperidin-1-yl)pyridazin-3-yl)-3-methylbutanehydrazide as a brown oil. LCMS: Rt=0.82 min, (M+H)$^+$=388.15. The material was used without purification.

8-Chloro-3-isobutyl-7-(4-phenylpiperidin-1-yl)-[1,2,4]triazolo[4,3-b]pyridazine

A mixture of N'-(4-chloro-5-(4-phenylpiperidin-1-yl)pyridazin-3-yl)-3-methylbutanehydrazide (0.200 g, 0.516 mmol) and phosphorus oxychloride (0.072 ml, 0.773 mmol) in acetonitrile (5 ml) was heated to 80° C. for 16 h. The reaction was diluted with saturated sodium bicarbonate and ethyl acetate. The ethyl acetate layer were concentrated to give a brown oil. The crude material was purified by preparative HPLC using a Waters XBridge C18, 19×200 mm column, using 60-95% methanol:water with 20-mM ammonium acetate as the eluent to give 8-chloro-3-isobutyl-7-(4-phenylpiperidin-1-yl)-[1,2,4]triazolo[4,3-b]pyridazine (10.7 mg, 5.6%). $^1$H NMR (500 MHz, DMSO-d$_6$) δ 8.63 (s, 1H), 7.38-7.27 (m, 4H), 7.26-7.13 (m, 1H), 3.73 (d, J=12.2 Hz, 2H), 3.24-3.13 (m, 2H), 2.95 (d, J=7.0 Hz, 2H), 2.84-2.69 (m, 1H), 2.30-2.14 (m, 1H), 1.98-1.73 (m, 4H), 0.95 (d, J=6.7 Hz, 6H). LCMS: Rt=4.32 min, (M+H)$^+$=370.3.

Example 59

8-Chloro-3-(2-cyclopropylethyl)-7-(4-phenylpiperidin-1-yl)-[1,2,4]triazolo[4,3-b]pyridazine N'-(4-Chloro-5-(4-phenylpiperidin-1-yl)pyridazin-3-yl)-3-cyclopropylpropanehydrazide To a solution of 3-cyclopropylpropanoic acid (0.056 g, 0.494 mmol) and thionyl chloride (0.18 ml, 2.469 mmol) in methylene chloride (1.5 ml) was heated to reflux for 1 h and then concentrated. A solution of the residue in ethyl acetate (1.5 ml) was added to a solution of 4-chloro-3-hydrazinyl-5-(4-phenylpiperidin-1-yl)pyridazine (0.15 g, 0.494 mmol) in ethyl acetate (1.5 ml), THF (3 ml), and saturated sodium bicarbonate (3 ml). The mixture was stirred for 16 h. The reaction was diluted with ethyl acetate and water. The ethyl acetate layer was washed with water and concentrated to give N'-(4-chloro-5-(4-phenylpiperidin-1-yl)pyridazin-3-yl)-3-cyclopropylpropanehydrazide as a brown oil. LMCS: Rt=0.83 min, (M+H)$^+$=400.12. The material was used without purification.

8-Chloro-3-(2-cyclopropylethyl)-7-(4-phenylpiperidin-1-yl)-[1,2,4]triazolo[4,3-b]pyridazine A mixture of N'-(4-chloro-5-(4-phenylpiperidin-1-yl)pyridazin-3-yl)-3-cyclopropylpropanehydrazide (0.200 g, 0.500 mmol) and phosphorus oxychloride (0.070 ml, 0.750 mmol) in acetonitrile (5 ml) was heated to 80° C. for 16 h. The reaction was diluted with saturated sodium bicarbonate and ethyl acetate. The ethyl acetate layer was concentrated to a brown oil. The crude material was purified by preparative HPLC using a Waters XBridge C18, 19×200 mm column, using 60-95% acetonitrile:water with 20-mM ammonium acetate as the eluent to give 8-chloro-3-(2-cyclopropylethyl)-7-(4-phenylpiperidin-1-yl)-[1,2,4]triazolo[4,3-b]pyridazine (3.5 g, 1.8%). $^1$H NMR (500 MHz, DMSO-d$_6$) δ 8.74-8.57 (m, 1H), 7.40-7.15 (m, 5H), 3.73 (d, J=11.6 Hz, 2H), 3.26-3.00 (m, 4H), 2.82-2.66 (m, 4H), 2.23-1.97 (m, 1H), 1.95-1.46 (m, 6H), 1.07-0.83 (m, 1H). LCMS: Rt=4.85 min, (M+H)$^+$=382.3.

Example 60

8-Chloro-7-(4-(2,3-dichlorophenyl)piperidin-1-yl)-3-(2,2,2-trifluoroethyl)-[1,2,4]triazolo[4,3-b]pyridazine

*N'-(4-Chloro-5-(4-(2,3-dichlorophenyl)piperidin-1-yl)pyridazin-3-yl)-3,3,3-trifluoropropanehydrazide*

A mixture of 4-chloro-5-(4-(2,3-dichlorophenyl)piperidin-1-yl)-3-hydrazinylpyridazine (0.125 g, 0.335 mmol) in ethyl acetate (1.5 ml), THF (3 ml), and saturated sodium bicarbonate (3 ml) was stirred as 3,3,3-trifluoropropanoyl chloride (0.038 ml, 0.369 mmol) was added. The mixture was stirred for 16 h. The mixture was diluted with ethyl acetate and water. The ethyl acetate layer was washed with water and concentrated to give N'-(4-chloro-5-(4-(2,3-dichlorophenyl)piperidin-1-yl)pyridazin-3-yl)-3,3,3-trifluoropropanehydrazide a brown oil. LCMS: Rt=2.15 min, $(M+H)^+$=484.1. The material was used without purification.

*8-Chloro-7-(4-(2,3-dichlorophenyl)piperidin-1-yl)-3-(2,2,2-trifluoroethyl)-[1,2,4]triazolo[4,3-b]pyridazine*

A mixture of N'-(4-chloro-5-(4-(2,3-dichlorophenyl)piperidin-1-yl)pyridazin-3-yl)-3,3,3-trifluoropropanehydrazide (0.125 g, 0.259 mmol) and phosphorus oxychloride (0.036 ml, 0.388 mmol) in acetonitrile (5 ml) was heated to 80° C. for 16 h. The reaction was diluted with saturated sodium bicarbonate and ethyl acetate. The ethyl acetate layer was concentrated to a brown oil. The crude material was purified by preparative HPLC using a Waters XBridge C18, 19×200 mm column, using 60-95% acetonitrile:water with 20-mM ammonium acetate as the eluent to give 8-chloro-7-(4-(2,3-dichlorophenyl)piperidin-1-yl)-3-(2,2,2-trifluoroethyl)-[1,2,4]triazolo[4,3-b]pyridazine (0.7 mg, 0.6%). $^1$H NMR (400 MHz, METHANOL-$d_4$) δ 8.65 (s, 1H), 7.50-7.26 (m, 3H), 4.62 (br. s., 2H), 4.23 (q, J=10.3 Hz, 2H), 3.94 (d, J=12.5 Hz, 2H)(not assigned), 3.48-3.35 (m, 2H), 2.14-1.75 (m, 5H). LCMS: Rt=4.37 min, $(M+H)^+$=464.2.

Example 61

8-Chloro-3-(cyclopropylmethyl)-N-(4-phenylcyclohexyl)-[1,2,4]triazolo[4,3-b]pyridazin-7-amine

*5-Chloro-6-hydrazinyl-N-(4-phenylcyclohexyl)pyridazin-4-amine*

A mixture of 3,4,5-trichloropyridazine (0.35 g, 1.908 mmol), 4-phenylcyclohexanamine (0.334 g, 1.908 mmol), and potassium carbonate (0.554 g, 4.01 mmol) in dioxane (6.36 ml) and water (1 ml) was heated to reflux for 1 h. The mixture was cooled and 35% hydrazine (2.469 ml, 27.3 mmol) was added. The mixture was heated to reflux for 16 h. The reaction was diluted with ethyl acetate and water. The ethyl acetate layer was washed with water and concentrated to give 5-chloro-6-hydrazinyl-N-(4-phenylcyclohexyl)pyridazin-4-amine as a dark oil. LCMS: Rt=1.95 min, $(M+H)^+$=318.2. The material was used without purification.

*N'-(4-Chloro-5-((4-phenylcyclohexyl)amino)pyridazin-3-yl)-2-cyclopropylacetohydrazide*

A mixture of 5-chloro-6-hydrazinyl-N-(4-phenylcyclohexyl)pyridazin-4-amine (0.25 g, 0.787 mmol) in ethyl acetate (1.5 ml), THF (3 ml), and saturated sodium bicarbonate (3 ml) was stirred as 2-cyclopropylacetyl chloride (0.103 g, 0.865 mmol) was added. The mixture was stirred for 16 h. The reaction was diluted with ethyl acetate and water. The ethyl acetate layers was washed with water and concentrated to a yellow solid. LCMS: Rt=0.81 min, $(M+H)^+$=400.1. The material was used without purification.

*8-Chloro-3-(cyclopropylmethyl)-N-(4-phenylcyclohexyl)-[1,2,4]triazolo[4,3-b]pyridazin-7-amine*

A solution of N'-(4-chloro-5-((4-phenylcyclohexyl)amino)pyridazin-3-yl)-2-cyclopropylacetohydrazide (0.33 g, 0.825 mmol) and phosphorus oxychloride (0.115 ml, 1.238 mmol) in acetonitrile (5 ml) was heated to 80° C. for 16 h. The reaction was cooled and diluted with saturated sodium bicarbonate and ethyl acetate. The ethyl acetate layer was concentrated to give an oil. The crude material was purified via preparative HPLC using a Waters XBridge C18, 19×200 mm column, using 5-95% acetonitrile:water with 20-mM ammonium acetate as the eluent to give 8-chloro-3-(cyclopropylmethyl)-N-(4-phenylcyclohexyl)-[1,2,4]triazolo[4,3-b]pyridazin-7-amine (8.7 mg, 2.8%). $^1$H NMR (500 MHz, DMSO-$d_6$) δ 8.65 (s, 1H), 7.37-7.10 (m, 5H), 6.15 (d, J=8.9 Hz, 1H), 3.94-3.76 (m, 1H), 2.95 (d, J=7.0 Hz, 2H), 2.03 (d, J=11.3 Hz, 2H), 1.86 (d, J=11.6 Hz, 2H), 1.72-1.51 (m, 4H), 1.26-1.12 (m, 1H), 0.58-0.43 (m, 2H), 0.27 (d, J=5.2 Hz, 2H). LCMS: Rt=4.62 min, $(M+H)^+$=383.3.

Example 62

1'-(8-Chloro-3-(cyclopropylmethyl)-[1,2,4]triazolo[4,3-b]pyridazin-7-yl)-2H-spiro[benzofuran-3,4'-piperidin]-2-one

*1'-(5-Chloro-6-hydrazinylpyridazin-4-yl)-2H-spiro[benzofuran-3,4'-piperidin]-2-one*

A mixture of 3,4,5-trichloropyridazine (0.35 g, 1.908 mmol), 2H-spiro[benzofuran-3,4'-piperidin]-2-one hydrochloride (0.457 g, 1.908 mmol), and potassium carbonate (0.554 g, 4 mmol) in dioxane (6.36 ml) and water (1 ml) was heated to reflux for 1 h. The mixture was cooled and 35% hydrazine (2.469 ml, 27.3 mmol) was added. The mixture was heated to reflux for 16 h. The reaction was diluted with ethyl acetate and water. The ethyl acetate layer was washed with water and concentrated to give 1'-(5-chloro-6-hydrazinylpyridazin-4-yl)-2H-spiro[benzofuran-3,4'-piperidin]-2-one as a yellow oil. LCMS: Rt=1.67 min, $(M+H)^+$=346.2. The material was used without purification.

*N'-(4-Chloro-5-(2-oxo-2H-spiro[benzofuran-3,4'-piperidin]-1'-yl)pyridazin-3-yl)-2-cyclopropylacetohydrazide*

A mixture of 1'-(5-chloro-6-hydrazinylpyridazin-4-yl)-2H-spiro[benzofuran-3,4'-piperidin]-2-one (0.25 g, 0.723 mmol) in ethyl acetate (1.5 ml), THF (3 ml), and saturated sodium bicarbonate (3 ml) was stirred as 2-cyclopropylacetyl chloride (0.094 g, 0.795 mmol) was added. The mixture was stirred for 16 h. The reaction was diluted with ethyl acetate and water. The ethyl acetate layer was washed with water and concentrated to give N'-(4-chloro-5-(2-oxo-2H-spiro[benzofuran-3,4'-piperidin]-1'-yl)pyridazin-3-yl)-2-cyclopropylacetohydrazide as a yellow solid. LCMS: Rt=0.75 min, $(M+H)^+$=428.1. The material was used without purification.

1'-(8-Chloro-3-(cyclopropylmethyl)-[1,2,4]triazolo [4,3-b]pyridazin-7-yl)-2H-spiro[benzofuran-3,4'-piperidin]-2-one A solution of N'-(4-chloro-5-(2-oxo-2H-spiro[benzofuran-3,4'-piperidin]-1'-yl)pyridazin-3-yl)-2-cyclopropylacetohydrazide (0.309 g, 0.722 mmol) and phosphorus oxychloride (0.101 ml, 1.083 mmol) in acetonitrile (5 ml) was heated to 80° C. for 16 h. The reaction was cooled and diluted with saturated sodium bicarbonate and ethyl acetate. The ethyl acetate layer was concentrated to give an oil. The crude material was purified via preparative HPLC using a Waters XBridge C18, 19×200 mm, using 30-95% acetonitrile:water with 20-mM ammonium acetate as the eluent to give 1'-(8-chloro-3-(cyclopropylmethyl)-[1,2,4]triazolo[4,3-b]pyridazin-7-yl)-2H-spiro[benzofuran-3,4'-piperidin]-2-one (1.8 mg, 0.6%). $^1$H NMR (500 MHz, DMSO-d$_6$) δ 8.80-8.66 (m, 1H), 7.80-7.67 (m, 1H), 7.48-7.37 (m, 1H), 7.32-7.21 (m, 2H), 3.97-3.86 (m, 1H), 3.75-3.58 (m, 3H), 3.11-2.96 (m, 2H), 2.18-2.02 (m, 4H), 1.32-1.11 (m, 1H), 0.58-0.43 (m, 2H), 0.35-0.23 (m, 2H). LCMS: Rt=0.92 min, (M+H)$^+$=410.1.

Example 63

1'-(8-Chloro-3-(2,2,2-trifluoroethyl)-[1,2,4]triazolo [4,3-b]pyridazin-7-yl)-2H-spiro[benzofuran-3,4'-piperidin]-2-one

N'-(4-Chloro-5-(2-oxo-2H-spiro[benzofuran-3,4'-piperidin]-1'-yl)pyridazin-3-yl)-3,3,3-trifluoropropanehydrazide A solution of 1'-(5-chloro-6-hydrazinylpyridazin-4-yl)-2H-spiro[benzofuran-3,4'-piperidin]-2-one (0.25 g, 0.723 mmol) in ethyl acetate (1.5 ml), THF (3 ml), and saturated sodium bicarbonate (3 ml) was stirred as 3,3,3-trifluoropropanoyl chloride (0.082 ml, 0.795 mmol) was added. The mixture was stirred for 16 h. The reaction was diluted with ethyl acetate and water. The ethyl acetate layer was washed with water and concentrated to give N'-(4-chloro-5-(2-oxo-2H-spiro[benzofuran-3,4'-piperidin]-1'-yl)pyridazin-3-yl)-3,3,3-trifluoropropanehydrazide a yellow solid. LCMS: Rt=1.70 min, (M+H)$^+$=454.2. The material was used without purification.

1'-(8-Chloro-3-(2,2,2-trifluoroethyl)-[1,2,4]triazolo [4,3-b]pyridazin-7-yl)-2H-spiro[benzofuran-3,4'-piperidin]-2-one A solution of N'-(4-chloro-5-(2-oxo-2H-spiro[benzofuran-3,4'-piperidin]-1'-yl)pyridazin-3-yl)-3,3,3-trifluoropropanehydrazide (0.309 g, 0.678 mmol) and phosphorus oxychloride (0.095 ml, 1.017 mmol) in acetonitrile (5 ml) was heated to 80° C. for 16 h. The reaction was cooled and diluted with saturated sodium bicarbonate and ethyl acetate. The ethyl acetate layer was concentrated. The crude material was purified via preparative HPLC using a Waters XBridge C18, 19×200 mm column and 40-95% acetonitrile:water with 20-mM ammonium acetate as the eluent, to give 1'-(8-chloro-3-(2,2,2-trifluoroethyl)-[1,2,4]triazolo[4,3-b] pyridazin-7-yl)-2H-spiro[benzofuran-3,4'-piperidin]-2-one (5.5 g, 1.8%). $^1$H NMR (500 MHz, DMSO-d$_6$) δ 8.88-8.75 (m, 1H), 7.73 (d, J=7.3 Hz, 1H), 7.46-7.36 (m, 1H), 7.33-7.18 (m, 2H), 4.36 (q, J=10.8 Hz, 2H), 3.70 (dt, J=11.1, 5.6 Hz, 4H), 2.11 (t, J=5.5 Hz, 4H). LCMS: Rt=0.94 min, (M+H)$^+$=438.1.

Example 64

8-Chloro-N-(4-phenylcyclohexyl)-3-(2,2,2-trifluoroethyl)-[1,2,4]triazolo[4,3-b]pyridazin-7-amine

N'-(4-Chloro-5-((4-phenylcyclohexyl)amino) pyridazin-3-yl)-3,3,3-trifluoropropanehydrazide A solution of 5-chloro-6-hydrazinyl-N-(4-phenylcyclohexyl)pyridazin-4-amine (0.25 g, 0.787 mmol) in ethyl acetate (1.5 ml), THF (3 ml), and saturated sodium bicarbonate (3 ml) was stirred as 3,3,3-trifluoropropanoyl chloride (0.089 ml, 0.865 mmol) was added. The mixture was stirred 16 h. The reaction was diluted with ethyl acetate and water. The ethyl acetate layer was washed with water and concentrated to give N'-(4-chloro-5-((4-phenylcyclohexyl)amino)pyridazin-3-yl)-3,3,3-trifluoropropanehydrazide as a yellow solid. LCMS: Rt=0.83 min, (M+H)$^+$=428.1. The material was used without purification.

8-Chloro-N-(4-phenylcyclohexyl)-3-(2,2,2-trifluoroethyl)-[1,2,4]triazolo[4,3-b]pyridazin-7-amine A solution of N'-(4-chloro-5-((4-phenylcyclohexyl) amino)pyridazin-3-yl)-3,3,3-trifluoropropanehydrazide (0.330 g, 0.771 mmol) and phosphorus oxychloride (0.108 ml, 1.157 mmol) in acetonitrile (5 ml) heated to 80° C. for 16 h. The reaction was cooled and diluted with saturated sodium bicarbonate and ethyl acetate. The ethyl acetate layer was concentrated. The crude material was purified via preparative HPLC using a Waters XBridge C18, 19×200 mm column and 40-80% acetonitrile:water with 20-mM ammonium acetate as the eluent, to give 8-chloro-N-(4-phenylcyclohexyl)-3-(2,2,2-trifluoroethyl)-[1,2,4]triazolo[4,3-b] pyridazin-7-amine (1.5 mg, 0.475%). $^1$H NMR (500 MHz, DMSO-d$_6$) δ 8.75 (s, 1H), 7.38-7.13 (m, 5H), 6.34 (d, J=8.9 Hz, 1H), 4.26 (q, J=10.5 Hz, 2H), 3.89 (d, J=12.2 Hz, 2H), 2.03 (d, J=10.7 Hz, 2H), 1.93-1.78 (m, 2H), 1.73-1.53 (m, 4H). LCMS: Rt=1.00 min, (M+H)$^+$=410.1.

Example 65

8-Chloro-3-(cyclopropylmethyl)-7-(4-(2-(trifluoromethyl)phenyl)piperidin-1-yl)-[1,2,4]triazolo[4,3-b] pyridazine

4-Chloro-3-hydrazinyl-5-(4-(2-(trifluoromethyl)phenyl)piperidin-1-yl)pyridazine A mixture of 3,4,5-trichloropyridazine (0.35 g, 1.908 mmol), 4-(2-(trifluoromethyl)phenyl)piperidine (0.437 g, 1.908 mmol), and potassium carbonate (0.554 g, 4 mmol) in dioxane (6.36 ml) and 1 ml water was heated to reflux for 16 h. The reaction was diluted with ethyl acetate and water. The ethyl acetate layer was washed with water and concentrated to give 4-chloro-3-hydrazinyl-5-(4-(2-(trifluoromethyl)phenyl)piperidin-1-yl)pyridazine an orange oil. LCMS: Rt=0.84 min, (M+H)$^+$=372.1. The material was used without purification.

N'-(4-Chloro-5-(4-(2-(trifluoromethyl)phenyl)piperidin-1-yl)pyridazin-3-yl)-2-cyclopropylacetohydrazide A mixture of 4-chloro-3-hydrazinyl-5-(4-(2-(trifluoromethyl)phenyl)piperidin-1-yl)pyridazine (0.25 g, 0.672 mmol) in ethyl acetate (2.5 ml), THF (5 ml), and saturated sodium bicarbonate (5 ml) was stirred as a solution of 2-cyclopropylacetyl chloride (0.088 g, 0.74 mmol) in ethyl acetate (2.5 ml) was added. The mixture was stirred for 16 h. The reaction was diluted with ethyl acetate and water. The ethyl acetate layer was washed with water and concentrated to give N'-(4-chloro-5-(4-(2-(trifluoromethyl)phenyl)piperidin-1-yl)pyridazin-3-yl)-2-cyclopropylacetohydrazide as a brown oil. LCMS: Rt=0.88 min, (M+H)$^+$=454.1.

8-Chloro-3-(cyclopropylmethyl)-7-(4-(2-(trifluoromethyl)phenyl)piperidin-1-yl)-[1,2,4]triazolo[4,3-b]pyridazine A solution of N'-(4-chloro-5-(4-(2-(trifluoromethyl)phenyl)piperidin-1-yl)pyridazin-3-yl)-2-cyclopropylacetohydrazide (0.25 g, 0.551 mmol) and phosphorus oxychloride (0.077 ml, 0.826 mmol) in acetonitrile (4 ml) was heated to 80° C. for 16 h. The reaction was diluted with ethyl acetate and water. The ethyl acetate layer was washed with water and concentrated to give a brown oil. The crude material was purified via preparative HPLC on a Waters XBridge C18 column, 19×200 mm column, using 60-95% acetonitrile:water with 20-mM ammonium acetate as the eluent, to give 8-chloro-3-(cyclopropylmethyl)-7-(4-(2-(trifluoromethyl)phenyl)piperidin-1-yl)-[1,2,4]triazolo[4,3-b]pyridazine (8.8 mg, 3.41%). $^1$H NMR (500 MHz, DMSO-d$_6$) δ 8.89 (s, 1H), 8.56 (s, 1H), 7.65 (d, J=12.2 Hz, 3H), 7.40 (br. s., 1H), 3.21-2.91 (m, 7H), 1.99-1.70 (m, 5H), 1.18 (br. s., 1H), 0.46 (d, J=6.1 Hz, 1H), 0.24 (br. s., 1H). LCMS: Rt=1.03 min, (M+H)$^+$=436.1.

Example 66

8-Chloro-3-(2,2,2-trifluoroethyl)-7-(4-(2-(trifluoromethyl)phenyl)piperidin-1-yl)-[1,2,4]triazolo[4,3-b]pyridazine N'-(4-Chloro-5-(4-(2-(trifluoromethyl)phenyl)piperidin-1-yl)pyridazin-3-yl)-3,3,3-trifluoropropanehydrazide A mixture of 4-chloro-3-hydrazinyl-5-(4-(2-(trifluoromethyl)phenyl)piperidin-1-yl)pyridazine (0.25 g, 0.672 mmol) in ethyl acetate (2.5 ml), THF (5 ml), and saturated sodium bicarbonate (5 ml) was stirred as a solution of 3,3,3-trifluoropropanoyl chloride (0.076 ml, 0.740 mmol) in ethyl acetate (2.5 ml) was added. The mixture was stirred for 16 h. The reaction was diluted with ethyl acetate and water. The ethyl acetate layer was washed with water and concentrated to give N'-(4-chloro-5-(4-(2-(trifluoromethyl)phenyl)piperidin-1-yl)pyridazin-3-yl)-3,3,3-trifluoropropanehydrazide as a brown oil. LCMS: Rt=0.89 min, (M+H)$^+$=482.1.

8-Chloro-3-(2,2,2-trifluoroethyl)-7-(4-(2-(trifluoromethyl)phenyl)piperidin-1-yl)-[1,2,4]triazolo[4,3-b]pyridazine A solution of N'-(4-chloro-5-(4-(2-(trifluoromethyl)phenyl)piperidin-1-yl)pyridazin-3-yl)-3,3,3-trifluoropropanehydrazide (0.25 g, 0.519 mmol) and phosphorus oxychloride (0.073 ml, 0.778 mmol) in acetonitrile (4 ml) as heated to 80° C. for 16 h. The reaction was diluted with ethyl acetate and water. The ethyl acetate layer was washed with water and concentrated to give a brown oil. The crude material was purified via preparative HPLC on a Waters XBridge C18, 19×200 mm column, using 20-95% acetonitrile:water with 20-mM ammonium acetate as the eluent, to give 8-chloro-3-(2,2,2-trifluoroethyl)-7-(4-(2-(trifluoromethyl)phenyl)piperidin-1-yl)-[1,2,4]triazolo[4,3-b]pyridazine (14.3 mg, 5.94%). $^1$H NMR (500 MHz, DMSO-d$_6$) δ 8.73 (s, 1H), 7.69 (t, J=8.4 Hz, 3H), 7.44 (t, J=7.2 Hz, 1H), 4.44-4.24 (m, 2H), 3.80 (d, J=12.2 Hz, 2H), 3.21 (t, J=11.6 Hz, 2H), 3.06 (br. s., 1H), 1.97 (d, J=11.3 Hz, 2H), 1.83 (d, J=11.6 Hz, 2H). LCMS: Rt=1.07 min, (M+H)$^+$=464.1.

Example 67

8-Chloro-7-(4-(2-fluorophenyl)piperidin-1-yl)-3-(2,2,2-trifluoroethyl)-[1,2,4]triazolo[4,3-c]pyrimidine 4-(4-(2-Fluorophenyl)piperidin-1-yl)-6-hydrazinylpyrimidine A mixture of 4,6-dichloropyrimidine (0.50 g, 3.36 mmol), 4-(2-fluorophenyl)piperidine hydrochloride (0.724 g, 3.36 mmol), and potassium carbonate (0.974 g, 7.05 mmol) in dioxane (10 ml) and water (1 ml) was stirred for 1 hr and then heated to 100° C. for 1 h. The mixture was cooled and 35% hydrazine (6.08 ml, 67.1 mmol) was added. The mixture was heated to reflux for 16 hr overnight. The mixture was cooled, diluted with water and extracted with ethyl acetate. The ethyl acetate layer was concentrated to give 4-(4-(2-fluorophenyl)piperidin-1-yl)-6-hydrazinylpyrimidine as a white solid. LCMS: Rt=1.94 min, (M+H)$^+$=288.3. The material was used without purification.

3,3,3-Trifluoro-N'-(6-(4-(2-fluorophenyl)piperidin-1-yl)pyrimidin-4-yl)propanehydrazide A solution of 4-(4-(2-fluorophenyl)piperidin-1-yl)-6-hydrazinylpyrimidine (0.25 g, 0.87 mmol) in ethyl acetate (1.5 ml), THF (3 ml), and saturated sodium bicarbonate (3 ml) was stirred as 3,3,3-trifluoropropanoyl chloride (0.099 ml, 0.957 mmol) was added. The mixture was stirred 16 h. The reaction was diluted with ethyl acetate and water. The ethyl acetate layer was washed with water and concentrated to give 3,3,3-trifluoro-N'-(6-(4-(2-fluorophenyl)piperidin-1-yl)pyrimidin-4-yl)propanehydrazide. LCMS: Rt=0.81 min, (M+H)$^+$=398.2. The material was used without purification.

N'-(5-Chloro-6-(4-(2-fluorophenyl)piperidin-1-yl)pyrimidin-4-yl)-3,3,3-trifluoropropanehydrazide A solution of 3,3,3-trifluoro-N'-(6-(4-(2-fluorophenyl)piperidin-1-yl)pyrimidin-4-yl)propanehydrazide (0.32 g, 0.805 mmol) in THF (6.15 ml) was stirred as NCS (0.108 g, 0.805 mmol) was added. The reaction was stirred for 16 h. The reaction was diluted with ethyl acetate and water. The ethyl acetate layer was separated, washed with water, and concentrated to give N'-(5-chloro-6-(4-(2-fluorophenyl)piperidin-1-yl)pyrimidin-4-yl)-3,3,3-trifluoropropanehydrazide as an orange solid. LCMS: Rt=2.13 min, (M+H)$^+$=432.1. The material was used without purification.

8-Chloro-7-(4-(2-fluorophenyl)piperidin-1-yl)-3-(2,2,2-trifluoroethyl)-[1,2,4]triazolo[4,3-c]pyrimidine A solution of N'-(5-chloro-6-(4-(2-fluorophenyl)piperidin-1-yl)pyrimidin-4-yl)-3,3,3-trifluoropropanehydrazide (0.16 g, 0.371 mmol), triphenylphosphine (0.117 g, 0.445 mmol), and azidotrimethylsilane (0.098 ml, 0.741 mmol) in methylene chloride (2 ml) was stirred in a cool water bath as 40% DEAD in toluene (0.506 ml, 1.112 mmol) was added.

The reaction mixture was applied directly to a silica gel column, and the product was eluted with 0-100% ethyl acetate/methylene chloride to give 8-chloro-7-(4-(2-fluorophenyl)piperidin-1-yl)-3-(2,2,2-trifluoroethyl)-[1,2,4]triazolo[4,3-c]pyrimidine (1.1 g, 0.682%) as a light yellow oil. $^1$H NMR (500 MHz, METHANOL-d$_4$) δ 9.10 (s, 1H), 7.37-7.31 (m, 1H), 7.27-7.21 (m, 1H), 7.17-7.12 (m, 1H), 7.09-7.04 (m, 1H), 4.49 (d, J=12.8 Hz, 2H), 4.33 (q, J=10.2 Hz, 2H), 3.28-3.09 (m, 3H), 2.01-1.84 (m, 4H). LCMS: Rt=1.01 min, (M+H)$^+$=414.1.

Example 68

8-Chloro-3-(cyclopropylmethyl)-7-(4-(2-fluorophenyl)piperidin-1-yl)-[1,2,4]triazolo[4,3-c]pyrimidine 2-Cyclopropyl-N'-(6-(4-(2-fluorophenyl)piperidin-1-yl)pyrimidin-4-yl)acetohydrazide A solution of 4-(4-(2-fluorophenyl)piperidin-1-yl)-6-hydrazinylpyrimidine (0.25 g, 0.87 mmol) in ethyl acetate (1.5 ml), THF (3 ml), and saturated sodium bicarbonate (3 ml) was stirred as 2-cyclopropylacetyl chloride (0.113 g, 0.957 mmol) was added. The mixture was stirred for 16 h. The reaction was diluted with ethyl acetate and water. The ethyl acetate layer was washed with water and concentrated to give 2-cyclopropyl-N'-(6-(4-(2-fluorophenyl)piperidin-1-yl)pyrimidin-4-yl)acetohydrazide. LCMS: Rt=0.80 min, (M+H)$^+$=370.2. The material was used without purification.

N'-(5-Chloro-6-(4-(2-fluorophenyl)piperidin-1-yl)pyrimidin-4-yl)-2-cyclopropylacetohydrazide A solution of 2-cyclopropyl-N'-(6-(4-(2-fluorophenyl)piperidin-1-yl)pyrimidin-4-yl)acetohydrazide (0.320 g, 0.866 mmol) in THF (6.61 ml) was stirred as NCS (0.116 g, 0.866 mmol) was added. The mixture was stirred for 16 h. The reaction was diluted with ethyl acetate and water. The ethyl acetate layer was separated, washed with water, and concentrated to give N'-(5-chloro-6-(4-(2-fluorophenyl)piperidin-1-yl)pyrimidin-4-yl)-2-cyclopropylacetohydrazide as an orange solid. LCMS: Rt=1.87 min, (M+H)$^+$=465.3. The material was used without purification.

8-Chloro-3-(cyclopropylmethyl)-7-(4-(2-fluorophenyl)piperidin-1-yl)-[1,2,4]triazolo[4,3-c]pyrimidine A solution of N'-(5-chloro-6-(4-(2-fluorophenyl)piperidin-1-yl)pyrimidin-4-yl)-2-cyclopropylacetohydrazide (0.275 g, 0.681 mmol), triphenylphosphine (0.214 g, 0.817 mmol), and azidotrimethylsilane (0.181 ml, 1.362 mmol) in methylene chloride (4 ml) was stirred in a cool water bath as 40% DEAD in toluene (0.93 ml, 2.043 mmol) was added. Effervescence occurred. The reaction mixture was applied to a silica gel column, and the product was eluted with 0-100% ethyl acetate/methylene chloride. The product fractions were concentrated. The product was further purified by preparative HPLC on an XBridge OBD 19×100 mm column, using 30-95% acetonitrile/water containing 10 mM ammonium acetate as the eluent. The product fractions were combined, extracted with ethyl acetate and concentrated to give 8-chloro-3-(cyclopropylmethyl)-7-(4-(2-fluorophenyl)piperidin-1-yl)-[1,2,4]triazolo[4,3-c]pyrimidine (9.4 g, 3.2%). $^1$H NMR (400 MHz, METHANOL-d$_4$) δ 9.01 (s, 1H), 7.38-6.98 (m, 5H), 4.49-4.35 (m, 2H), 3.28-3.15 (m, 3H), 3.09 (d, J=6.8 Hz, 2H), 1.98-1.87 (m, 4H), 0.74-0.57 (m, 2H), 0.44-0.28 (m, 2H). LCMS: Rt=0.91, (M+H)$^+$=386.2.

Example 69

8-Chloro-7-(4-(4-fluorophenyl)piperidin-1-yl)-3-(2,2,2-trifluoroethyl)-[1,2,4]triazolo[4,3-c]pyrimidine 4-(4-(4-Fluorophenyl)piperidin-1-yl)-6-hydrazinylpyrimidine A mixture of 4,6-dichloropyrimidine (0.50 g, 3.36 mmol), 4-(4-fluorophenyl)piperidine hydrochloride (0.724 g, 3.36 mmol), and potassium carbonate (0.974 g, 7.05 mmol) in dioxane (10 ml) and water (1 ml) was stirred at room temperature for 1 h and then heated to 100° C. for 1 h. The mixture was cooled and 35% hydrazine (6.08 ml, 67.1 mmol) was added. The mixture was heated to reflux for 16 h. The mixture was cooled, diluted with water and extracted with ethyl acetate. The ethyl acetate layer was concentrated to give 4-(4-(4-fluorophenyl)piperidin-1-yl)-6-hydrazinylpyrimidine as a yellow solid. LCMS: Rt=0.81 min. (M+H)$^+$=288.1.

3,3,3-Trifluoro-N'-(6-(4-(4-fluorophenyl)piperidin-1-yl)pyrimidin-4-yl)propanehydrazide A solution of -(4-(4-fluorophenyl)piperidin-1-yl)-6-hydrazinylpyrimidine (0.5 g, 1.74 mmol) in ethyl acetate (2.5 ml), THF (5 ml), and saturated sodium bicarbonate (5 ml) was stirred as 3,3,3-trifluoropropanoyl chloride (0.197 ml, 1.914 mmol) was added. The mixture was stirred for 32 h. The reaction was diluted with ethyl acetate and water. The ethyl acetate layer was separated, washed with water, and concentrated to give 3,3,3-trifluoro-N'-(6-(4-(4-fluorophenyl)piperidin-1-yl)pyrimidin-4-yl)propanehydrazide as a brown oil. LCMS: Rt=0.83 min, (M+H)$^+$=398.1. The material was used without purification.

N'-(5-Chloro-6-(4-(4-fluorophenyl)piperidin-1-yl)pyrimidin-4-yl)-3,3,3-trifluoropropanehydrazide A solution of 3,3,3-trifluoro-N'-(6-(4-(4-fluorophenyl)piperidin-1-yl)pyrimidin-4-yl)propanehydrazide (0.691 g, 1.739 mmol) in THF (13 ml) was stirred as NCS (0.232 g, 1.739 mmol) was added. The mixture was stirred for 16 h. The reaction was diluted with ethyl acetate and water. The ethyl acetate layer was separated, washed with water, and concentrated to give N'-(5-chloro-6-(4-(4-fluorophenyl)piperidin-1-yl)pyrimidin-4-yl)-3,3,3-trifluoropropanehydrazide as a brown oil. LCMS: Rt=0.95 min, (M+H)$^+$=432.1. The material was used without purification.

8-Chloro-7-(4-(4-fluorophenyl)piperidin-1-yl)-3-(2,2,2-trifluoroethyl)-[1,2,4]triazolo[4,3-c]pyrimidine A solution of N'-(5-chloro-6-(4-(4-fluorophenyl)piperidin-1-yl)pyrimidin-4-yl)-3,3,3-trifluoropropanehydrazide (0.75 g, 1.737 mmol), triphenylphosphine (0.547 g, 2.084 mmol), and azidotrimethylsilane (0.461 ml, 3.47 mmol) in methylene chloride (4 ml) was stirred as 40% DEAD in toluene (2.37 ml, 5.21 mmol) was added. Effervescence occurred and the solution was stirred for 1 h. The reaction mixture was applied to a silica gel column and the product was eluted with 0-100% ethyl acetate/hexane. The product fractions were concentrated to an oil. The product was further purified by preparative HPLC on an XBridge OBD 19×100 mm column, using 30-95% acetonitrile/water containing 10 mM ammonium acetate as the eluent to give 8-chloro-7-(4-(4-fluorophenyl)piperidin-1-yl)-3-(2,2,2-trifluoroethyl)-[1,2,4]triazolo[4,3-c]pyrimidine (2.2 mg, 0.3%). $^1$H NMR (500 MHz, METHANOL-$d_4$) δ 9.09 (s, 1H), 7.30 (dd, J=8.5, 5.3 Hz, 2H), 7.11-7.00 (m, 2H), 4.48 (d, J=13.0 Hz, 2H), 4.33 (q, J=10.2 Hz, 2H), 3.26-3.15 (m, 2H), 2.95-2.80 (m, 1H), 2.09-1.76 (m, 4H). LCMS: Rt=0.75 min, (M+H)$^+$=414.2.

Example 70

3-(Cyclopropylmethyl)-7-(4-(2-fluoro-6-methoxyphenyl)piperidin-1-yl)-8-(trifluoromethyl)-[1,2,4]triazolo[4,3-b]pyridazine 4-Bromo-5-(4-(2-fluoro-6-methoxyphenyl)piperidin-1-yl)pyridazin-3(2H)-one A solution of 4,5-dibromopyridazin-3(2H)-one (0.30 g, 1.182 mmol), 4-(2-fluoro-6-methoxyphenyl)piperidine (0.272 g, 1.3 mmol), and DIPEA (0.454 ml, 2.6 mmol) in DMA (2.5 ml) was heated to 100° C. for 16 h. The reaction was cooled and diluted with saturated sodium bicarbonate to give a precipitate. The precipitate was filtered and dried to give 4-bromo-5-(4-(2-fluoro-6-methoxyphenyl)piperidin-1-yl)pyridazin-3(2H)-one. LCMS: Rt=0.96 min, (M+H)$^+$=384. The material was used without purification.

tert-Butyl 5-bromo-4-(4-(2-fluoro-6-methoxyphenyl)piperidin-1-yl)-6-oxopyridazine-1(6H)-carboxylate A solution of 4-bromo-5-(4-(2-fluoro-6-methoxyphenyl)piperidin-1-yl)pyridazin-3(2H)-one (0.452 g, 1.183 mmol), di-tert-butyl dicarbonate (0.31 g, 1.419 mmol) and triethylamine (0.247 ml, 1.774 mmol) in methylene chloride (50 ml) was stirred for 16 h. The solution was washed with water. The methylene chloride layer was separated, dried over magnesium sulfate, and concentrated to give tert-butyl 5-bromo-4-(4-(2-fluoro-6-methoxyphenyl)piperidin-1-yl)-6-oxopyridazine-1(6H)-carboxylate as a brown oil. $^1$H NMR (500 MHz, METHANOL-$d_4$) δ 7.89 (s, 1H), 7.20 (td, J=8.3, 6.6 Hz, 1H), 6.81 (d, J=8.4 Hz, 1H), 6.69 (ddd, J=10.8, 8.4, 0.8 Hz, 1H), 3.86 (s, 3H), 3.22 (t, J=12.6 Hz, 2H), 2.69 (q, J=7.2 Hz, 3H), 2.39 (dd, J=12.3, 3.4 Hz, 2H), 1.75 (d, J=10.5 Hz, 2H), 1.66-1.57 (m, 9H). LCMS: Rt=1.11 min, (M+H)$^+$=382. The material was used without purification.

tert-Butyl 4-(4-(2-fluoro-6-methoxyphenyl)piperidin-1-yl)-6-oxo-5-(trifluoromethyl)pyridazine-1(6H)-carboxylate A mixture of tert-butyl 5-bromo-4-(4-(2-fluoro-6-methoxyphenyl)piperidin-1-yl)-6-oxopyridazine-1(6H)-carboxylate (0.57 g, 1.182 mmol), copper(I) iodide (0.45 g, 2.363 mmol), and methyl 2,2-difluoro-2-(fluorosulfonyl)acetate (0.299 ml, 2.363 mmol) in DMF (10.8 ml) was heated to 100° C. for 1 h. The mixture was filtered through a pad of silica gel, and the pad was rinsed with ethyl acetate. The filtrate was washed with saturated ammonium chloride. The ethyl acetate layer was concentrated to give tert-butyl 4-(4-(2-fluoro-6-methoxyphenyl)piperidin-1-yl)-6-oxo-5-(trifluoromethyl)pyridazine-1(6H)-carboxylate as a brown oil. LCMS: Rt=0.96 min, (M+H)$^+$=372.1. The material was used without purification.

3-Chloro-5-(4-(2-fluoro-6-methoxyphenyl)piperidin-1-yl)-4-(trifluoromethyl)pyridazine A solution of tert-butyl 4-(4-(2-fluoro-6-methoxyphenyl)piperidin-1-yl)-6-oxo-5-(trifluoromethyl)pyridazine-1(6H)-carboxylate (0.50 g, 1.061 mmol) and phosphorus oxychloride (6 ml, 35.0 mmol) was heated to 100° C. for 11 h. The reaction was concentrated. The residue was dissolved in methylene chloride and washed with saturated sodium bicarbonate. The organic layers were combined, dried with magnesium sulfate, filtered and concentrated to give 3-chloro-5-(4-(2-fluoro-6-methoxyphenyl)piperidin-1-yl)-4-(trifluoromethyl)pyridazine as a brown oil. LCMS: Rt=1.10 min, (M+H)$^+$=390.1. The material was used without purification.

5-(4-(2-Fluoro-6-methoxyphenyl)piperidin-1-yl)-3-hydrazinyl-4-(trifluoromethyl)pyridazine A mixture of 3-chloro-5-(4-(2-fluoro-6-methoxyphenyl)piperidin-1-yl)-4-(trifluoromethyl)pyridazine (0.40 g, 1.026 mmol), potassium carbonate (0.298 g, 2.155 mmol), and 35% hydrazine (1.86 ml, 20.52 mmol) in dioxane (10 ml) was heated to 100° C. for 2 h. The mixture was cooled, diluted with water and extracted with ethyl acetate. The ethyl acetate layer was concentrated to give 5-(4-(2-fluoro-6-methoxyphenyl)piperidin-1-yl)-3-hydrazinyl-4-(trifluoromethyl)pyridazine. LCMS: Rt=0.84 min, (M+H)$^+$=386.2. The material was used without purification.

2-Cyclopropyl-N'-(5-(4-(2-fluoro-6-methoxyphenyl)piperidin-1-yl)-4-(trifluoromethyl)pyridazin-3-yl)acetohydrazide A solution of 5-(4-(2-fluoro-6-methoxyphenyl)piperidin-1-yl)-3-hydrazinyl-4-(trifluoromethyl)pyridazine (0.20 g, 0.519 mmol) in ethyl acetate (2.5 ml), THF (5 ml), and saturated sodium bicarbonate (5 ml) was stirred as 2-cyclopropylacetyl chloride (0.068 g, 0.571 mmol) was added. The mixture was stirred for 16 h. The reaction was diluted with ethyl acetate and water. The ethyl acetate layer was separated, washed with water, and concentrated to give 2-cyclopropyl-N'-(5-(4-(2-fluoro-6-methoxyphenyl)piperidin-1-yl)-4-(trifluoromethyl)pyridazin-3-yl)acetohydrazide as a semisolid. LCMS: Rt=0.86 min, (M+H)$^+$=468.2.

3-(Cyclopropylmethyl)-7-(4-(2-fluoro-6-methoxyphenyl)piperidin-1-yl)-8-(trifluoromethyl)-[1,2,4]triazolo[4,3-b]pyridazine A solution of 2-cyclopropyl-N'-(5-(4-(2-fluoro-6-methoxyphenyl)piperidin-1-yl)-4-(trifluoromethyl)pyridazin-3-yl)acetohydrazide (0.25 g, 0.535 mmol) and [Reactants], triphenylphosphine (0.168 g, 0.642 mmol), and azidotrimethylsilane (0.142 ml, 1.070 mmol) in methylene chloride (4 ml) was stirred in a cold water bath as 40% DEAD in toluene (0.731 ml, 1.604 mmol) was added. Effervescence occurred. The reaction was stirred for 1 h. The reaction mixture was applied to a silica gel column and the product was eluted with 0-100% ethyl acetate/hexane. The product fractions were concentrated to an oil. The product was further purified by preparative HPLC on an XBridge OBD 19×100 mm column, using 10-95% acetonitrile/water containing 10 mM ammonium acetate as the eluent to give 3-(cyclopropylmethyl)-7-(4-(2-fluoro-6-methoxyphenyl)piperidin-1-yl)-8-(trifluoromethyl)-[1,2,4]triazolo[4,3-b]pyridazine as a yellow oil (7.9 mg, 3.3%). $^1$H NMR (500

MHz, DMSO-d$_6$) δ 8.73 (br. s., 1H), 7.94 (br. s., 1H), 7.23 (d, J=7.3 Hz, 1H), 6.93-6.70 (m, 1H), 2.96 (d, J=5.8 Hz, 5H), 2.89 (br. s., 4H), 2.73 (br. s., 3H), 2.22 (d, J=11.9 Hz, 2H), 1.66 (d, J=11.9 Hz, 2H), 1.21 (d, J=17.4 Hz, 1H), 0.49 (br. s., 1H), 0.28 (br. s., 1H). LCMS: RT=0.99 min, 450.1.

Example 71

3-(Cyclopropylmethyl)-7-(4-(2-fluoro-6-methoxyphenyl)piperidin-1-yl)-8-(trifluoromethyl)-[1,2,4]triazolo[4,3-b]pyridazine 2-cyclopropyl-N'-(5-(4-(2-fluoro-6-methoxyphenyl)piperidin-1-yl)-4-(trifluoromethyl)pyridazin-3-yl)acetohydrazide A mixture of 5-(4-(2-fluoro-6-methoxyphenyl)piperidin-1-yl)-3-hydrazinyl-4-(trifluoromethyl)pyridazine (0.20 g, 0.519 mmol) in ethyl acetate (2.5 ml), THF (5 ml), and saturated sodium bicarbonate (5 ml) was stirred as 2-cyclopropylacetyl chloride (0.068 g, 0.571 mmol) was added. The mixture was stirred for 16 h. The reaction was diluted with ethyl acetate and water. The ethyl acetate layer was separated, washed with water, and concentrated to give 2-cyclopropyl-N'-(5-(4-(2-fluoro-6-methoxyphenyl)piperidin-1-yl)-4-(trifluoromethyl)pyridazin-3-yl)acetohydrazide as a semisolid. LCMS: Rt=0.86 min, (M+H)$^+$=468.2.

3-(Cyclopropylmethyl)-7-(4-(2-fluoro-6-methoxyphenyl)piperidin-1-yl)-8-(trifluoromethyl)-[1,2,4]triazolo[4,3-b]pyridazine A solution of 2-cyclopropyl-N'-(5-(4-(2-fluoro-6-methoxyphenyl)piperidin-1-yl)-4-(trifluoromethyl)pyridazin-3-yl)acetohydrazide (0.25 g, 0.535 mmol) and, triphenylphosphine (0.168 g, 0.642 mmol), and azidotrimethylsilane (0.142 ml, 1.07 mmol) in methylene chloride (4 ml) was stirred in a cool water bath as 40% DEAD in toluene (0.731 ml, 1.604 mmol) was added. Effervescence occurred. The reaction was stirred for 1 h. The solution was applied to a silica gel column and the product was eluted with 0-100% ethyl acetate/hexane. The product fractions were concentrated to give a yellow oil. The crude material was purified via preparative HPLC on a Waters XBridge C18, 19×200 mm column, using 10-95% acetonitrile:water containing 20-mM ammonium acetate as the eluent. The product fractions were concentrated to give 3-(cyclopropylmethyl)-7-(4-(2-fluoro-6-methoxyphenyl)piperidin-1-yl)-8-(trifluoromethyl)-[1,2,4]triazolo[4,3-b]pyridazine (0.9 g, 3.3%). $^1$H NMR (500 MHz, DMSO-d$_6$) δ 8.73 (br. s., 1H), 7.94 (br. s., 1H), 7.23 (d, J=7.3 Hz, 1H), 6.93-6.70 (m, 1H), 2.96 (d, J=5.8 Hz, 5H), 2.89 (br. s., 4H), 2.73 (br. s., 3H), 2.22 (d, J=11.9 Hz, 2H), 1.66 (d, J=11.9 Hz, 2H), 1.21 (d, J=17.4 Hz, 1H), 0.49 (br. s., 1H), 0.28 (br. s., 1H). LCMS: Rt=0.99 min, (M+H)$^+$=450.1.

Example 72

2-(1-(8-Chloro-3-(cyclopropylmethyl)-[1,2,4]triazolo[4,3-b]pyridazin-7-yl)piperidin-4-yl)benzonitrile 2-(1-(5-Chloro-6-hydrazinylpyridazin-4-yl)piperidin-4-yl)benzonitrile A mixture of 3,4,5-trichloropyridazine (0.50 g, 2.73 mmol), 2-(piperidin-4-yl)benzonitrile hydrochloride (0.607 g, 2.73 mmol), and potassium carbonate (0.791 g, 5.72 mmol) in dioxane (9.1 ml) and water (1 ml) was heated to reflux for 1 h. The mixture was cooled and 35% hydrazine (4.94 ml, 54.5 mmol) was added. The mixture was heated to reflux for 16 h. The reaction was diluted with ethyl acetate and water. The ethyl acetate layer was washed with water and concentrated to give 2-(1-(5-chloro-6-hydrazinylpyridazin-4-yl)piperidin-4-yl)benzonitrile as a brown oil. Rt=0.71 min, (M+H)$^+$=329.1. The material was used without purification.

N'-(4-chloro-5-(4-(2-cyanophenyl)piperidin-1-yl)pyridazin-3-yl)-2-cyclopropylacetohydrazide A mixture of 2-(1-(5-chloro-6-hydrazinylpyridazin-4-yl)piperidin-4-yl)benzonitrile (0.50 g, 1.521 mmol) in ethyl acetate (2.5 ml), THF (5 ml), and saturated sodium bicarbonate (5 ml) was stirred as 2-cyclopropylacetyl chloride (0.198 g, 1.673 mmol) was added. The mixture was stirred for 16 h. The reaction was diluted with ethyl acetate and saturated sodium bicarbonate. The ethyl acetate layer was separated, washed with water, and concentrated to give N'-(4-chloro-5-(4-(2-cyanophenyl)piperidin-1-yl)pyridazin-3-yl)-2-cyclopropylacetohydrazide as a semisolid. LCMS: Rt=0.79 min, (M+H)$^+$=411.1. The material was used without purification.

2-(1-(8-Chloro-3-(cyclopropylmethyl)-[1,2,4]triazolo[4,3-b]pyridazin-7-yl)piperidin-4-yl)benzonitrile A solution of N'-(4-chloro-5-(4-(2-cyanophenyl)piperidin-1-yl)pyridazin-3-yl)-2-cyclopropylacetohydrazide (0.60 g, 1.46 mmol) and phosphorus oxychloride (0.204 ml, 2.190 mmol) in acetonitrile (5 ml) was heated to 80° C. for 16 h. The reaction was diluted with ethyl acetate and saturated sodium bicarbonate. The ethyl acetate layer was washed with water and concentrated to a black oil. The oil was purified by preparative HPLC on a Waters XBridge C18, 19×200 mm column using 30-70% acetonitrile:water with 20-mM ammonium acetate as the eluent, to give 2-(1-(8-chloro-3-(cyclopropylmethyl)-[1,2,4]triazolo[4,3-b]pyridazin-7-yl)piperidin-4-yl)benzonitrile (47.8 mg, 8.3%). $^1$H NMR (500 MHz, DMSO-d$_6$) δ 8.67 (br. s., 1H), 7.83 (d, J=7.0 Hz, 1H), 7.71 (d, J=7.0 Hz, 1H), 7.62 (d, J=7.3 Hz, 1H), 7.45 (br. s., 1H), 3.76 (d, J=10.7 Hz, 3H), 3.16-2.91 (m, 4H), 1.94 (br. s., 4H), 1.21 (br. s., 1H), 0.50 (d, J=6.4 Hz, 2H), 0.29 (br. s., 2H). LCMS: Rt=0.96 min, (M+H)$^+$=393.1.

Example 73

2-(1-(8-chloro-3-(2,2,2-trifluoroethyl)-[1,2,4]triazolo[4,3-b]pyridazin-7-yl)piperidin-4-yl)benzonitrile N'-(4-chloro-5-(4-(2-cyanophenyl)piperidin-1-yl)pyridazin-3-yl)-3,3,3-trifluoropropanehydrazide A mixture of 2-(1-(5-chloro-6-hydrazinylpyridazin-4-yl)piperidin-4-yl)benzonitrile (0.50 g, 1.521 mmol) in ethyl acetate (2.5 ml), THF (5 ml), and saturated sodium bicarbonate (5 ml) was stirred as 3,3,3-trifluoropropanoyl chloride (0.172 ml, 1.673 mmol) was added. The mixture was stirred for 32 h. The reaction was diluted with ethyl acetate and water. The ethyl acetate layer was separated, washed with water, and concentrated to give N'-(4-chloro-5-(4-(2-cyanophenyl)piperidin-1-yl)pyridazin-3-yl)-3,3,3-trifluoropropanehydrazide as a semisolid. LCMS: Rt=0.82 min, (M+H)+=439.1. The material was used without purification.

2-(1-(8-chloro-3-(2,2,2-trifluoroethyl)-[1,2,4]triazolo [4,3-b]pyridazin-7-yl)piperidin-4-yl)benzonitrile A solution of N'-(4-chloro-5-(4-(2-cyanophenyl)piperidin-1-yl)pyridazin-3-yl)-3,3,3-trifluoropropanehydrazide (0.60 g, 1.367 mmol) and phosphorus oxychloride (0.191 ml, 2.051 mmol) in acetonitrile (5 ml) was heated to 80° C. for 16 h. The reaction was diluted with ethyl acetate and saturated sodium bicarbonate. The ethyl acetate layer was washed with water and concentrated to a black oil. The oil was purified by preparative HPLC on a Waters XBridge C18, 19×200 mm column using 30-70% acetonitrile:water with 20-mM ammonium acetate as the eluent, to give 2-(1-(8-chloro-3-(2,2,2-trifluoroethyl)-[1,2,4]triazolo[4,3-b]pyridazin-7-yl)piperidin-4-yl)benzonitrile (23.4 mg, 4%). $^1$H NMR (500 MHz, DMSO-$d_6$) δ 8.76 (s, 1H), 7.83 (d, J=7.6 Hz, 1H), 7.71 (d, J=6.4 Hz, 2H), 7.45 (t, J=7.0 Hz, 1H), 4.34 (d, J=10.4 Hz, 2H), 3.82 (d, J=11.9 Hz, 2H), 3.26 (br. s., 5H), 3.12 (br. s., 2H), 1.94 (br. s., 5H). LCMS: Rt=0.98 min, (M+H)+=421.0.

Example 74

8-Chloro-3-(cyclopropylmethyl)-7-(4-(2,4-difluorophenyl)piperidin-1-yl)-[1,2,4]triazolo[4,3-b]pyridazine 4-Chloro-5-(4-(2,4-difluorophenyl)piperidin-1-yl)-3-hydrazinylpyridazine A mixture of 3,4,5-trichloropyridazine (0.50 g, 2.73 mmol), 4-(2,4-difluorophenyl)piperidine (0.538 g, 2.73 mmol), and potassium carbonate (0.791 g, 5.72 mmol) in dioxane (9 ml) and water (1 ml) was heated to reflux for 1 h. The mixture was cooled and 35% hydrazine (4.94 ml, 54.5 mmol) was added. The mixture was heated to reflux for 16 h. The reaction was diluted with ethyl acetate and water. The ethyl acetate layer was washed with water and concentrated to give 4-chloro-5-(4-(2,4-difluorophenyl)piperidin-1-yl)-3-hydrazinylpyridazine as a brown oil. LCMS: Rt=0.74 min, (M+H)+=340.0. The material was used without purification.

N'-(4-Chloro-5-(4-(2,4-difluorophenyl)piperidin-1-yl)pyridazin-3-yl)-2-cyclopropylacetohydrazide A solution of 4-chloro-5-(4-(2,4-difluorophenyl)piperidin-1-yl)-3-hydrazinylpyridazine (0.50 g, 1.472 mmol) in ethyl acetate (2.5 ml), THF (5 ml), and saturated sodium bicarbonate (5 ml) was stirred as 2-cyclopropylacetyl chloride (0.192 g, 1.619 mmol) was added. The mixture was stirred for 16 h. The reaction was diluted with ethyl acetate and water. The ethyl acetate layer was separated, washed with water, and concentrated to give N'-(4-chloro-5-(4-(2,4-difluorophenyl)piperidin-1-yl)pyridazin-3-yl)-2-cyclopropylacetohydrazide as a semisolid. LCMS: Rt=0.83 min, (M+H)+=422.10.

8-Chloro-3-(cyclopropylmethyl)-7-(4-(2,4-difluorophenyl)piperidin-1-yl)-[1,2,4]triazolo[4,3-b]pyridazine A solution of N'-(4-chloro-5-(4-(2,4-difluorophenyl)piperidin-1-yl)pyridazin-3-yl)-2-cyclopropylacetohydrazide (0.60 g, 1.42 mmol) and phosphorus oxychloride (0.20 ml, 2.1 mmol) in acetonitrile (5 ml) was heated to 80° C. for 16 h. The reaction was diluted with ethyl acetate and saturated sodium bicarbonate. The ethyl acetate layer was washed with water and concentrated to a black oil. The oil was purified by preparative HPLC on a Waters XBridge C18, 19×200 mm column using 35-75% acetonitrile:water with 20-mM ammonium acetate as the eluent, to give 8-chloro-3-(cyclopropylmethyl)-7-(4-(2,4-difluorophenyl)piperidin-1-yl)-[1,2,4]triazolo[4,3-b]pyridazine (38.7 mg, 6.7%). $^1$H NMR (500 MHz, DMSO-$d_6$) δ 8.64 (s, 1H), 7.45 (d, J=7.3 Hz, 1H), 7.20 (br. s., 1H), 7.06 (br. s., 1H), 3.72 (d, J=11.3 Hz, 2H), 3.25-3.12 (m, 2H), 3.00 (d, J=6.7 Hz, 3H), 1.86 (br. s., 4H), 1.20 (br. s., 1H), 0.49 (d, J=6.1 Hz, 2H), 0.28 (d, J=4.3 Hz, 2H). LCMS: Rt=1.02 min, (M+H)+=404.0.

Example 75

8-Chloro-7-(4-(2,4-difluorophenyl)piperidin-1-yl)-3-(2,2,2-trifluoroethyl)-[1,2,4]triazolo[4,3-b]pyridazine 4-Chloro-3-hydrazinyl-5-(4-(3-(trifluoromethyl)pyridin-2-yl)piperidin-1-yl)pyridazine A mixture of 3,4,5-trichloropyridazine (0.446 g, 2.432 mmol), 2-(piperidin-4-yl)-3-(trifluoromethyl)pyridine (0.56 g, 2.432 mmol), and potassium carbonate (0.706 g, 5.11 mmol) in dioxane (8 ml) was heated to reflux for 1 h. The mixture was cooled and 35% hydrazine (4.41 ml, 48.6 mmol) was added. The mixture was heated to reflux for 16 h. The reaction was diluted with ethyl acetate and water. The ethyl acetate layer was washed with water and concentrated to give 4-chloro-3-hydrazinyl-5-(4-(3-(trifluoromethyl)pyridin-2-yl)piperidin-1-yl)pyridazine as a brown oil. LCMS: Rt=0.76 min, (M+H)+=373.7. The material was used without purification.

N'-(4-Chloro-5-(4-(2,4-difluorophenyl)piperidin-1-yl)pyridazin-3-yl)-3,3,3-trifluoropropanehydrazide A mixture of 4-chloro-5-(4-(2,4-difluorophenyl)piperidin-1-yl)-3-hydrazinylpyridazine (0.50 g, 1.47 mmol) in ethyl acetate (2.5 ml), THF (5 ml), and saturated sodium bicarbonate (5 ml) was stirred as 3,3,3-trifluoropropanoyl chloride (0.167 ml, 1.619 mmol) was added. The mixture was stirred for 32 h. The reaction was diluted with ethyl acetate and water. The ethyl acetate layer was separated, washed with water, and concentrated to give N'-(4-chloro-5-(4-(2,4-difluorophenyl)piperidin-1-yl)pyridazin-3-yl)-3,3,3-trifluoropropanehydrazide as a brown oil. LMCS: Rt=0.87 min, (M+H)+=450.0. The material was used without purification.

8-Chloro-7-(4-(2,4-difluorophenyl)piperidin-1-yl)-3-(2,2,2-trifluoroethyl)-[1,2,4]triazolo[4,3-b]pyridazine A solution of N'-(4-chloro-5-(4-(2,4-difluorophenyl)piperidin-1-yl)pyridazin-3-yl)-3,3,3-trifluoropropanehydrazide (0.60 g, 1.33 mmol) and phosphorus oxychloride (0.187 ml, 2.001 mmol) in acetonitrile was heated to 80° C. for 16 h. The reaction was diluted with ethyl acetate and saturated sodium bicarbonate. The ethyl acetate layer was washed with water and concentrated to a black oil. The oil was purified by preparative HPLC on a Waters XBridge C18, 19×200 mm column using 35-75% acetonitrile:water with 20-mM ammonium acetate as the eluent, to give 8-chloro-7-(4-(2,4-difluorophenyl)piperidin-1-yl)-3-(2,2,2-trifluoroethyl)-[1,2,4]triazolo[4,3-b]pyridazine (30.8 mg, 5.4%). $^1$H NMR (500 MHz, DMSO-d$_6$) δ 8.72 (br. s., 1H), 7.44 (d, J=6.4 Hz, 1H), 7.19 (br. s., 1H), 7.06 (br. s., 1H), 4.32 (d, J=10.7 Hz, 2H), 3.78 (d, J=10.7 Hz, 3H), 3.02 (br. s., 2H), 1.87 (br. s., 4H). LCMS: Rt=1.05 min, (M+H)$^+$=432.0.

Example 76

8-Chloro-3-(cyclopropylmethyl)-7-(4-(3-(trifluoromethyl)pyridin-2-yl)piperidin-1-yl)-[1,2,4]triazolo[4,3-b]pyridazine tert-Butyl 3-(trifluoromethyl)-5',6'-dihydro-[2,4'-bipyridine]-1'(2'H)-carboxylate A mixture of tert-butyl 4-(4,4,5,5-tetramethyl-1,3,2-dioxaborolan-2-yl)-5,6-dihydropyridine-1(2H)-carboxylate (0.75 g, 2.42 mmol), 2-chloro-3-(trifluoromethyl)pyridine (0.66 g, 3.64 mmol), tetrakis(triphenylphosphine)palladium (0) (0.076 g, 0.065 mmol), and potassium carbonate (0.67 g, 4.85 mmol) in dioxane (15 ml) and water (1.5 ml) was heated to 100° C. for 4 h. The residue was diluted with ethyl acetate and washed with saturated sodium bicarbonate. The organic layers were dried over magnesium sulfate, and concentrated to give tert-Butyl 3-(trifluoromethyl)-5',6'-dihydro-[2,4'-bipyridine]-1'(2'H)-carboxylate as a yellow solid. LCMS: Rt=1.03 min, (M+H)$^+$=273.6. The material was used without purification.

tert-Butyl 4-(3-(trifluoromethyl)pyridin-2-yl)piperidine-1-carboxylate

A mixture of tert-butyl 3-(trifluoromethyl)-5',6'-dihydro-[2,4'-bipyridine]-1'(2'H)-carboxylate (0.80 g, 2.44 mmol), Pearlman's Catalyst (0.342 g), and ammonium formate (1.075 g, 17.06 mmol) in ethanol (46 ml) and water (1.4 ml) was stirred at 80° C. for 48 h. The reaction was filtered through celite and the filtrate was concentrated to give tert-butyl 4-(3-(trifluoromethyl)pyridin-2-yl)piperidine-1-carboxylate as a clear oil. LCMS: Rt=1.11 min, (M+H)$^+$=275.5.

2-(Piperidin-4-yl)-3-(trifluoromethyl)pyridine

A solution of tert-butyl 4-(3-(trifluoromethyl)pyridin-2-yl)piperidine-1-carboxylate (0.80 g, 2.42 mmol) in dichloromethane (25 ml) and TFA (9.33 ml, 121 mmol) was stirred for 2 h. The reaction was concentrated to give 2-(piperidin-4-yl)-3-(trifluoromethyl)pyridine as a light yellow oil. LCMS: Rt=0.59 min, (M+H)$^+$=231.5.

4-Chloro-3-hydrazinyl-5-(4-(3-(trifluoromethyl)pyridin-2-yl)piperidin-1-yl)pyridazine A mixture of 3,4,5-trichloropyridazine (0.446 g, 2.432 mmol), 2-(piperidin-4-yl)-3-(trifluoromethyl)pyridine (0.560 g, 2.432 mmol), and potassium carbonate (0.706 g, 5.11 mmol) in dioxane (8 ml) was heated to reflux for 1 h. The mixture was cooled and 35% hydrazine (4.41 ml, 48.6 mmol) was added. The mixture was heated to reflux for 16 h. The reaction was diluted with ethyl acetate and water. The organic layers were washed with water and concentrated to give 4-chloro-3-hydrazinyl-5-(4-(3-(trifluoromethyl)pyridin-2-yl)piperidin-1-yl)pyridazine as a brown oil. LCMS: Rt=0.74 min, (M+H)$^+$=373.7.

N'-(4-Chloro-5-(4-(3-(trifluoromethyl)pyridin-2-yl)piperidin-1-yl)pyridazin-3-yl)-2-cyclopropylacetohydrazide A mixture of 4-chloro-3-hydrazinyl-5-(4-(3-(trifluoromethyl)pyridin-2-yl)piperidin-1-yl)pyridazine (0.907 g, 2.433 mmol), in ethyl acetate (2.5 ml), THF (5 ml), and saturated sodium bicarbonate (5 ml) was stirred as 2-cyclopropylacetyl chloride (0.317 g, 2.68 mmol) was added. The mixture was stirred for 16 h. The reaction was diluted with ethyl acetate and water. The ethyl acetate layer was separated, washed with water, and concentrated to give N'-(4-chloro-5-(4-(3-(trifluoromethyl)pyridin-2-yl)piperidin-1-yl)pyridazin-3-yl)-2-cyclopropylacetohydrazide as a brown oil. LCMS: Rt=0.78 min, (M+H)$^+$=455.8. The material was used without purification.

8-Chloro-3-(cyclopropylmethyl)-7-(4-(3-(trifluoromethyl)pyridin-2-yl)piperidin-1-yl)-[1,2,4]triazolo[4,3-b]pyridazine A solution of N'-(4-chloro-5-(4-(3-(trifluoromethyl)pyridin-2-yl)piperidin-1-yl)pyridazin-3-yl)-2-cyclopropylacetohydrazide (1.1 g, 2.418 mmol) and phosphorus oxychloride (0.34 ml, 3.63 mmol) in acetonitrile (5 ml) was heated to 80° C. for 16 h. The reaction was diluted with ethyl acetate and saturated sodium bicarbonate. The ethyl acetate layer was washed with water and concentrated to a black oil. The oil was purified by preparative HPLC on a XBridge OBD 19×100 mm column using 35-95% acetonitrile:water with 20-mM ammonium acetate as the eluent, to give 8-chloro-3-(cyclopropylmethyl)-7-(4-(3-(trifluoromethyl)pyridin-2-yl)piperidin-1-yl)-[1,2,4]triazolo[4,3-b]pyridazine (74.3 mg, 6.7%). $^1$H NMR (400 MHz, METHANOL-d$_4$) δ 8.79 (d, J=4.8 Hz, 1H), 8.60 (s, 1H), 8.10 (dd, J=8.0, 1.0 Hz, 1H), 7.44 (dd, J=7.7, 5.1 Hz, 1H), 3.94 (d, J=12.3 Hz, 2H), 3.27 (d, J=2.3 Hz, 3H), 3.08 (d, J=7.0 Hz, 2H), 2.33 (qd, J=12.5, 4.0 Hz, 2H), 1.91 (d, J=12.8 Hz, 2H), 1.38-1.19 (m, 1H), 0.66-0.52 (m, 2H), 0.44-0.26 (m, 2H). LMCS: Rt=0.96 min, (M+H)$^+$=437.7.

Example 77

2-(1-(3-(Cyclopropylmethyl)-8-(trifluoromethyl)-[1,2,4]triazolo[4,3-b]pyridazin-7-yl)piperidin-4-yl)benzonitrile 2-(1-(5-Bromo-6-oxo-1,6-dihydropyridazin-4-yl)piperidin-4-yl)benzonitrile A solution of 4,5-dibromopyridazin-3(2H)-one (0.30 g, 1.182 mmol), 2-(piperidin-4-yl)benzonitrile hydrochloride (0.289 g, 1.300 mmol), and DIPEA (0.454 ml, 2.60 mmol) in DMA (2.498 ml) was heated to 100° C. for 16 h. The reaction was cooled and diluted with saturated sodium bicarbonate to give a tan precipitate that was filtered and dried to give 2-(1-(5-bromo-6-oxo-1,6-dihydropyridazin-4-yl)piperidin-4-yl)benzonitrile (0.434 g, 100%). LCMS: Rt=0.85 min, (M+H)$^+$=359.7. The material was used without purification.

tert-Butyl 5-bromo-4-(4-(2-cyanophenyl)piperidin-1-yl)-6-oxopyridazine-1(6H)-carboxylate A solution of 2-(1-(5-bromo-6-oxo-1,6-dihydropyridazin-4-yl)piperidin-4-yl)benzonitrile (0.435 g, 1.211 mmol), di-tert-butyl dicarbonate (0.337 ml, 1.453 mmol), and triethyl amine (0.253 ml, 1.816 mmol) in methylene chloride (50 ml) was stirred for 32 h. The reaction was washed with water. The organic layers dried over magnesium sulfate and concentrated to give tert-butyl 5-bromo-4-(4-(2-cyanophenyl) piperidin-1-yl)-6-oxopyridazine-1(6H)-carboxylate a brown oil. LCMS: Rt=1.04 min, (M+H)$^+$=361.6.

2-(1-(6-Oxo-5-(trifluoromethyl)-1,6-dihydro-pyridazin-4-yl)piperidin-4-yl)benzonitrile A mixture of tert-butyl 5-bromo-4-(4-(2-cyanophenyl) piperidin-1-yl)-6-oxopyridazine-1(6H)-carboxylate (0.55 g, 1.197 mmol) in DMF (11 ml) was added copper(I) iodide (0.456 g, 2.395 mmol) was stirred as methyl 2,2-difluoro-2-(fluorosulfonyl)acetate (0.303 ml, 2.395 mmol) was added. The mixture was heated to 100° C. for 1 h. The reaction was filtered through a pad of silica gel, and the pad was rinsed with ethyl acetate. The filtrate was washed with saturated sodium bicarbonate and ammonium chloride. The organic layer concentrated to give 2-(1-(6-oxo-5-(trifluoromethyl)-1,6-dihydropyridazin-4-yl)piperidin-4-yl)benzonitrile (0.437 g, 100%) a brown oil. LCMS: Rt=0.88 min, (M+H)$^+$=349.7. The material was used without purification.

tert-Butyl 4-(4-(2-cyanophenyl)piperidin-1-yl)-6-oxo-5-(trifluoromethyl)pyridazine-1(6H)-carboxylate A solution of 2-(1-(6-oxo-5-(trifluoromethyl)-1,6-dihydropyridazin-4-yl)piperidin-4-yl)benzonitrile (0.437 g, 1.255 mmol), di-tert-butyl dicarbonate (0.35 ml, 1.50 mmol), and triethyl amine (0.262 ml, 1.882 mmol) in methylene chloride (50 ml) was stirred at 40° C. for 2 h. The reaction was washed with water and the methylene chloride layer was dried over magnesium sulfate, and concentrated to a brown oil. The material was used without purification.

2-(1-(6-Chloro-5-(trifluoromethyl)pyridazin-4-yl) piperidin-4-yl)benzonitrile

A solution of tert-butyl 4-(4-(2-cyanophenyl)piperidin-1-yl)-6-oxo-5-(trifluoromethyl)pyridazine-1(6H)-carboxylate (0.779 g, 1.737 mmol) and phosphorus oxychloride (5.34 ml, 57.3 mmol) in acetonitrile (5 ml) was heated to 100° C. for 1 h. The reaction was concentrated and the residue was dissolved in methylene chloride and saturated sodium bicarbonate. The methylene chloride layer was separated, dried over magnesium sulfate, and concentrated to give 2-(1-(6-chloro-5-(trifluoromethyl)pyridazin-4-yl)piperidin-4-yl) benzonitrile as a brown oil. LCMS: Rt=1.01 min, (M+H)$^+$=367.7.

2-(1-(6-Hydrazinyl-5-(trifluoromethyl)pyridazin-4-yl)piperidin-4-yl)benzonitrile A mixture of 2-(1-(6-chloro-5-(trifluoromethyl)pyridazin-4-yl)piperidin-4-yl)benzonitrile (0.637 g, 1.737 mmol), potassium carbonate (0.504 g, 3.65 mmol), and 35% hydrazine (3.15 ml, 34.7 mmol) in dioxane (10 ml) was heated to 100° C. for 2 h. The mixture was cooled, diluted with water, and extracted with ethyl acetate. The ethyl acetate layer was concentrated to give 2-(1-(6-hydrazinyl-5-(trifluoromethyl) pyridazin-4-yl)piperidin-4-yl)benzonitrile as a brown oil. LCMS: Rt=0.74 min, (M+H)$^+$=363.7. The material was used without purification.

N'-(5-(4-(2-Cyanophenyl)piperidin-1-yl)-4-(trifluoromethyl)pyridazin-3-yl)-2-cyclopropylacetohydrazide A mixture of 2-(1-(6-hydrazinyl-5-(trifluoromethyl) pyridazin-4-yl)piperidin-4-yl)benzonitrile (0.318 g, 0.878 mmol) in ethyl acetate (2.5 ml), THF (5 ml), and saturated sodium bicarbonate (5 ml) was stirred as 2-cyclopropylacetyl chloride (0.114 g, 0.965 mmol) was added. The mixture was stirred for 16 h. The reaction was diluted with ethyl acetate and saturated sodium bicarbonate. The ethyl acetate layer was separated, washed with water, and concentrated to give N'-(5-(4-(2-cyanophenyl)piperidin-1-yl)-4-(trifluoromethyl)pyridazin-3-yl)-2-cyclopropylacetohydrazide as a brown oil. LCMS: Rt=0.81 min, (M+H)$^+$=445.8. The material was used without purification.

2-(1-(3-(Cyclopropylmethyl)-8-(trifluoromethyl)-[1,2,4]triazolo[4,3-b]pyridazin-7-yl)piperidin-4-yl)benzonitrile A solution of N'-(5-(4-(2-cyanophenyl)piperidin-1-yl)-4-(trifluoromethyl)pyridazin-3-yl)-2-cyclopropylacetohydrazide (0.390 g, 0.877 mmol) and phosphorus oxychloride (0.123 ml, 1.316 mmol) in acetonitrile (5 ml) was heated to 80° C. for 16 h. The reaction was cooled and diluted with saturated sodium bicarbonate and ethyl acetate. The ethyl acetate layer was concentrated give a black oil. The oil was purified by preparative HPLC on a XBridge OBD 19×100 mm column using 30-95% acetonitrile:water with 20-mM ammonium acetate as the eluent, to give 2-(1-(3-(cyclopropylmethyl)-8-(trifluoromethyl)-[1,2,4]triazolo[4,3-b] pyridazin-7-yl)piperidin-4-yl)benzonitrile (20.4 mg, 5.2%). $^1$H NMR (400 MHz, METHANOL-d$_4$) δ 8.70 (s, 1H), 7.82-7.49 (m, 3H), 7.49-7.35 (m, 1H), 3.88 (br. s., 2H), 3.60-3.41 (m, 2H), 3.32-3.19 (m, 1H), 3.05 (d, J=7.0 Hz, 2H), 1.97-1.86 (m, 4H), 1.39-1.18 (m, 1H), 0.58 (dd, J=8.0, 1.5 Hz, 2H), 0.43-0.29 (m, 2H). Rt=2.10 min, (M+H)$^+$=427.2.

Example 78

2-(1-(3-(2,2,2-Trifluoroethyl)-8-(trifluoromethyl)-[1,2,4]triazolo[4,3-b]pyridazin-7-yl)piperidin-4-yl)benzonitrile N'-(5-(4-(2-Cyanophenyl)piperidin-1-yl)-4-(trifluoromethyl)pyridazin-3-yl)-3,3,3-trifluoropropanehydrazide A mixture of 2-(1-(6-hydrazinyl-5-(trifluoromethyl) pyridazin-4-yl)piperidin-4-yl)benzonitrile (0.318 g, 0.878 mmol), ethyl acetate (2.5 ml), THF (5 ml), and saturated sodium bicarbonate (5 ml) was stirred as 3,3,3-trifluoropropanoyl chloride (0.10 ml, 0.965 mmol) was added. The mixture was stirred for 16 h. The reaction was diluted with ethyl acetate and saturated sodium bicarbonate. The ethyl acetate layer was separated, washed with water, and concentrated to give N'-(5-(4-(2-cyanophenyl)piperidin-1-yl)-4-(trifluoromethyl)pyridazin-3-yl)-3,3,3-trifluoropropanehydrazide as a brown oil. LCMS: Rt=0.83 min, (M+H)$^+$=473.8.

2-(1-(3-(2,2,2-Trifluoroethyl)-8-(trifluoromethyl)-[1,2,4]triazolo[4,3-b]pyridazin-7-yl)piperidin-4-yl)benzonitrile A solution of N'-(5-(4-(2-cyanophenyl)piperidin-1-yl)-4-(trifluoromethyl)pyridazin-3-yl)-3,3,3-trifluoropropanehydrazide (0.415 g, 0.879 mmol) and phosphorus oxychloride (0.123 ml, 1.318 mmol) in acetonitrile (5 ml) was heated to 80° C. for 16 h. The reaction was cooled and diluted with saturated sodium bicarbonate and ethyl acetate. The ethyl acetate layer was concentrated give a black oil. The oil was purified by preparative HPLC on a XBridge OBD 19×100 mm column using 40-90% acetonitrile:water containing 20-mM ammonium acetate as the eluent, to give 2-(1-(3-(2,2,2-trifluoroethyl)-8-(trifluoromethyl)-[1,2,4]triazolo[4,3-b]pyridazin-7-yl)piperidin-4-yl)benzonitrile (27.8 mg, 6.9%). $^1$H NMR (400 MHz, METHANOL-$d_4$) δ 8.78 (s, 1H), 7.81-7.63 (m, 2H), 7.56 (d, J=8.0 Hz, 1H), 7.42 (td, J=7.6, 1.1 Hz, 1H), 4.20 (q, J=10.0 Hz, 2H), 3.93 (d, J=13.1 Hz, 2H), 3.54 (t, J=13.7 Hz, 2H), 2.09-1.99 (m, 3H), 1.97-1.82 (m, 2H). LCMS: Rt=2.06 min, (M+H)$^+$=455.2.

Example 79

8-Chloro-3-(cyclopropylmethyl)-7-(4-(pyridin-2-yl)piperidin-1-yl)-[1,2,4]triazolo[4,3-b]pyridazine 4-Chloro-3-hydrazinyl-5-(4-(pyridin-2-yl)piperidin-1-yl)pyridazine A mixture of 3,4,5-trichloropyridazine (0.565 g, 3.08 mmol), 2-(piperidin-4-yl)pyridine (0.50 g, 3.08 mmol), and potassium carbonate (0.894 g, 6.47 mmol) in dioxane (10 ml) and water (1 ml). The reaction was heated to reflux for 1 h. The mixture was cooled and 35% hydrazine (5.58 ml, 61.6 mmol) was added. The mixture was heated to reflux for 16 h. The reaction was diluted with ethyl acetate and water. The ethyl acetate layer was washed with water and concentrated to give 3,4-dichloro-5-(4-(3-(trifluoromethyl)pyridin-2-yl)piperidin-1-yl)pyridazine as a brown oil. LCMS: Rt=0.62 min, (M+H)$^+$=308.9. The material was used without purification.

N'-(4-Chloro-5-(4-(pyridin-2-yl)piperidin-1-yl)pyridazin-3-yl)-2-cyclopropylacetohydrazide A mixture of 4-chloro-3-hydrazinyl-5-(4-(pyridin-2-yl)piperidin-1-yl)pyridazine (0.94 g, 3.08 mmol), ethyl acetate (2.5 ml), THF (5 ml), and saturated sodium bicarbonate (5.00 ml) was stirred as 2-cyclopropylacetyl chloride (0.402 g, 3.39 mmol) was added. The mixture was stirred for 16 h. The reaction was diluted with ethyl acetate and saturated sodium bicarbonate. The ethyl acetate layer was separated, washed with water, and concentrated to give N'-(4-chloro-5-(4-(pyridin-2-yl)piperidin-1-yl)pyridazin-3-yl)-2-cyclopropylacetohydrazide as a brown oil. LCMS: Rt=0.50 min, (M+H)$^+$=387.0. The material was used without purification.

8-Chloro-3-(cyclopropylmethyl)-7-(4-(pyridin-2-yl)piperidin-1-yl)-[1,2,4]triazolo[4,3-b]pyridazine A solution of N'-(4-chloro-5-(4-(pyridin-2-yl)piperidin-1-yl)pyridazin-3-yl)-2-cyclopropylacetohydrazide (1.2 g, 3.10 mmol) and phosphorus oxychloride (0.434 ml, 4.65 mmol) in acetonitrile (5 ml) was heated to 80° C. for 16 h. The reaction was cooled and diluted with saturated sodium bicarbonate and ethyl acetate. The ethyl acetate layer was concentrated give a brown oil. The oil was purified by preparative HPLC on a XBridge OBD 19×100 mm column using 10-90% acetonitrile:water with 20-mM ammonium acetate as the eluent, to give 8-chloro-3-(cyclopropylmethyl)-7-(4-(pyridin-2-yl)piperidin-1-yl)-[1,2,4]triazolo[4,3-b]pyridazine (6.3 mg, 0.5%) as a yellow oil. $^1$H NMR (400 MHz, METHANOL-$d_4$) δ 8.57 (s, 1H), 8.49 (dd, J=5.0, 0.8 Hz, 1H), 7.82 (td, J=7.8, 1.8 Hz, 1H), 7.42 (d, J=8.0 Hz, 1H), 7.29 (ddd, J=7.5, 5.0, 1.0 Hz, 1H), 3.91 (d, J=12.8 Hz, 2H), 3.39-3.23 (m, 4H), 3.04-2.89 (m, 1H), 2.14-2.03 (m, 5H), 0.67-0.48 (m, 2H), 0.44-0.25 (m, 2H). LCMS: Rt=0.63 min, (M+H)$^+$=369.0.

Example 80

3-(Cyclopropylmethyl)-7-(4-(3,6-difluoro-2-methoxyphenyl)piperidin-1-yl)-8-(trifluoromethyl)-[1,2,4]triazolo[4,3-b]pyridazine tert-Butyl 4-(4-(3,6-difluoro-2-methoxyphenyl)piperidin-1-yl)-6-oxo-5-(trifluoromethyl)pyridazine-1(6H)-carboxylate A solution of tert-butyl 5-bromo-4-(4-(3,6-difluoro-2-methoxyphenyl)piperidin-1-yl)-6-oxopyridazine-1(6H)-carboxylate (1.0 g, 2 mmol) copper(I) iodide (0.761 g, 4 mmol) in DMF (18 ml) was stirred as methyl 2,2-difluoro-2-(fluorosulfonyl)acetate (0.505 ml, 4 mmol) was added. The reaction was heated to 100° C. for 2 h. The reaction was filtered through a pad of silica gel, and the pad was rinsed with ethyl acetate. The filtrate was washed with saturated sodium bicarbonate and ammonium chloride. The ethyl acetate layer was concentrated to give tert-butyl 4-(4-(3,6-difluoro-2-methoxyphenyl)piperidin-1-yl)-6-oxo-5-(trifluoromethyl)pyridazine-1(6H)-carboxylate as a brown oil. LCMS: Rt=0.96 min. (M+H)$^+$=390.0. A solution of the oil, di-tert-butyl dicarbonate (0.564 ml, 2.429 mmol), amd triethyl amine (0.423 ml, 3.04 mmol) in methylene chloride (50 ml) was stirred for 24 h. The reaction was washed with water, dried over magnesium sulfate, and concentrated to give tert-butyl 4-(4-(3,6-difluoro-2-methoxyphenyl)piperidin-1-yl)-6-oxo-5-(trifluoromethyl)pyridazine-1(6H)-carboxylate as a brown oil. LCMS: Rt=1.11 min, (M+H)$^+$=390.0. The material was used without purification.

3-Chloro-5-(4-(3,6-difluoro-2-methoxyphenyl)piperidin-1-yl)-4-(trifluoromethyl)pyridazine A solution of tert-butyl 4-(4-(3,6-difluoro-2-methoxyphenyl)piperidin-1-yl)-6-oxo-5-(trifluoromethyl)pyridazine-1(6H)-carboxylate (1.0 g, 2.04 mmol) and phosphorus oxychloride (6.28 ml, 67.4 mmol) was heated to 100° C. for 3 h. The mixture was concentrated. The residue was dissolved in methylene chloride, washed with saturated sodium bicarbonate, dried over magnesium sulfate, and concentrated to give 3-chloro-5-(4-(3,6-difluoro-2-methoxyphenyl)piperidin-1-yl)-4-(trifluoromethyl)pyridazine as a brown oil. LCMS: Rt=1.09 min, (M+H)$^+$=407.9. The material was used without purification.

5-(4-(3,6-Difluoro-2-methoxyphenyl)piperidin-1-yl)-3-hydrazinyl-4-(trifluoromethyl)pyridazine A mixture of 3-chloro-5-(4-(3,6-difluoro-2-methoxyphenyl)piperidin-1-yl)-4-(trifluoromethyl)pyridazine (0.833, 2.04 mmol), potassium carbonate (0.593 g, 4.29 mmol), and 35% hydrazine (3.70 ml, 40.9 mmol) in dioxane (10 ml) heated to 100° C. for 4 h. The reaction was diluted with ethyl acetate and water. The ethyl acetate layer was washed with water and concentrated to give 5-(4-(3,6-difluoro-2-methoxyphenyl)piperidin-1-yl)-3-hydrazinyl-4-(trifluoromethyl)pyridazine as a brown oil. LCMS: Rt=0.81 min, (M+H)+=404.0. The material was used without purification.

2-Cyclopropyl-N'-(5-(4-(3,6-difluoro-2-methoxyphenyl)piperidin-1-yl)-4-(trifluoromethyl)pyridazin-3-yl)acetohydrazide A mixture of 5-(4-(3,6-difluoro-2-methoxyphenyl)piperidin-1-yl)-3-hydrazinyl-4-(trifluoromethyl)pyridazine (0.40 g, 0.992 mmol), ethyl acetate (2.5 ml), THF (5 ml), and saturated sodium bicarbonate (5 ml) was stirred as 2-cyclopropylacetyl chloride (0.129 g, 1.091 mmol) was added. The mixture was stirred for 16 h. The reaction was diluted with ethyl acetate and saturated sodium bicarbonate. The ethyl acetate layer was separated, washed with water, and concentrated to give 2-cyclopropyl-N'-(5-(4-(3,6-difluoro-2-methoxyphenyl)piperidin-1-yl)-4-(trifluoromethyl)pyridazin-3-yl)acetohydrazide as a brown oil. LCMS: Rt=0.54 min, (M+H)+=388.0. The material was used without purification.

3-(Cyclopropylmethyl)-7-(4-(3,6-difluoro-2-methoxyphenyl)piperidin-1-yl)-8-(trifluoromethyl)-[1,2,4]triazolo[4,3-b]pyridazine A solution of 2-cyclopropyl-N'-(5-(4-(3,6-difluoro-2-methoxyphenyl)piperidin-1-yl)-4-(trifluoromethyl)pyridazin-3-yl)acetohydrazide (0.48 g, 0.989 mmol) and phosphorus oxychloride (0.138 ml, 1.483 mmol) in acetonitrile (5 ml) was heated to 80° C. for 16 h. The reaction was cooled and diluted with saturated sodium bicarbonate and ethyl acetate. The ethyl acetate layer was concentrated give a brown oil. The oil was purified by preparative HPLC on a XBridge OBD 19×100 mm column using 30-90% acetonitrile:water containing 20-mM ammonium acetate as the eluent. The product fractions were concentrated to an oil. The oil was dissolved in ethyl acetate, washed with saturated sodium bicarbonate, dried over magnesium sulfate, and concentrated to give 3-(cyclopropylmethyl)-7-(4-(3,6-difluoro-2-methoxyphenyl)piperidin-1-yl)-8-(trifluoromethyl)-[1,2,4]triazolo[4,3-b]pyridazine (11.3 mg, 2.3%) as a yellow oil. $^1$H NMR (400 MHz, METHANOL-d$_4$) δ 8.68 (s, 1H), 7.04 (ddd, J=10.9, 9.2, 5.0 Hz, 1H), 6.82 (ddd, J=10.3, 9.3, 4.0 Hz, 1H), 3.94 (d, J=1.8 Hz, 3H), 3.85 (d, J=13.1 Hz, 2H), 3.52-3.35 (m, 3H), 3.05 (d, J=7.0 Hz, 2H), 2.37 (dd, J=12.5, 3.3 Hz, 2H), 1.80 (dd, J=13.1, 2.8 Hz, 2H), 1.36-1.21 (m, 1H), 0.67-0.53 (m, 2H), 0.42-0.27 (m, 2H). LCMS: Rt=1.00 min, (M+H)+=468.0.

Example 81

7-(4-(3,6-Difluoro-2-methoxyphenyl)piperidin-1-yl)-3-(2,2,2-trifluoroethyl)-8-(trifluoromethyl)-[1,2,4]triazolo[4,3-b]pyridazine N'-(5-(4-(3,6-Difluoro-2-methoxyphenyl)piperidin-1-yl)-4-(trifluoromethyl)pyridazin-3-yl)-3,3,3-trifluoropropanehydrazide A mixture of 5-(4-(3,6-difluoro-2-methoxyphenyl)piperidin-1-yl)-3-hydrazinyl-4-(trifluoromethyl)pyridazine (0.40 g, 0.992 mmol), ethyl acetate (2.5 ml), THF (5 ml), and saturated sodium bicarbonate (5 ml) was stirred as 3,3,3-trifluoropropanoyl chloride (0.112 ml, 1.091 mmol) was added. The mixture stirred for 16 h. The reaction was diluted with ethyl acetate and saturated sodium bicarbonate. The ethyl acetate layer was separated, washed with water, and concentrated to give N'-(5-(4-(3,6-difluoro-2-methoxyphenyl)piperidin-1-yl)-4-(trifluoromethyl)pyridazin-3-yl)-3,3,3-trifluoropropanehydrazide as a brown oil. LCMS: Rt=0.59 min, (M+H)+=415.9. The material was used without purification.

7-(4-(3,6-Difluoro-2-methoxyphenyl)piperidin-1-yl)-3-(2,2,2-trifluoroethyl)-8-(trifluoromethyl)-[1,2,4]triazolo[4,3-b]pyridazine A solution of N'-(5-(4-(3,6-difluoro-2-methoxyphenyl)piperidin-1-yl)-4-(trifluoromethyl)pyridazin-3-yl)-3,3,3-trifluoropropanehydrazide (0.48 g, 0.935 mmol) and phosphorus oxychloride (0.131 ml, 1.402 mmol) in acetonitrile (5 ml) was heated to 80° C. for 16 h. The reaction was cooled and diluted with saturated sodium bicarbonate and ethyl acetate. The ethyl acetate layer was concentrated give a brown oil. The oil was purified by preparative HPLC on a XBridge OBD 19×100 mm column using 30-90% acetonitrile:water containing 20-mM ammonium acetate as the eluent. The product fractions were concentrated to an oil. The oil was dissolved in ethyl acetate, washed with saturated sodium bicarbonate, dried over magnesium sulfate, and concentrated to give 7-(4-(3,6-difluoro-2-methoxyphenyl)piperidin-1-yl)-3-(2,2,2-trifluoroethyl)-8-(trifluoromethyl)-[1,2,4]triazolo[4,3-b]pyridazine (7.2 mg, 1.5%) as a yellow oil. $^1$H NMR (400 MHz, METHANOL-d$_4$) δ 8.75 (s, 1H), 7.05 (ddd, J=11.0, 9.2, 5.1 Hz, 1H), 6.82 (ddd, J=10.3, 9.3, 4.0 Hz, 1H), 4.19 (q, J=10.3 Hz, 2H), 3.94 (d, J=1.8 Hz, 3H), 3.88 (d, J=13.1 Hz, 2H), 3.53-3.36 (m, 3H), 2.37 (qd, J=12.7, 3.1 Hz, 2H), 1.88-1.73 (m, 2H). LCMS: Rt=1.03 min, (M+H)+=495.9.

Example 82

8-Chloro-3-(cyclopropylmethyl)-7-(4-(pyridin-3-yl)piperidin-1-yl)-[1,2,4]triazolo[4,3-b]pyridazine 4-Chloro-3-hydrazinyl-5-(4-(pyridin-3-yl)piperidin-1-yl)pyridazine A mixture of 3,4,5-trichloropyridazine (0.73 g, 4 mmol), 4-(pyridin-3-yl)piperidin-1-ium 2,2,2-trifluoroacetate (1.1 g, 4 mmol), and potassium carbonate (1.16 g, 8.36 mmol) in dioxane (13 ml) and water (1 ml) was heated to reflux for 4 h. The mixture was cooled and 35% hydrazine (7.21 ml, 80 mmol) was added. The mixture was heated to reflux for 16 h. The reaction was diluted with ethyl acetate and water. The ethyl acetate layer was washed with water and concentrated to give 4-chloro-3-hydrazinyl-5-(4-(pyridin-3-yl)piperidin-1-yl)pyridazine as a brown oil. LCMS: Rt=0.75 min, (M+H)+=305.0. The material was used without purification.

N'-(4-Chloro-5-(4-(pyridin-3-yl)piperidin-1-yl)pyridazin-3-yl)-2-cyclopropylacetohydrazide A mixture of 4-chloro-3-hydrazinyl-5-(4-(pyridin-3-yl)piperidin-1-yl)pyridazine (0.60 g, 1.97 mmol), ethyl acetate (2.5 ml), THF (5 ml), and saturated sodium bicarbonate (5 ml) was stirred as 2-cyclopropylacetyl chloride (0.257 g, 2.166 mmol) was added. The mixture was stirred for 16 h. The reaction was diluted with ethyl acetate and saturated sodium bicarbonate. The ethyl acetate layer was separated, washed with water, and concentrated to give N'-(4-chloro-5-(4-(pyridin-3-yl)piperidin-1-yl)pyridazin-3-yl)-2-cyclopropylacetohydrazide as to a brown oil. LCMS: Rt=0.73 min. (M+H)⁺=387.0. The material was used without purification.

8-Chloro-3-(cyclopropylmethyl)-7-(4-(pyridin-3-yl)piperidin-1-yl)-[1,2,4]triazolo[4,3-b]pyridazine A solution of N'-(4-chloro-5-(4-(pyridin-3-yl)piperidin-1-yl)pyridazin-3-yl)-2-cyclopropylacetohydrazide (0.760 g, 1.964 mmol) and phosphorus oxychloride (0.275 ml, 2.95 mmol) in acetonitrile (5 ml) was heated to 80° C. for 16 h. The reaction was cooled and diluted with saturated sodium bicarbonate and ethyl acetate. The ethyl acetate layer was concentrated give a brown oil. The oil was purified by preparative HPLC on a Waters XBridge C18, 19×200 mm column using 20-60% acetonitrile:water with 20-mM ammonium acetate as the eluent. The product fractions were concentrated to an oil. The oil was dissolved in ethyl acetate, washed with saturated sodium bicarbonate, dried over magnesium sulfate, and concentrated to give 8-chloro-3-(cyclopropylmethyl)-7-(4-(pyridin-3-yl)piperidin-1-yl)-[1,2,4]triazolo[4,3-b]pyridazine (18.9 mg, 2.6%) as a brown oil. $^1$H NMR (400 MHz, METHANOL-d$_4$) δ 8.63-8.50 (m, 2H), 8.43 (dd, J=4.9, 1.5 Hz, 1H), 7.85 (d, J=7.8 Hz, 1H), 7.44 (ddd, J=7.9, 4.8, 0.7 Hz, 1H), 4.01-3.84 (m, 2H), 3.32-3.22 (m, 2H), 3.08 (d, J=7.1 Hz, 2H), 3.01-2.86 (m, 1H), 2.12-2.01 (m, 4H), 1.39-1.21 (m, 1H), 0.71-0.51 (m, 2H), 0.43-0.23 (m, 2H). LCMS: Rt=1.90 min, (M+H)⁺=369.1.

Example 83

8-Chloro-7-(4-(3-methoxypyridin-2-yl)piperidin-1-yl)-3-(2,2,2-trifluoroethyl)-[1,2,4]triazolo[4,3-b]pyridazine

4-Chloro-3-hydrazinyl-5-(4-(3-methoxypyridin-2-yl)piperidin-1-yl)pyridazine A mixture of 3,4,5-trichloropyridazine (0.437 g, 2.38 mmol), 4-(3-methoxypyridin-2-yl)piperidin-1-ium 2,2,2-trifluoroacetate (0.73 g, 2.383 mmol), and potassium carbonate (0.692 g, 5 mmol) in dioxane (8 ml) and water (1 ml) was heated to reflux for 4 h. The mixture was cooled and 35% hydrazine (4.32 ml, 47.7 mmol) was added. The mixture was heated to reflux for 16 h. The reaction was diluted with ethyl acetate and water. The ethyl acetate layer was washed with water and concentrated to give 4-chloro-3-hydrazinyl-5-(4-(3-methoxypyridin-2-yl)piperidin-1-yl)pyridazine as a brown oil. LCMS: Rt=0.77 min, (M+H)⁺=334.9. The material was used without purification.

N'-(4-Chloro-5-(4-(3-methoxypyridin-2-yl)piperidin-1-yl)pyridazin-3-yl)-3,3,3-trifluoropropanehydrazide A mixture of 4-chloro-3-hydrazinyl-5-(4-(3-methoxypyridin-2-yl)piperidin-1-yl)pyridazine (0.60 g, 1.792 mmol) in ethyl acetate (2.5 ml), THF (5.00 ml), and saturated sodium bicarbonate (5 ml) was stirred as 3,3,3-trifluoropropanoyl chloride (0.203 ml, 1.971 mmol) was added. The mixture was stirred for 16 h. The reaction was diluted with ethyl acetate and saturated sodium bicarbonate. The ethyl acetate layer was separated, washed with water, and concentrated to give N'-(4-chloro-5-(4-(3-methoxypyridin-2-yl)piperidin-1-yl)pyridazin-3-yl)-3,3,3-trifluoropropanehydrazide as a brown oil. LCMS: Rt=0.78 min, (M+H)⁺=444.9. The material was used without purification.

8-Chloro-7-(4-(3-methoxypyridin-2-yl)piperidin-1-yl)-3-(2,2,2-trifluoroethyl)-[1,2,4]triazolo[4,3-b]pyridazine A solution of N'-(4-chloro-5-(4-(3-methoxypyridin-2-yl)piperidin-1-yl)pyridazin-3-yl)-3,3,3-trifluoropropanehydrazide (0.80 g, 1.8 mmol) and phosphorus oxychloride (0.251 ml, 2.70 mmol) in acetonitrile (5 ml) was heated to 80° C. for 16 h. The reaction was cooled and diluted with saturated sodium bicarbonate and ethyl acetate. The ethyl acetate layer was concentrated give a brown oil. The oil was purified by preparative HPLC on a Waters XBridge C18, 19×200 mm column and 15-70% acetonitrile:water with 20-mM ammonium acetate as the eluent. The product fractions were concentrated to an oil. The oil was dissolved in ethyl acetate, washed with saturated sodium bicarbonate, dried over magnesium sulfate, and concentrated to give 8-chloro-7-(4-(3-methoxypyridin-2-yl)piperidin-1-yl)-3-(2,2,2-trifluoroethyl)-[1,2,4]triazolo[4,3-b]pyridazine (12.4 mg, 1.6%). $^1$H NMR (500 MHz, DMSO-d$_6$) δ 8.75 (s, 1H), 8.12 (d, J=4.6 Hz, 1H), 7.40 (d, J=8.5 Hz, 1H), 7.24 (dd, J=8.2, 4.6 Hz, 1H), 4.34 (q, J=10.4 Hz, 2H), 3.86 (s, 3H), 3.78 (d, J=11.9 Hz, 2H), 3.23 (t, J=12.1 Hz, 3H), 1.98 (d, J=12.2 Hz, 2H), 1.84 (d, J=11.3 Hz, 2H). LCMS: Rt=0.67 min, (M+H)⁺=426.9.

Example 84

3-(Cyclopropylmethyl)-7-(4-(2-fluorophenyl)piperidin-1-yl)-8-(trifluoromethyl)-[1,2,4]triazolo[4,3-b]pyridazine

5-(4-(2-Fluorophenyl)piperidin-1-yl)-4-(trifluoromethyl)pyridazin-3(2H)-one A solution of tert-butyl 5-bromo-4-(4-(2-fluorophenyl)piperidin-1-yl)-6-oxopyridazine-1(6H)-carboxylate (1.2 g, 2.65 mmol) and copper(I) iodide (1.011 g, 5.31 mmol), and methyl 2,2-difluoro-2-(fluorosulfonyl)acetate (0.671 ml, 5.31 mmol) in DMF (24.34 ml) was heated to 100° C. for 2 h. The reaction was filtered through a pad of silica gel, and the pad was rinsed with ethyl acetate. The filtrate was washed with saturated sodium bicarbonate and ammonium chloride. The organic layer was dried over magnesium sulfate, and concentrated to give 5-(4-(2-fluorophenyl)piperidin-1-yl)-4-(trifluoromethyl)pyridazin-3(2H)-one as a brown oil. LCMS: Rt=0.94 min, (M+H)⁺=341.9.

tert-Butyl 4-(4-(2-fluorophenyl)piperidin-1-yl)-6-oxo-5-(trifluoromethyl)pyridazine-1(6H)-carboxylate A solution of 5-(4-(2-fluorophenyl)piperidin-1-yl)-4-(trifluoromethyl)pyridazin-3(2H)-one (0.90 g, 2.64 mmol) in methylene chloride (50 ml), di-tert-butyl dicarbonate (0.735 ml, 3.16 mmol), and triethyl amine (0.55 ml, 4 mmol) stirred for 16 h. The solution was washed with water. The methylene chloride layer was dried over magnesium sulfate, and concentrated to give tert-butyl 4-(4-(2-fluorophenyl)piperidin-1-yl)-6-oxo-5-(trifluoromethyl)pyridazine-1(6H)-carboxylate as a brown oil. LCMS: Rt=1.09 min, (M+H)⁺=341.9. The material was used without purification.

3-Chloro-5-(4-(2-fluorophenyl)piperidin-1-yl)-4-(trifluoromethyl)pyridazine A mixture of tert-butyl 4-(4-(2-fluorophenyl)piperidin-1-yl)-6-oxo-5-(trifluoromethyl)pyridazine-1(6H)-carboxylate (1.1 g, 2.49 mmol) and phosphorus oxychloride (7.67 ml, 82 mmol) was heated to 100° C. for 1 h. The mixture was concentrated. The residue was dissolved in methylene chloride, washed with saturated sodium bicarbonate, dried over magnesium sulfate, and concentrated to give 3-chloro-5-(4-(2-fluorophenyl)piperidin-1-yl)-4-(trifluoromethyl) pyridazine as a brown oil. LCMS: Rt=1.06 min, (M+H)$^+$= 410.9. The material was used without purification.

5-(4-(2-Fluorophenyl)piperidin-1-yl)-3-hydrazinyl-4-(trifluoromethyl)pyridazine

A mixture of 3-chloro-5-(4-(2-fluorophenyl)piperidin-1-yl)-4-(trifluoromethyl)pyridazine (0.89 g, 2.474 mmol), potassium carbonate (0.718 g, 5.2 mmol), and 35% hydrazine (4.5 ml, 49.5 mmol) in dioxane (10 ml) was heated to 100° C. for 2 h. The reaction was diluted with ethyl acetate and water. The ethyl acetate layer was washed with water and concentrated to give 5-(4-(2-fluorophenyl)piperidin-1-yl)-3-hydrazinyl-4-(trifluoromethyl)pyridazine as a brown oil. LCMS: Rt=0.94 min, (M+H)$^+$=356. The material was taken on without purification.

2-Cyclopropyl-N'-(5-(4-(2-fluorophenyl)piperidin-1-yl)-4-(trifluoromethyl)pyridazin-3-yl)acetohydrazide A mixture of 5-(4-(2-fluorophenyl)piperidin-1-yl)-3-hydrazinyl-4-(trifluoromethyl)pyridazine (0.40 g, 1.13 mmol) ethyl acetate (2.5 ml), THF (5 ml), and saturated sodium bicarbonate (5 ml) was stirred as 2-cyclopropylacetyl chloride (0.147 g, 1.238 mmol) was stirred for 16 h. The reaction was diluted with ethyl acetate and water. The ethyl acetate layer was separated, washed with water, and concentrated to give 2-cyclopropyl-N'-(5-(4-(2-fluorophenyl)piperidin-1-yl)-4-(trifluoromethyl)pyridazin-3-yl)acetohydrazide as a brown oil. LCMS: Rt=0.83 min, (M+H)$^+$=438.0. The material was used without purification.

3-(Cyclopropylmethyl)-7-(4-(2-fluorophenyl)piperidin-1-yl)-8-(trifluoromethyl)-[1,2,4]triazolo[4,3-b] pyridazine A solution of 2-cyclopropyl-N'-(5-(4-(2-fluorophenyl)piperidin-1-yl)-4-(trifluoromethyl)pyridazin-3-yl)acetohydrazide (0.50 g, 1.143 mmol) and phosphorus oxychloride (0.16 ml, 1.72 mmol) in acetonitrile (5 ml) was heated to 80° C. for 16 h. The reaction was cooled and diluted with saturated sodium bicarbonate and ethyl acetate. The ethyl acetate layer was concentrated give a brown oil. The oil was purified by preparative HPLC on a Waters XBridge C18, 19×200 mm column and 60-95% acetonitrile:water with 20-mM ammonium acetate as the eluent. The product fractions were concentrated to an oil. The oil was dissolved in ethyl acetate, washed with saturated sodium bicarbonate, dried over magnesium sulfate, and concentrated to give 3-(cyclopropylmethyl)-7-(4-(2-fluorophenyl)piperidin-1-yl)-8-(trifluoromethyl)-[1,2,4]triazolo[4,3-b]pyridazine (5.1 mg, 1%). $^1$H NMR (500 MHz, DMSO-d$_6$) δ 8.76 (s, 1H), 7.40-7.35 (m, 1H), 7.32-7.26 (m, 1H), 7.22-7.15 (m, 2H), 3.74 (d, J=12.5 Hz, 2H), 3.41 (t, J=12.1 Hz, 2H), 3.23-3.03 (m, 1H), 2.98 (d, J=7.0 Hz, 2H), 1.97-1.79 (m, 4H), 1.20 (br. s., 1H), 0.50 (d, J=7.9 Hz, 2H), 0.30 (d, J=5.2 Hz, 2H). LCMS: Rt=0.97 min, (M+H)$^+$=420.0.

Example 85

Trans-N-((2-(2-methoxyphenyl)cyclopropyl) methyl)-3-(2,2,2-trifluoroethyl)-8-(trifluoromethyl)-[1,2,4]triazolo[4,3-b]pyridazin-7-amine Trans-4-bromo-5-(((2-(2-methoxyphenyl)cyclopropyl)methyl)amino)pyridazin-3(2H)-one A solution of 4,5-dibromopyridazin-3(2H)-one (0.80 g, 3.15 mmol), trans-(2-(2-methoxyphenyl)cyclopropyl)methanamine (0.559 g, 3.15 mmol), and DIPEA (1.211 ml, 6.93 mmol) in DMA (6.66 ml) was heated to 100° C. for 16 h. The reaction was cooled, diluted with saturated sodium bicarbonate to give 4-bromo-5-(((2-(2-methoxyphenyl)cyclopropyl)methyl)amino)pyridazin-3(2H)-one as a tan precipitate that was filtered and air dried. LCMS: Rt=1.0 min, (M+H)$^+$=359.

Trans-tert-butyl 5-bromo-4-(((2-(2-methoxyphenyl) cyclopropyl)methyl)amino)-6-oxopyridazine-1(6H)-carboxylate A solution of trans-4-bromo-5-(((2-(2-methoxyphenyl) cyclopropyl)methyl)amino)pyridazin-3(2H)-one (1.0 g, 2.86 mmol), di-tert-butyl dicarbonate (0.796 ml, 3.43 mmol), and triethylamine (0.597 ml, 4.28 mmol) in methylene chloride (20 ml) was stirred for 16 h. The reaction was washed with water and the organic layers dried over magnesium sulfate, and concentrated to give trans-tert-butyl 5-bromo-4-(((2-(2-methoxyphenyl)cyclopropyl)methyl) amino)-6-oxopyridazine-1(6H)-carboxylate as a yellow oil. LCMS: Rt=1.07 min, (M+H)$^+$=351.9.

Trans-5-(((2-(2-methoxyphenyl)cyclopropyl)methyl) amino)-4-(trifluoromethyl)pyridazin-3(2H)-one A solution of trans-tert-butyl 5-bromo-4-(((2-(2-methoxyphenyl)cyclopropyl)methyl)amino)-6-oxopyridazine-1 (6H)-carboxylate (1.3 g, 2.89 mmol) and copper(I) iodide (1.1 g, 5.77 mmol) in DMF (26.5 ml) was stirred as methyl 2,2-difluoro-2-(fluorosulfonyl)acetate (0.73 ml, 5.77 mmol) was added. The solution was heated to 100° C. for 16 h. The reaction was filtered through a pad of silica gel, and the pad was rinsed with ethyl acetate. The filtrate was washed with saturated sodium bicarbonate and saturated ammonium chloride. The ethyl acetate layer was separated, dried over magnesium sulfate, and concentrated to give trans-5-(((2-(2-methoxyphenyl)cyclopropyl)methyl)amino)-4-(trifluoromethyl)pyridazin-3(2H)-one as a brown oil. LCMS: Rt=0.90 min, (M+H)$^+$=340.0.

Trans-tert-butyl 4-(((2-(2-methoxyphenyl)cyclopropyl)methyl)amino)-6-oxo-5-(trifluoromethyl) pyridazine-1(6H)-carboxylate A solution of trans-5-(((2-(2-methoxyphenyl)cyclopropyl)methyl)amino)-4-(trifluoromethyl)pyridazin-3(2H)-one (1.3 g, 3.83 mmol), di-tert-butyl dicarbonate (1.067 ml, 4.6 mmol) and triethyl amine (0.801 ml, 5.75 mmol) in methylene chloride (50 ml) was stirred for 16 h. The reaction was washed with water. The organic layers dried over magnesium sulfate, and concentrated to give trans-tert-butyl 4-(((2-(2-methoxyphenyl)cyclopropyl)methyl)amino)-6-oxo-5-(trifluoromethyl)pyridazine-1(6H)-carboxylate as a brown oil. LCMS: Rt=1.07 min, (M+H)$^+$=339.9.

Trans-6-chloro-N-((2-(2-methoxyphenyl)cyclopropyl)methyl)-5-(trifluoromethyl)pyridazin-4-amine A mixture of trans-tert-butyl 4-(((2-(2-methoxyphenyl) cyclopropyl)methyl)amino)-6-oxo-5-(trifluoromethyl) pyridazine-1(6H)-carboxylate (1.7 g, 3.87 mmol) in phosphorus oxychloride (11.9 ml, 128 mmol) (5 ml) was heated to 100° C. for 4 h. The reaction was cooled and concentrated, The residue was dissolved in methylene chloride and washed with saturated sodium bicarbonate. The organic layer was separated, dried over magnesium sulfate, and concentrated to give trans-6-chloro-N-((2-(2-methoxyphenyl)cyclopropyl)methyl)-5-(trifluoromethyl)pyridazin-4-amine as a brown oil. LCMS: Rt=1.03 min, (M+H)$^+$=357.9.

Trans-6-hydrazinyl-N-((2-(2-methoxyphenyl)cyclopropyl)methyl)-5-(trifluoromethyl)pyridazin-4-amine A mixture of trans-6-chloro-N-((2-(2-methoxyphenyl)cyclopropyl)methyl)-5-(trifluoromethyl)pyridazin-4-amine (1.4 g, 3.91 mmol), potassium carbonate (1.136 g, 8.22 mmol), and 35% hydrazine (7.09 ml, 78 mmol) in dioxane (10 ml) and water (1 ml) was heated to 100° C. for 2 h. The mixture was diluted with ethyl acetate and water. The ethyl acetate layer dried with brine, and concentrated to give trans-6-hydrazinyl-N-((2-(2-methoxyphenyl)cyclopropyl) methyl)-5-(trifluoromethyl)pyridazin-4-amine LCMS: Rt=0.79 min, (M+H)$^+$=354.

Trans-3,3,3-trifluoro-N'-(5-(((2-(2-methoxyphenyl) cyclopropyl)methyl)amino)-4-(trifluoromethyl) pyridazin-3-yl)propanehydrazide A mixture of trans-6-hydrazinyl-N-((2-(2-methoxyphenyl)cyclopropyl)methyl)-5-(trifluoromethyl)pyridazin-4-amine (1.4 g, 3.96 mmol) in ethyl acetate (2.5 ml), THF (5.00 ml), and saturated sodium bicarbonate (5 ml) was stirred as 3,3,3-trifluoropropanoyl chloride (0.449 ml, 4.36 mmol) was added. The mixture was stirred for 2 days. The reaction was diluted with ethyl acetate and water. The ethyl acetate layer was washed with water and concentrated to give trans-3,3,3-trifluoro-N'-(5-(((2-(2-methoxyphenyl)cyclopropyl)methyl)amino)-4-(trifluoromethyl)pyridazin-3-yl)propanehydrazide as a brown oil. LCMS: Rt=0.85 min, (M+H)$^+$=464.

Trans-N-2-(2-methoxyphenyl)cyclopropyl)methyl)-3-(2,2,2-trifluoroethyl)-8-(trifluoromethyl)-[1,2,4] triazolo[4,3-b]pyridazin-7-amine A solution of trans-3,3,3-trifluoro-N'-(5-(((2-(2-methoxyphenyl)cyclopropyl)methyl)amino)-4-(trifluoromethyl) pyridazin-3-yl)propanehydrazide (0.18 g, 0.388 mmol) and phosphorus oxychloride (0.543 ml, 5.83 mmol) in acetonitrile (5 ml) was added and the reaction was heated to 80° C. for 16 h. The reaction was cooled and diluted with ethyl acetate and saturated sodium bicarbonate. The organic layer was concentrated to give a brown oil. The crude material was purified by preparative HPLC on an XBridge C18, 19×mm column, using 30-70% acetonitrile/water containing 10-mM ammonium acetate as the eluent. The product fractions were concentrated. The material was further purified by preparative HPLC on an XBridge Phenyl, 19×mm column, using 30-70% acetonitrile/water containing 10-mM ammonium acetate as the eluent. The product fractions were concentrated to give trans-N-2-(2-methoxyphenyl)cyclopropyl)methyl)-3-(2,2,2-trifluoroethyl)-8-(trifluoromethyl)-[1, 2,4]triazolo[4,3-b]pyridazin-7-amine (1.1 mg, 0.64%). $^1$H NMR (500 MHz, DMSO-d$_6$) δ 8.89 (s, 1H), 7.27 (br. s., 1H), 7.18-7.05 (m, 1H), 6.96-6.75 (m, 3H), 4.26 (q, J=11.0 Hz, 2H), 3.66 (s, 4H), 3.61-3.46 (m, 1H), 2.13 (d, J=5.8 Hz, 1H), 1.33 (d, J=6.4 Hz, 1H), 0.96 (t, J=6.7 Hz, 2H). LCMS: Rt=0.97 min, (M+H)$^+$=446.0.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

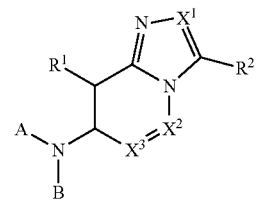

wherein:

A and B together with the nitrogen to which they are attached form ring A which is azetidinyl, pyrrolidinyl, piperidinyl, piperazinyl, morpholinyl, homopiperidinyl, homopiperazinyl, or homomorpholinyl, and is substituted with 1 Ar$^2$ or (Ar$^2$)alkyl substituent and is also substituted with 0-3 substituents selected from halo, alkyl, haloalkyl, hydroxy, alkoxy, and haloalkoxy;

or ring A and B together is selected from the group consisting of

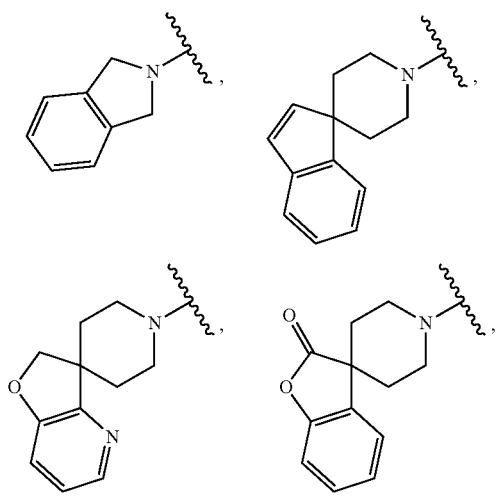

-continued

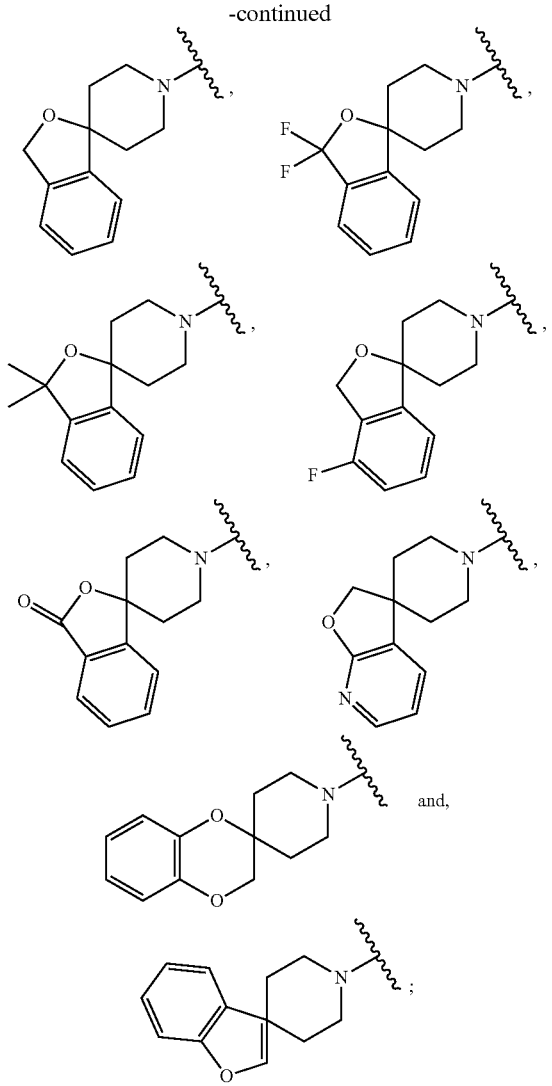

R¹ is selected from the group consisting of cyano, halo, alkyl, haloalkyl, (cycloalkyl)alkyl, cycloalkyl, alkoxy, and haloalkoxy;
R² is selected from the group consisting of alkyl, haloalkyl, (cycloalkyl)alkyl, benzyl, and cycloalkyl;
R³ is hydrogen, alkyl, haloalkyl, or cycloalkyl;
$Ar^2$ is phenyl, pyridinyl, pyridazinyl, pyrimidinyl, pyrazinyl, or triazinyl, and is substituted with 0-3 substituents selected from cyano, halo, alkyl, haloalkyl, hydroxyalkyl, alkoxyalkyl, cycloalkyl, hydroxy, alkoxy, (cycloalkyl)alkoxy, haloalkoxy, and alkoxycarbonyl;
$X^1$ is N;
$X^2$ is $CR^3$ or N; and
$X^3$ is CH or N;
provided that one of $X^2$ and $X^3$ is N, thus when $X^2$ is N, $X^3$ is CH and when $X^3$ is N, $X^2$ is $CR^3$;
or a pharmaceutically acceptable salt thereof.

2. A compound of claim 1 where $X^2$ is N and $X^3$ is CH.
3. A compound of claim 1 where $X^2$ is CH and $X^3$ is N.
4. A compound of claim 1 where R¹ is selected from the group consisting of halo, alkyl, haloalkyl, and alkoxy and R² is selected from the group consisting of alkyl, haloalkyl, (cycloalkyl)alkyl, and benzyl.
5. A compound of claim 1 where $Ar^2$ is phenyl, pyridinyl, or pyrimidinyl, and is substituted with 0-3 substituents selected from cyano, halo, alkyl, haloalkyl, hydroxyalkyl, alkoxyalkyl, cycloalkyl, hydroxy, alkoxy, (cycloalkyl)alkoxy, haloalkoxy, and alkoxycarbonyl.
6. A compound of claim 1 where ring A is piperidinyl substituted with 1 $Ar^2$ substituent and is also substituted with 0-1 hydroxy substituents.
7. A compound of claim 1 where ring A is selected from

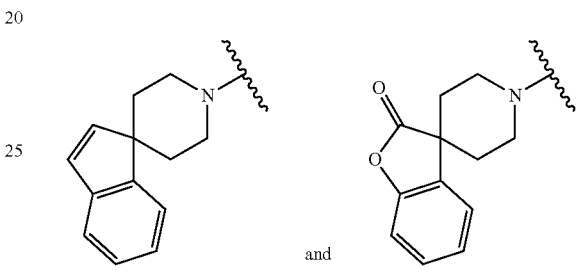

and

8. A compound of claim 1 selected from the group consisting of
3-(cyclopropylmethyl)-7-(4-(3,6-difluoro-2-methoxyphenyl)piperidin-1-yl)-8-(trifluoromethyl)-[1,2,4]triazolo[4,3-b]pyridazine;
7-(4-(3,6-difluoro-2-methoxyphenyl)piperidin-1-yl)-3-(2,2,2-trifluoroethyl)-8-(trifluoromethyl)-[1,2,4]triazolo[4,3-b]pyridazine;
8-chloro-3-(cyclopropylmethyl)-7-(4-(2-(difluoromethoxy)-3,6-difluorophenyl)piperidin-1-yl)-[1,2,4]triazolo[4,3-b]pyridazine;
8-chloro-7-(4-(2-fluoro-6-methoxyphenyl)piperidin-1-yl)-3-(2,2,2-trifluoroethyl)-[1,2,4]triazolo[4,3-b]pyridazine;
3-(cyclopropylmethyl)-7-(4-phenylpiperidin-1-yl)-8-(trifluoromethyl)-[1,2,4]triazolo[4,3-b]pyridazine;
8-chloro-3-(cyclopropylmethyl)-7-(4-(2-fluorophenyl)piperidin-1-yl)-[1,2,4]triazolo[4,3-c]pyrimidine; and
8-chloro-7-(4-(2-fluorophenyl)piperidin-1-yl)-3-(2,2,2-trifluoroethyl)-[1,2,4]triazolo[4,3-c]pyrimidine;
or a pharmaceutically acceptable salt thereof.

9. A composition comprising a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 9,682,980 B2
APPLICATION NO. : 14/406029
DATED : June 20, 2017
INVENTOR(S) : Mattson et al.

Page 1 of 1

It is certified that error appears in the above-identified patent and that said Letters Patent is hereby corrected as shown below:

In the Claims

Claim 1, Column 96, Lines 23-32:

Delete " 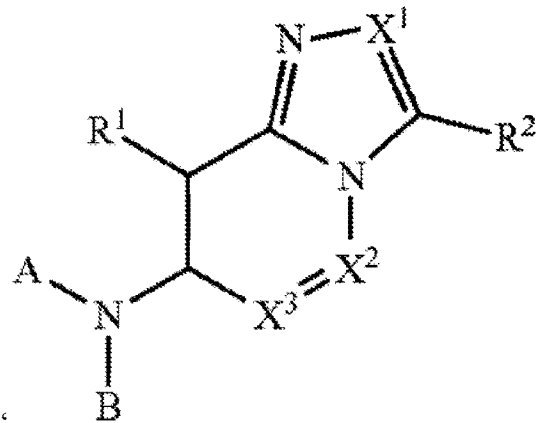 " and insert

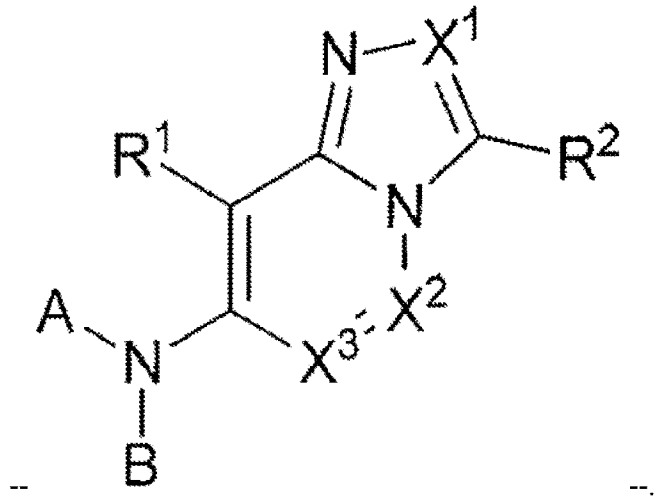

--.

Signed and Sealed this
Eighteenth Day of September, 2018

Andrei Iancu
*Director of the United States Patent and Trademark Office*